US009187435B2

(12) United States Patent
Bur et al.

(10) Patent No.: US 9,187,435 B2
(45) Date of Patent: Nov. 17, 2015

(54) BRIDGED SPIRO[2.4]HEPTANE ESTER DERIVATIVES

(75) Inventors: Daniel Bur, Allschwil (CH); Olivier Corminboeuf, Allschwil (CH); Sylvaine Cren, Allschwil (CH); Corinna Grisostomi, Allschwil (CH); Xavier Leroy, Allschwil (CH); Sylvia Richard-Bildstein, Allschwil (CH); Davide Pozzi, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 72 days.

(21) Appl. No.: 13/988,204

(22) PCT Filed: Nov. 16, 2011

(86) PCT No.: PCT/IB2011/055125
§ 371 (c)(1),
(2), (4) Date: May 17, 2013

(87) PCT Pub. No.: WO2012/066488
PCT Pub. Date: May 24, 2012

(65) Prior Publication Data
US 2013/0231319 A1    Sep. 5, 2013

(30) Foreign Application Priority Data
Nov. 17, 2010  (WO) .................. PCT/IB2010/055231

(51) Int. Cl.
| C07C 69/753 | (2006.01) |
| C07D 263/32 | (2006.01) |
| C07D 211/22 | (2006.01) |
| C07D 213/75 | (2006.01) |
| C07D 261/08 | (2006.01) |
| C07D 401/12 | (2006.01) |
| C07D 413/12 | (2006.01) |
| C07D 207/10 | (2006.01) |
| C07D 295/088 | (2006.01) |
| C07D 211/42 | (2006.01) |
| C07D 205/04 | (2006.01) |
| C07D 207/08 | (2006.01) |
| C07D 207/12 | (2006.01) |
| C07D 211/14 | (2006.01) |
| C07D 241/04 | (2006.01) |

(52) U.S. Cl.
CPC ............ *C07D 263/32* (2013.01); *C07C 69/753* (2013.01); *C07D 205/04* (2013.01); *C07D 207/08* (2013.01); *C07D 207/10* (2013.01); *C07D 207/12* (2013.01); *C07D 211/14* (2013.01); *C07D 211/22* (2013.01); *C07D 211/42* (2013.01); *C07D 213/75* (2013.01); *C07D 241/04* (2013.01); *C07D 261/08* (2013.01); *C07D 295/088* (2013.01); *C07D 401/12* (2013.01); *C07D 413/12* (2013.01)

(58) Field of Classification Search
None
See application file for complete search history.

(56) References Cited

U.S. PATENT DOCUMENTS

| 8,288,419 B2 | 10/2012 | Bur et al. |
| 8,618,163 B2 * | 12/2013 | Beard et al. .................. 514/510 |
| 8,846,733 B2 | 9/2014 | Bur et al. |
| 2010/0331378 A1 | 12/2010 | Bur et al. |
| 2012/0101138 A1 | 4/2012 | Bur et al. |
| 2012/0115841 A1 | 5/2012 | Bur et al. |
| 2012/0115916 A1 | 5/2012 | Bur et al. |
| 2013/0261159 A1 | 10/2013 | Bur et al. |
| 2013/0267569 A1 | 10/2013 | Bur et al. |

FOREIGN PATENT DOCUMENTS

| WO | WO 95/02587 | 1/1995 |
| WO | WO 03/082314 | 10/2003 |
| WO | WO 2005/040120 | 5/2005 |
| WO | WO 2005/047899 | 5/2005 |
| WO | WO 2008/121687 | 10/2008 |
| WO | WO 2009/054941 | 4/2009 |
| WO | WO 2009/077954 | 6/2009 |
| WO | WO 2009/077990 | 6/2009 |
| WO | WO 2010/056633 | 5/2010 |
| WO | WO 2010/081859 | 7/2010 |
| WO | WO 2010/134014 | 11/2010 |
| WO | WO 2010/143116 | 12/2010 |

(Continued)

OTHER PUBLICATIONS

Bannenberg g., "Anti-Inflammatory Actions of Lipoxins," Exp. Opin. Ther. Patents (2007), 17(6), pp. 591-605.
Burli, R. W. et al., "Potent hFPRL2 (ALXR) Agonists as Potential Anti-Inflammatory Agents" Bioorganic & Medicinal Chemistry Letters (2006), 16, p. 3713-3718.
Celik G.E. et al., "Lipoxin A4 Levels in Asthma: Relation with Disease Severity and Aspirin Sensitivity," Clin and Experimental Allergy (2007), 37, pp. 1494-1501.

(Continued)

*Primary Examiner* — Theodore R West
(74) *Attorney, Agent, or Firm* — Hunton & Williams LLP

(57) ABSTRACT

The invention relates to a method for preparing linear polymers having an amide end or having a star architecture comprising an amide core, by means of a ring opening using lactide and glycolide monomers or a lactide monomer ring in the presence of a catalyst, wherein the method includes the steps of: (i) reacting the excess monomer(s) with an initiator in a solvent, said initiator being selected from among an amine and an amino alcohol, given that the initiator has at least one primary or secondary amine function; (ii) adding a catalyst, said catalyst being a non-nucleophilic base and including at least one neutral sp2 nitrogen atom; and (iii) neutralizing the reaction mixture. Said novel method is particularly advantageous in that it can be easily monitored and enables better modulation of the polymers, and thus of the properties thereof, than the methods of the prior art. The invention also relates to novel polymers that are obtainable by means of said method.

14 Claims, No Drawings

(56) References Cited

FOREIGN PATENT DOCUMENTS

| WO | WO 2010/143158 | 12/2010 |
|---|---|---|
| WO | WO 2011/061679 | 5/2011 |
| WO | WO 2011/163502 | 12/2011 |
| WO | 2012077049 A1 | 6/2012 |
| WO | 2012077051 A1 | 6/2012 |
| WO | WO 2013/171687 | 11/2013 |
| WO | WO 2013/171694 | 11/2013 |

OTHER PUBLICATIONS

Chiang N. et al., "The Lipoxin Receptor ALX: Potent Ligand-Specific and Stereoselective Actions in Vivo" Pharmacol. Rev. (2006), 58, No. 3, pp. 463-487.

Coe J. W. et al., "The Lipoxin Receptor ALX: Potent Ligand-Specific and Stereoselective Actions in Vivo" Org. Letters (2004), 6, pp. 1589-1592.

Edwards B. S. et al., "Formation of 3-Halobenzyne: Solvent Effects and Cycloaddition Adducts" (2005) Molecular Pharmacology, 68, No. 5 (3), pp. 1301-1310.

G. Helmchen et al., "High Stereoselectivity in Lewis-Acid-Catalyzed and Uncatalyzed Diels-Alder Reactions of the Fumarate of (S)-Ethyl Lactate", *Angew. Chem. Int. Ed*. 1987, 26, p. 1143.

Gewirtz, A. et al., "Mechanisms of Active Intestinal Inflammation and Potential Down-Regulation via Lipoxins", Eicosanoids and other Bioactive Lipids in Cancer, Inflammation, and Radiation Injury, (2002) 5, Kluwer Academic/Plenum Publishers, pp. 229-236.

Gould, Philip, "Salt selection for basic drugs," International Journal of Pharmaceuticals, (1986) 33, pp. 201-217.

Greene, T. W. et al., "Protective Groups in Organic Synthesis," Protecting Groups in Organic Synthesis, 3rd Edition, (1999) pp. 749-779.

Gronert, K. et al., "A Role for the Mouse 12/15-Lipoxyganase Pathway in Promoting Epithelial Wound Healing and Host Defense" J. Biol. Chem. (2005), 280(15), pp. 15267-15278.

Gronert, Karsten "Lipoxins in the eye and their role in would healing" Prostaglandins, Leukotrienes and Essential Fatty Acids, (2005) pp. 221-229.

Jin, Sheng-Wei et al., "Posttreatment with Aspiring-Triggered Lipoxin A4 Analog Attenuates Lipopolysaccharide-Induced Acute Lung Injury in Mice: The Role of Heme Oxygenase-1" Anesthesia & Analgesia, (2007), 104, pp. 369-377.

Karp, C. L. et al., "Defective Lipoxin-Mediated Anti-Inflammatory Activity in the Cystic Fibrosis Airway" Nature Immunology (2004), 5, pp. 388-392.

Le, Y. et al., "Biologically Active Peptides Interacting with the G Protein-Coupled Formylpeptide Receptors" Protein & Peptide Letters. (2007), 14, pp. 846-853.

Levy Bruce D. et al., "Lipoxin A4 Stable Analogs Reduce Allergic Airway Responses via Mechanisms Distinct from CysLT1 Receptor Antagonism", The FASEB Journal (2007) 21, pp. 3877-3884.

Levy Bruce D. et al., "Multi-Pronged Inhibition of Airway Hyper-Responsiveness and Inflammation by Lipoxin A4", Nature Medicine (2002) 8, pp. 1018-1023.

Miao Jianting et al., "S14-Humanin Ameliorates Ab25-35-Induced Behaviorial Deficits by Reducing Neuroinflammatory Response and Apoptosis in Mice", Neuropeptides (2008) 42, pp. 557-567.

Planaguma Anna et al., "Airway LXA4 Generation and LXA4 Expression Are Decreased in Severe Asthma", Am. J. Respir. Crit. Car Med. (2008) 178, pp. 574-582.

Remington: The Science and Practice of Pharmacy, 21st Edition, Lippincott, Williams and Wilkins Publishing, The University of the Sciences in Philadelphia, 2005.

Schwab, Jan M. et al., "Lipoxins and New Lipid Mediators in the Resolution of Inflammation" Current Opinion in Pharmacology (2006), pp. 414-420.

Sodin-Semrl, S. et al., "Lipoxin A4 Counteracts Synergistic Activation of Human Fibroblast-Like Synoviocytes" Int. J. Immunopathol Pharmacology, (2004) 17, pp. 15-25.

Yazawa Hiroshi et al., "β Amyloid Peptide ($AB_{42}$) is Internalized via the G-Protein-Coupled Receptor FPRL1 and Forms Fibrillar Aggregates in Macrophages" FASEB J., (2001), 15(13), pp. 2454-2462.

Ying, Guoguang et al., "Humanin, a Newly identified Neuroprotective Factor, Uses the G Protein-Coupled Formylpeptide Receptor-Like-1 as a Functional Receptor", J. Immunology (2004), 172, pp. 7078-7085.

Zhang, L. et al., "BML-111, a lipoxin receptor agonist, modulates the immune response and reduces the severity of collagen-induced arthritis" Inflamm. Res. (2008), 57, pp. 157-162.

International Search Report of PCT/IB2011/055125, mailed May 25, 2012.

\* cited by examiner

BRIDGED SPIRO[2.4]HEPTANE ESTER DERIVATIVES

CROSS-REFERENCE TO RELATED APPLICATIONS

This application is the U.S. National Phase of International Application No. of PCT/IB2011/055125, filed Nov. 16, 2011, which claims priority to PCT/IB2010/055231, filed Nov. 17, 2010, the contents of each are hereby incorporated by reference in their entireties.

The present invention relates to bridged spiro[2.4]heptane ester derivatives of formula (I) and their use as pharmaceuticals. The invention also concerns related aspects including processes for the preparation of the compounds, pharmaceutical compositions containing one or more compounds of formula (I), and especially their use as ALX receptor agonists.

ALXR (alias Lipoxin A4 Receptor, FPRL1, FPR2; disclosed in WO2003/082314 as nucleotide sequence SEQ ID NO:1 and amino acid sequence SEQ ID NO:2) is a member of the G-protein coupled receptor family. ALXR was found to mediate calcium mobilisation in response to high concentration of the formyl-methionine-leucyl-phenylalanine peptide. Furthermore, a lipid metabolite, lipoxin A4 (LXA4), and its analogues, were found to bind ALXR with high affinity and increase arachidonic acid production and G-protein activation in ALXR transfected cells (Chiang et al., Pharmacol. Rev., 2006, 58, 463-487). The effects of LXA4 have been evaluated in a variety of animal models of diseases; and LXA4 was demonstrated to have potent anti-inflammatory and pro-resolution activities. The disease models where LXA4, or derivatives, or stable analogs, demonstrated in vivo activities are for example dermal inflammation, dorsal air pouch, ischemia/reperfusion injury, peritonitis, colitis, mesangioproliferative nephritis, pleuritis, asthma, cystic fibrosis, sepsis, corneal injury, angiogenesis, periodontitis, carrageenan-induced hyperalgesia, and graft-vs-host disease (GvHD) (Schwab and Serhan, Current Opinion in Pharmacology, 2006, 414-420). ALXR was also identified as a functional receptor of a various number of peptides, including a fragment of the prion protein, a peptide derived from gp120 of the Human Immunodeficiency Virus (HIV)-1$_{LAI}$ strain, and amyloid-beta 1-42 (Ab42) (for review, Le et al., Protein Pept Lett., 2007, 14, 846-853), and has been suggested to participate in the pathogenesis of Alzheimer's Disease (AD) in several crucial ways (Yazawa et al., FASEB J., 2001, 15, 2454-2462). Activation of ALXR on macrophages and microglial cells initiates a G protein-mediated signalling cascade that increases directional cell migration, phagocytosis, and mediator release. These events may account for the recruitment of mononuclear cells to the vicinity of senile plaques in the diseased areas of AD brain where Ab42 is overproduced and accumulated. Although accumulation of leukocytes at the sites of tissue injury may be considered an innate host response aimed at the clearance of noxious agents, activated mononuclear phagocytes also release a variety of substances such as superoxide anions that may be toxic to neurons. Thus, ALXR may mediate pro-inflammatory responses elicited by Ab42 in AD brain and exacerbate disease progression. It was also reported that humanin (HN), a peptide with neuroprotective capabilities, shares the human ALXR with Ab42 on mononuclear phagocytes and neuronal cell lines and it has been suggested that the neuroprotective activity of HN may be attributed to its competitive occupation of ALXR (Ying et al., J. Immunol., 2004, 172, 7078-7085).

The biological properties of ALXR agonists include, but are not limited to, monocyte/macrophage/microglia/dendritic cell migration/activation, neutrophil migration/activation, regulation of lymphocyte activation, proliferation and differentiation, regulation of inflammation, regulation of cytokine production and/or release, regulation of proinflammatory mediator production and/or release, regulation of immune reaction.

The present invention provides bridged spiro[2.4]heptane ester derivatives, which are non-peptide agonists of human ALX receptor. Compounds of formula (I) may also have agonistic activity on human FPRL2 receptor. Other bridged spiro[2.4]heptane derivatives with agonistic activity on human ALX receptor have been disclosed in WO 2010/134014. Different bridged spiro[2.4]heptane derivatives have been disclosed in WO95/02587. The compounds are useful for the prevention or treatment of diseases, which respond to the modulation of the ALX receptor and/or FPRL2 such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the prevention or treatment of autoimmune diseases and for the modulation of immune responses (especially those elicited by vaccination).

Various embodiments of the invention are presented hereafter:

1) The present invention relates to compounds of the formula (I),

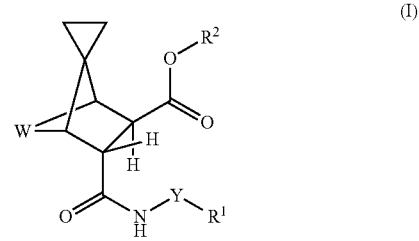

wherein

W represents —CH$_2$CH$_2$— or —CH=CH—;

Y represents a bond or a (C$_1$-C$_2$)alkandiyl group;

R$^1$ represents an aryl- or a heteroaryl-group, which groups are independently unsubstituted, mono-, di- or tri-substituted (preferably mono- or di-substituted), wherein the substituents are independently selected from the group consisting of halogen, (C$_1$-C$_4$)alkyl, (C$_1$-C$_4$)alkoxy, (C$_1$-C$_2$)fluoroalkyl and (C$_1$-C$_2$)fluoroalkoxy;

R$^2$ represents (C$_3$-C$_6$)cycloalkyl, which is unsubstituted or mono-substituted with R$^3$R$^4$N—CH$_2$— or heterocyclyl-methyl; or (C$_2$-C$_6$)alkyl, which is unsubstituted;

mono-substituted with —NR$^3$R$^4$, —C(O)NR$^5$R$^6$, (C$_1$-C$_4$)alkoxy, or (C$_1$-C$_4$)alkoxy which is mono-substituted with heterocyclyl, which heterocyclyl is unsubstituted, or mono-substituted at a nitrogen atom with (C$_1$-C$_4$)alkyl and/or independently mono- or di-substituted at one or two of the carbon atoms with substituents independently selected from halogen and (C$_1$-C$_4$)alkyl; or mono- or di-substituted with hydroxy; or (C$_1$-C$_6$)alkyl (preferably (C$_1$-C$_5$)alkyl), which is mono-substituted
  with (C$_3$-C$_6$)cycloalkyl, which cycloalkyl is mono-substituted with —NR$^3$R$^4$;
  with heterocyclyl, which heterocyclyl is unsubstituted, or mono-substituted at a nitrogen atom with (C$_1$-C$_4$)alkyl and/or independently mono- or di-substituted at one or two of the carbon atoms with substituents independently selected from halogen and (C$_1$-C$_4$)alkyl; or
  with an aryl- or heteroaryl-group, which groups are independently unsubstituted, mono-, di- or tri-substituted, wherein the substituents are independently selected from the group consisting of halogen, (C$_1$-C$_4$)alkyl, —CH$_2$NH$_2$ and —SO$_2$NH$_2$; or (C$_3$-C$_5$)fluoroalkyl, which is mono-substituted with heterocyclyl, which heterocyclyl is unsubstituted or independently mono- or di-substituted at one or two of the carbon atoms with substituents independently selected from halogen and (C$_1$-C$_4$)alkyl; or heterocyclyl, which is unsubstituted, or mono-substituted at a nitrogen atom with (C$_1$-C$_4$)alkyl or benzyl, and/or independently mono- or di-substituted at one or two of the carbon atoms with substituents independently selected from halogen and (C$_1$-C$_4$)alkyl;

R$^3$ and R$^4$ represent independently from each other hydrogen or (C$_1$-C$_3$)alkyl; and R$^5$ and R$^6$ represent independently from each other hydrogen or methyl; or R$^5$ and R$^6$ form, together with the nitrogen that carries them, a pyrrolidine or piperidine ring;

and to the salts (in particular pharmaceutically acceptable salts) of such compounds.

For avoidance of any doubt, the configuration of compounds of formula (I) according to embodiment 1) is such that the substituent R$^1$—Y—NH—C(O)— is in relative proximity to the group W (endo-position), whereas the substituent R$^2$—O—C(O)— is in relative proximity to the cyclopropyl-moiety (exo-position).

Formula I comprises compounds of formula I$_{St1}$ and of formula I$_{St2}$ and mixtures thereof.

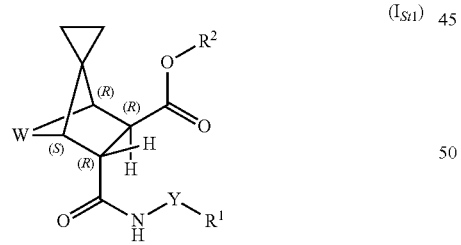
(I$_{St1}$)

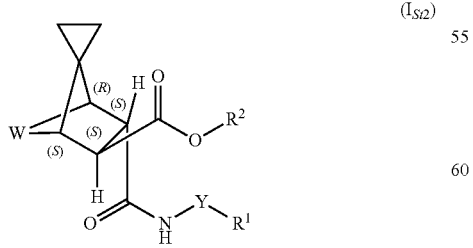
(I$_{St2}$)

For avoidance of doubt, compounds of formula (I) and their chemical precursors are denominated in analogy to the following examples:

the pure stereoisomer of structure

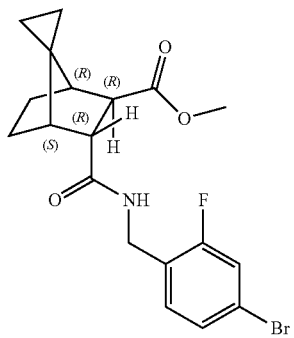

is denominated (5R)—N$^5$-(4-bromo-2-fluorophenyl-methyl)-(6R)-6-methoxycarbonyl-(4S,7R)-[4,7-ethylene-spiro[2.4]heptane]-5-carboxamide;

the pure stereoisomer of structure

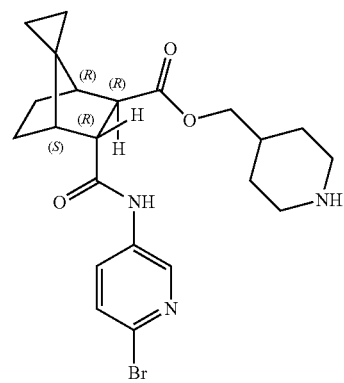

is denominated (1S,2R,3R,4R)-[piperidin-4-ylmethyl 2-((6-bromopyridin-3-yl)carbamoyl)spiro[bicyclo[2.2.1] heptane-7,1'-cyclopropane]-3-carboxylate]; and the pure stereoisomer of structure

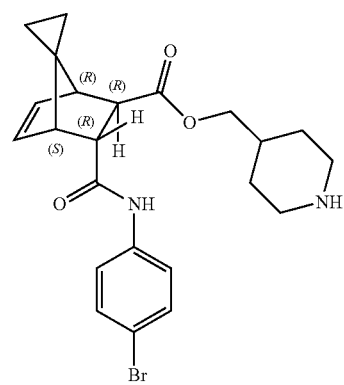

is denominated (1R,4S,5R,6R)-[piperidin-4-ylmethyl 5-((4-bromophenyl)carbamoyl)spiro[bicyclo[2.2.1]hept[2]ene-7,1'-cyclopropane]-6-carboxylate].

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and are intended to apply uniformly throughout the specification and claims unless an otherwise expressly set out definition provides a broader or narrower definition.

The term "alkyl", used alone or in combination, refers to a straight or branched chain alkyl group containing one to six carbon atoms. The term "$(C_x$-$C_y)$alkyl" (x and y each being an integer), refers to an alkyl group as defined before containing x to y carbon atoms. For example a $(C_1$-$C_6)$alkyl group contains from one to six carbon atoms. Representative examples of alkyl groups include methyl, ethyl, n-propyl, iso-propyl, n-butyl, iso-butyl, sec-butyl, tert-butyl, the isomeric pentyls and the isomeric hexyls. The alkyl group may be unsubstituted or substituted as explicitly defined.

In case a $(C_1$-$C_4)$alkyl group is a substituent to an aryl-, a heteroaryl- or a heterocyclyl-group, the term "$(C_1$-$C_4)$alkyl" means $(C_1$-$C_4)$alkyl groups as defined above. Examples of said groups are methyl, ethyl, n-propyl, iso-propyl, n-butyl, iso-butyl, sec-butyl and tert-butyl. Preferred are methyl, ethyl and iso-butyl, and most preferred is methyl.

In case "$R^2$" represents "$(C_2$-$C_6)$alkyl which is unsubstituted; mono-substituted with —$NR^3R^4$, —$C(O)NR^5R^6$, $(C_1$-$C_4)$alkoxy, or $(C_1$-$C_4)$alkoxy which is mono-substituted with heterocyclyl, which heterocyclyl is unsubstituted, or mono-substituted at a nitrogen atom with $(C_1$-$C_4)$alkyl and/or independently mono- or di-substituted at one or two of the carbon atoms with substituents independently selected from halogen and $(C_1$-$C_4)$alkyl; or mono- or di-substituted with hydroxy" the term "$(C_2$-$C_6)$alkyl" means $(C_2$-$C_6)$alkyl groups as defined above. Examples of said groups are ethyl, n-propyl, iso-propyl, n-butyl, iso-butyl, sec-butyl, tert-butyl, the isomeric pentyls and the isomeric hexyls. Preferred are ethyl, n-propyl, iso-propyl, n-butyl, iso-butyl, 2,2-dimethyl-prop-1-yl, 3-methyl-but-1-yl, 3,3-dimethyl-but-1-yl, pent-1-yl, pent-2-yl, 4-methyl-pent-2-yl and hex-1-yl. Most preferred are ethyl, n-propyl, n-butyl, iso-butyl, 2,2-dimethyl-prop-1-yl and pent-1-yl (and notably ethyl and n-propyl).

In case "$R^2$" represents "$(C_1$-$C_6)$alkyl, which is mono-substituted with $(C_3$-$C_6)$cycloalkyl, which cycloalkyl is mono-substituted with —$NR^3R^4$; with heterocyclyl, which heterocyclyl is unsubstituted, or mono-substituted at a nitrogen atom with $(C_1$-$C_4)$alkyl and/or independently mono- or di-substituted at one or two of the carbon atoms with substituents independently selected from halogen and $(C_1$-$C_4)$alkyl; or with an aryl- or heteroaryl-group, which groups are independently unsubstituted, mono-, di- or tri-substituted, wherein the substituents are independently selected from the group consisting of halogen, $(C_1$-$C_4)$alkyl, —$CH_2NH_2$ and —$SO_2NH_2$" the term "$(C_1$-$C_6)$alkyl" means $(C_1$-$C_6)$alkyl groups as defined above. Examples of said groups are methyl, ethyl, n-propyl, iso-propyl, n-butyl, iso-butyl, sec-butyl, tert-butyl, the isomeric pentyls and the isomeric hexyls. Preferred are methyl, ethyl, n-propyl, n-butyl and n-pentyl. More preferred are n-butyl and n-pentyl and most preferred is n-butyl. In another preferred embodiment the term $(C_1$-$C_6)$alkyl means methyl.

In case "$R^3$" represents "$(C_1$-$C_3)$alkyl" the term means $(C_1$-$C_3)$alkyl groups as defined above. Examples of said groups are methyl, ethyl, n-propyl and iso-propyl. Preferred are methyl, ethyl and n-propyl. Most preferred are methyl and ethyl.

In case "$R^4$" represents "$(C_1$-$C_3)$alkyl" the term means $(C_1$-$C_3)$alkyl groups as defined above. Examples of said groups are methyl, ethyl, n-propyl and iso-propyl. Preferred are methyl, ethyl and n-propyl. Most preferred are methyl and ethyl.

The term "$(C_1$-$C_2)$alkandiyl group" as used in Y refers to a carbon chain containing from one to two carbon atoms, which is attached to the residue $R^1$ and to the amide-nitrogen atom of the rest of the molecule as depicted in formula (I). The respective two residues may be attached to the same or to different carbon atoms of the alkandiyl group. Preferred examples of $(C_1$-$C_2)$alkandiyl groups are methandiyl, ethan-1,1-diyl and ethan-1,2-diyl. More preferred are methandiyl and ethan-1,2-diyl. Most preferred is methandiyl.

The term "$(C_3$-$C_6)$cycloalkyl", alone or in combination, means a cycloalkyl group with 3 to 6 carbon atoms. Examples of $(C_3$-$C_6)$cycloalkyl groups are cyclopropyl, cyclobutyl, cyclopentyl and cyclohexyl. The $(C_3$-$C_6)$cycloalkyl group may be unsubstituted or substituted as explicitly defined.

In case "$R^2$" represents "$(C_3$-$C_6)$cycloalkyl" the term means $(C_3$-$C_6)$cycloalkyl groups as defined above. Examples of said groups are cyclopropyl, cyclobutyl, cyclopentyl and cyclohexyl. Preferred are cyclopropyl, cyclopentyl and cyclohexyl. Most preferred are cyclopentyl and cyclohexyl.

In case "$R^2$" represents "$(C_1$-$C_6)$alkyl, which is mono-substituted with $(C_3$-$C_6)$cycloalkyl" the term "$(C_3$-$C_6)$cycloalkyl" means the above-mentioned groups. Preferred are cyclopropyl and cyclohexyl.

The term "alkoxy", used alone or in combination, refers to an alkyl-O— group wherein the alkyl group is as defined before. The term "$(C_x$-$C_y)$alkoxy" (x and y each being an integer) refers to an alkoxy group as defined before containing x to y carbon atoms. For example a $(C_1$-$C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy. The alkoxy group may be unsubstituted or substituted as explicitly defined.

In case a $(C_1$-$C_4)$alkoxy group is a substituent to an aryl- or a heteroaryl-group, the term "$(C_1$-$C_4)$alkoxy" means $(C_1$-$C_4)$alkoxy groups as defined above. Examples of said groups are methoxy, ethoxy, n-propoxy, iso-propoxy, n-butoxy, iso-butoxy, sec-butoxy and tert-butoxy. Preferred are methoxy, ethoxy and iso-propoxy. Most preferred is methoxy.

In case "$R^2$" represents "$(C_2$-$C_6)$alkyl which is mono-substituted with $(C_1$-$C_4)$alkoxy" the term "$(C_1$-$C_4)$alkoxy" means a $(C_1$-$C_4)$alkoxy group as defined above. Examples of said groups are methoxy, ethoxy, n-propoxy, iso-propoxy, n-butoxy, iso-butoxy, sec-butoxy and tert-butoxy. Preferred are methoxy and ethoxy and most preferred is methoxy.

In case "$R^2$" represents "$(C_2$-$C_6)$alkyl which is mono-substituted with $(C_1$-$C_4)$alkoxy which is mono-substituted with heterocyclyl" the term "$(C_1$-$C_4)$alkoxy" means a $(C_1$-$C_4)$ alkoxy group as defined above. Examples of said groups are methoxy, ethoxy, n-propoxy, iso-propoxy, n-butoxy, iso-butoxy, sec-butoxy and tert-butoxy. Preferred are methoxy and ethoxy and most preferred is ethoxy.

The term "$(C_x$-$C_y)$fluoroalkyl" (x and y each being an integer) refers to an alkyl group as defined before containing x to y carbon atoms in which one or more (and possibly all) hydrogen atoms have been replaced with fluorine. The fluoroalkyl group may be unsubstituted or substituted as explicitly defined.

In case a $(C_1$-$C_2)$fluoroalkyl group is a substituent to an aryl- or a heteroaryl-group, the term "$(C_1$-$C_2)$fluoroalkyl" means $(C_1$-$C_2)$fluoroalkyl groups as defined above. Examples of said groups are trifluoromethyl, difluoromethyl and 2,2,2- trifluoroethyl. Preferred are trifluoromethyl and 2,2,2-trifluoroethyl. Most preferred is trifluoromethyl.

In case "$R^2$" represents "$(C_3-C_5)$fluoroalkyl" the term means a $(C_3-C_5)$fluoroalkyl group as defined above. Examples of said groups are 2-fluoro-propyl, 2,2-difluoro-propyl, 2-fluoro-butyl, 2,2-difluoro-butyl, 3-fluoro-butyl, 3,3-difluoro-butyl, 2-fluoro-pentyl, 2,2-difluoro-pentyl, 3-fluoro-pentyl, 3,3-difluoro-pentyl, 4-fluoro-pentyl and 4,4-difluoro-pentyl. Preferred are 3-fluoro-butyl, 3,3-difluoro-butyl and 4,4-difluoro-pentyl. More preferred are 3-fluoro-butyl and 3,3-difluoro-butyl. Most preferred is 3-fluoro-butyl.

The term "$(C_x-C_y)$fluoroalkoxy" (x and y each being an integer) refers to an alkoxy group as defined before containing x to y carbon atoms in which one or more (and possibly all) hydrogen atoms have been replaced with fluorine. For example a $(C_1-C_2)$fluoroalkoxy group contains from one to two carbon atoms in which one to five hydrogen atoms have been replaced with fluorine. Representative examples of fluoroalkoxy groups include trifluoromethoxy, difluoromethoxy and 2,2,2-trifluoroethoxy. Preferred are $(C_1)$fluoroalkoxy groups such as trifluoromethoxy and difluoromethoxy. Most preferred is trifluoromethoxy.

The term halogen means fluoro, chloro, bromo or iodo.

In case the halogen is a substituent to an aryl- or a heteroaryl-group, the term means preferably fluoro, chloro or bromo and most preferably chloro or bromo.

In case the halogen is a substituent to a heterocyclyl-group, the term means most preferably fluoro.

The term "aryl", used alone or in any combination, means a phenyl or a naphthyl group. Preferred is a phenyl group. The aryl group may be unsubstituted or substituted as explicitly defined.

In case $R^1$ represents "aryl" the term means the above-mentioned groups (preferably phenyl), which groups are independently unsubstituted, mono-, di- or tri-substituted (preferably unsubstituted, mono- or di-substituted and most preferably mono- or di-substituted), wherein the substituents are independently selected from the group consisting of halogen, $(C_1-C_4)$alkyl, $(C_1-C_4)$alkoxy, $(C_1-C_2)$fluoroalkyl and $(C_1-C_2)$fluoroalkoxy. Preferably the substituents are independently selected from the group consisting of halogen, $(C_1-C_4)$ alkyl, $(C_1-C_4)$alkoxy, trifluoromethyl and trifluoromethoxy (more preferably from fluoro, bromo, methoxy and trifluoromethyl and most preferably from fluoro and bromo). Examples of such aryl groups are 4-methoxyphenyl, 4-trifluoromethylphenyl, 2,4-dichloro-phenyl, 4-bromophenyl, 4-bromo-2-fluoro-phenyl, 4-bromo-3-fluoro-phenyl and 4-bromo-2,6-difluoro-phenyl (and preferably 4-bromophenyl and 4-bromo-2-fluoro-phenyl).

In case $R^2$ represents "$(C_1-C_6)$alkyl, which is mono-substituted with an aryl group" the term "aryl" means the above-mentioned groups (preferably phenyl), which groups are independently unsubstituted, mono-, di- or tri-substituted (preferably unsubstituted or mono-substituted and most preferably mono-substituted), wherein the substituents are independently selected from the group consisting of halogen, $(C_1-C_4)$alkyl, —$CH_2NH_2$, and —$SO_2NH_2$. Preferably the substituents are independently selected from the group consisting of halogen, —$CH_2NH_2$ and —$SO_2NH_2$ (more preferably from —$CH_2NH_2$ and —$SO_2NH_2$ and most preferably from —$CH_2NH_2$). Examples of such aryl groups are 4-fluorophenyl, 2-chlorophenyl, 3-aminomethyl-phenyl, 4-aminomethyl-phenyl, and 4-sulfamoyl-phenyl (preferably 3-aminomethyl-phenyl, 4-aminomethyl-phenyl and 4-sulfamoyl-phenyl and most preferably 3-aminomethyl-phenyl).

The term "heteroaryl", used alone or in any combination, means a 5- to 10-membered monocyclic or bicyclic aromatic ring containing 1, 2 or 3 heteroatoms independently selected from oxygen, nitrogen and sulfur (preferably containing 1 or 2 heteroatoms independently selected from oxygen and nitrogen). Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, naphthyridinyl, cinnolinyl, quinazolinyl, quinoxalinyl and phthalazinyl. The heteroaryl group may be unsubstituted or substituted as explicitly defined.

In case $R^1$ represents "heteroaryl" the term means the above-mentioned groups. Preferred heteroaryl groups as used in $R^1$ are furanyl (notably furan-2-yl), oxazolyl (notably oxazol-2-yl and oxazol-5-yl), isoxazolyl (notably isoxazol-3-yl), oxadiazolyl (notably [1,2,5]oxadiazolyl), thienyl (notably thiophen-2-yl and thiophen-3-yl), thiazolyl (notably thiazol-2-yl, thiazol-4-yl and thiazol-5-yl), thiadiazolyl (notably [1,2,4]thiadiazol-5-yl and [1,3,4]thiadiazol-5-yl), imidazolyl (notably imidazol-1-yl and imidazol-2-yl), pyridyl (notably pyridin-2-yl and pyridin-3-yl), pyrimidyl (notably pyrimidin-5-yl), pyrazinyl (notably pyrazin-2-yl), indolyl (notably indol-1-yl and indol-5-yl), benzimidazolyl (notably benzimidazol-2-yl), benzoxazolyl (notably benzoxazol-6-yl), benzothiazolyl (notably benzothiazol-2-yl and benzothiazol-5-yl), benzoisothiazolyl (notably benzoisothiazol-5-yl) and benzo[2,1,3]oxadiazolyl (notably benzo[2,1,3]oxadiazol-4-yl). More preferred heteroaryl groups are furanyl (notably furan-2-yl), isoxazolyl (notably isoxazol-3-yl), thiazolyl (notably thiazol-2-yl), pyridyl (notably pyridin-2-yl and pyridin-3-yl), pyrazinyl (notably pyrazin-2-yl) and benzothiazolyl (notably benzothiazol-5-yl). Most preferred are isoxazolyl (notably isoxazol-3-yl) and pyridyl (notably pyridin-3-yl). The above-mentioned heteroaryl groups as used in $R^1$ are unsubstituted, mono-, di- or tri-substituted (preferably unsubstituted or mono-substituted), wherein the substituents are independently selected from the group consisting of halogen, $(C_1-C_4)$alkyl, $(C_1-C_4)$alkoxy, $(C_1-C_2)$fluoroalkyl and $(C_1-C_2)$fluoroalkoxy. Preferably the substituents are independently selected from the group consisting of halogen, $(C_1-C_4)$alkyl, and $(C_1-C_2)$fluoroalkyl. Most preferably the substituents are independently selected from halogen and methyl. Examples of such unsubstituted, mono-, di- or tri-substituted heteroaryl groups as used in $R^1$ are 5-methyl-isoxazol-3-yl and 6-bromo-pyridin-3-yl. A further example is 3-methyl-isoxazol-5-yl.

In case $R^2$ represents "$(C_1-C_6)$alkyl, which is mono-substituted with a heteroaryl group" the term "heteroaryl" means the above-mentioned groups. Preferred heteroaryl groups are furanyl (notably furan-3-yl), isoxazolyl (notably isoxazol-4-yl), thiazolyl (notably thiazol-4-yl), imidazolyl (notably imidazol-1-yl and imidazol-2-yl), pyrazolyl (notably pyrazol-1-yl, pyrazol-3-yl, pyrazol-4-yl and pyrazol-5-yl), triazolyl (notably [1,2,4]triazol-1-yl), pyridyl (notably pyridin-2-yl and pyridin-3-yl), indolyl (notably indol-3-yl) and benzimidazolyl (notably benzimidazol-2-yl). The above-mentioned heteroaryl groups are unsubstituted, mono-, di- or tri-substituted (preferably unsubstituted, mono- or disubstituted), wherein the substituents are independently selected from the group consisting of halogen, $(C_1-C_4)$alkyl, —$CH_2NH_2$ and —$SO_2NH_2$. Preferably the substituents are independently selected from the group consisting of $(C_1-C_4)$alkyl.

The term "heterocyclyl", used alone or in combination, means a 4- to 7-membered (notably 4- to 6-membered) saturated monocyclic ring containing 1 or 2 heteroatoms independently selected from the group consisting of sulfur, oxygen and nitrogen (preferably oxygen and nitrogen), wherein one or two methylene groups adjacent to a nitrogen atom are optionally replaced by carbonyl groups. Examples of such heterocyclyl groups are azetidinyl, oxetanyl, pyrrolidinyl, pyrrolidinonyl, tetrahydrofuranyl, tetrahydro-thiophenyl, imidazolidinonyl, oxazolidinyl, oxazolidinonyl, dioxolanyl, thiazolidinyl, thiazolidinonyl, piperidinyl, piperidonyl, piperazinyl, piperazinonyl, piperazine-dionyl, tetrahydro-2H-pyranyl, morpholinyl, morpholinonyl, thiomorpholinyl, thiomorpholinonyl, dioxanyl, 1,4-diazepanyl and 1,4-diazepanonyl. Preferred examples are azetidinyl, pyrrolidinyl, pyrrolidinonyl, tetrahydrofuranyl, imidazolidinonyl, piperidinyl, piperidonyl, piperazinyl, tetrahydro-2H-pyranyl, morpholinyl, dioxanyl and 1,4-diazepanyl. The heterocyclyl group may be unsubstituted or substituted as explicitly defined.

In case $R^2$ represents "$(C_3-C_6)$cycloalkyl, which is mono-substituted with heterocyclyl-methyl" the term "heterocyclyl" means the above-mentioned groups. Preferred heterocyclyl groups are azetidinyl (notably azetidin-1-yl), pyrrolidinyl (notably pyrrolidin-1-yl) and piperidinyl (notably piperidin-1-yl). Most preferred is pyrrolidinyl (notably pyrrolidin-1-yl).

In case $R^2$ represents "heterocyclyl" the term means the above-mentioned groups. Preferred heterocyclyl groups as used in $R^2$ are azetidinyl (notably azetidin-3-yl), pyrrolidinyl (notably pyrrolidin-3-yl), piperidinyl (notably piperidin-3-yl and piperidin-4-yl) and tetrahydro-2H-pyranyl (notably tetrahydro-2H-pyran-3-yl). Most preferred are pyrrolidin-3-yl, piperidin-3-yl and piperidin-4-yl. The above-mentioned heterocyclyl groups are unsubstituted, or mono-substituted at a nitrogen atom with $(C_1-C_4)$alkyl or benzyl, and/or independently mono- or di-substituted at one or two of the carbon atoms with substituents independently selected from halogen and $(C_1-C_4)$alkyl. Examples of such heterocyclyl groups are azetidin-3-yl, pyrrolidin-3-yl, 1-methyl-pyrrolidin-3-yl, piperidin-3-yl, piperidin-4-yl, 1-methyl-piperidin-4-yl and 1,2,2,6,6-pentamethyl-piperidin-4-yl. Further examples are 1-benzyl-piperidin-4-yl, 3-fluoro-piperidin-4-yl and 3,3-difluoro-piperidin-4-yl. In case $R^2$ represents "$(C_1-C_6)$alkyl, which is mono-substituted with heterocyclyl" the term "heterocyclyl" means the above-mentioned groups. Preferred heterocyclyl groups are azetidinyl (notably azetidin-1-yl), pyrrolidinyl (notably pyrrolidin-1-yl and pyrrolidin-2-yl), pyrrolidinonyl (notably pyrrolidin-2-on-1-yl), tetrahydrofuranyl (notably tetrahydrofuran-2-yl), imidazolidinonyl (notably imidazolidin-2-on-1-yl), 1,3-dioxolanyl (notably 1,3-dioxolan-4-yl), piperidinyl (notably piperidin-1-yl, piperidin-2-yl, piperidin-3-yl and piperidin-4-yl), piperazinyl (notably piperazin-1-yl), morpholinyl (notably morpholin-4-yl), dioxanyl (notably 1,4-dioxan-2-yl) and 1,4-diazepanyl (notably 1,4-diazepan-1-yl). More preferred are azetidinyl (notably azetidin-1-yl), pyrrolidinyl (notably pyrrolidin-1-yl and pyrrolidin-2-yl), tetrahydrofuranyl (notably tetrahydrofuran-2-yl), imidazolidinonyl (notably imidazolidin-2-on-1-yl), 1,3-dioxolanyl (notably 1,3-dioxolan-4-yl), piperidinyl (notably piperidin-1-yl, piperidin-2-yl, piperidin-3-yl and piperidin-4-yl), piperazinyl (notably piperazin-1-yl), morpholinyl (notably morpholin-4-yl) and 1,4-diazepanyl (notably 1,4-diazepan-1-yl). Even more preferred are pyrrolidinyl (notably pyrrolidin-1-yl), piperidinyl (notably piperidin-1-yl, piperidin-2-yl, piperidin-3-yl and piperidin-4-yl) and piperazinyl (notably piperazin-1-yl). Most preferred is piperidinyl (notably piperidin-2-yl, piperidin-3-yl and piperidin-4-yl). The above-mentioned heterocyclyl groups are unsubstituted, or mono-substituted at a nitrogen atom with $(C_1-C_4)$alkyl and/or independently mono- or di-substituted at one or two of the carbon atoms with substituents independently selected from halogen and $(C_1-C_4)$alkyl. Examples of such heterocyclyl groups are pyrrolidin-2-on-1-yl, 2,2-dimethyl-1,3-dioxolan-4-yl, piperidin-2-yl, 1-methyl-piperidin-2-yl, piperidin-3-yl and piperidin-4-yl. Further examples are pyrrolidin-1-yl, 3-fluoro-pyrrolidin-1-yl, 3-fluoro-piperidin-4-yl, 4-fluoro-piperidin-4-yl, 3,3-difluoro-piperidin-4-yl and piperazin-1-yl.

In case $R^2$ represents "$(C_2-C_6)$alkyl, which is mono-substituted with $(C_1-C_4)$alkoxy which is mono-substituted with heterocyclyl" the term "heterocyclyl" means the above-mentioned groups. Preferred heterocyclyl groups are azetidinyl (notably azetidin-1-yl), pyrrolidinyl (notably pyrrolidin-1-yl) and piperidinyl (notably piperidin-1-yl). Most preferred is pyrrolidin-1-yl. The above-mentioned heterocyclyl groups are unsubstituted, or mono-substituted at a nitrogen atom with $(C_1-C_4)$alkyl and/or independently mono- or di-substituted at one or two of the carbon atoms with substituents independently selected from halogen and $(C_1-C_4)$alkyl. Examples of such heterocyclyl groups are pyrrolidin-1-yl and 3-fluoro-pyrrolidin-1-yl (notably pyrrolidin-1-yl and (S)-3-fluoro-pyrrolidin-1-yl). A further example is 3,3-di-fluoro-pyrrolidin-1-yl.

In case $R^2$ represents "$(C_3-C_5)$fluoroalkyl, which is mono-substituted with heterocyclyl" the term "heterocyclyl" means the above-mentioned groups. Preferred heterocyclyl groups are azetidinyl (notably azetidin-1-yl), pyrrolidinyl (notably pyrrolidin-1-yl and pyrrolidin-2-yl), pyrrolidinonyl (notably pyrrolidin-2-on-1-yl), tetrahydrofuranyl (notably tetrahydrofuran-2-yl), imidazolidinonyl (notably imidazolidin-2-on-1-yl), piperidinyl (notably piperidin-1-yl, piperidin-3-yl and piperidin-4-yl), piperazinyl (notably piperazin-1-yl), morpholinyl (notably morpholin-4-yl), dioxanyl (notably 1,4-dioxan-2-yl) and 1,4-diazepanyl (notably 1,4-diazepan-1-yl). More preferred heterocyclyl groups are azetidinyl (notably azetidin-1-yl), pyrrolidinyl (notably pyrrolidin-1-yl) and piperidinyl (notably piperidin-1-yl). Most preferred is pyrrolidin-1-yl. The above-mentioned heterocyclyl groups are unsubstituted or independently mono- or di-substituted at one or two of the carbon atoms with substituents independently selected from halogen (notably fluoro) and $(C_1-C_4)$alkyl (notably methyl). An example is pyrrolidin-1-yl.

2) A further embodiment of the invention relates to bridged spiro[2.4]heptane ester derivatives according to embodiment 1), wherein W represents —CH$_2$CH$_2$— or —CH═CH— (preferably —CH$_2$CH$_2$—);

Y represents a bond or a methandiyl group;

$R^1$ represents an aryl- or a heteroaryl-group, which groups are independently unsubstituted, mono- or di-substituted (preferably mono- or di-substituted), wherein the substituents are independently selected from the group consisting of halogen, $(C_1-C_4)$alkyl, $(C_1-C_4)$alkoxy and $(C_1-C_2)$fluoroalkyl (preferably from fluoro, chloro, bromo, methyl, methoxy and trifluoromethyl);

$R^2$ represents $(C_3-C_6)$cycloalkyl, which is unsubstituted or mono-substituted with $R^3R^4N$—CH$_2$— or heterocyclyl-methyl; or $(C_2-C_6)$alkyl, which is
unsubstituted;
mono-substituted with —NR$^3$R$^4$, —C(O)NR$^5$R$^6$, $(C_1-C_4)$alkoxy, or $(C_1-C_4)$alkoxy which is mono-substituted with heterocyclyl, which heterocyclyl is unsubstituted, or mono-substituted at a nitrogen atom with ($C_1$-$C_4$)alkyl and/or independently mono- or di-substituted at one or two of the carbon atoms with substituents independently selected from halogen and ($C_1$-$C_4$)alkyl; or mono- or di-substituted with hydroxy; or ($C_1$-$C_6$)alkyl (preferably ($C_1$-$C_5$)alkyl), which is mono-substituted with heterocyclyl, which heterocyclyl is unsubstituted, or mono-substituted at a nitrogen atom with ($C_1$-$C_4$) alkyl and/or independently mono- or di-substituted at one or two of the carbon atoms with substituents independently selected from halogen and ($C_1$-$C_4$) alkyl; or with an aryl- or heteroaryl-group, which groups are independently unsubstituted, mono-, or di-substituted, wherein the substituents are independently selected from the group consisting of halogen, ($C_1$-$C_4$)alkyl, —$CH_2NH_2$ and —$SO_2NH_2$ (preferably from ($C_1$-$C_4$)alkyl and —$CH_2NH_2$); or ($C_3$-$C_5$)fluoroalkyl, which is mono-substituted with heterocyclyl, which heterocyclyl is unsubstituted or independently mono- or di-substituted at one or two of the carbon atoms with substituents independently selected from halogen and ($C_1$-$C_4$)alkyl; or heterocyclyl, which is unsubstituted, or mono-substituted at a nitrogen atom with ($C_1$-$C_4$)alkyl or benzyl, and/or independently mono- or di-substituted at one or two of the carbon atoms with substituents independently selected from halogen and ($C_1$-$C_4$)alkyl;

$R^3$ and $R^4$ represent independently from each other hydrogen or ($C_1$-$C_3$)alkyl; and $R^5$ and $R^6$ represent independently from each other hydrogen or methyl; or $R^5$ and $R^6$ form, together with the nitrogen that carries them, a pyrrolidine or piperidine ring;

and to the salts (in particular pharmaceutically acceptable salts) of such compounds.

3) A further embodiment of the invention relates to bridged spiro[2.4]heptane ester derivatives according to embodiment 1), wherein W represents —$CH_2CH_2$— or —CH=CH— (preferably —$CH_2CH_2$—);

Y represents a bond or a methandiyl group;

$R^1$ represents an aryl- or a heteroaryl-group, which groups are independently unsubstituted, mono- or di-substituted (preferably mono- or di-substituted), wherein the substituents are independently selected from the group consisting of halogen, ($C_1$-$C_4$)alkyl, ($C_1$-$C_4$)alkoxy and ($C_1$-$C_2$)fluoroalkyl (preferably from fluoro, chloro, bromo, methyl, methoxy and trifluoromethyl);

$R^2$ represents cyclopentyl or cyclohexyl, which are independently unsubstituted or mono-substituted with $R^3R^4N$—$CH_2$— or heterocyclyl-methyl; or ($C_2$-$C_6$)alkyl (preferably ($C_2$-$C_5$)alkyl), which is mono-substituted with —$NR^3R^4$, —$C(O)NR^5R^6$, or ($C_1$-$C_4$) alkoxy which is mono-substituted with heterocyclyl, which heterocyclyl is unsubstituted or mono- or di-substituted (preferably unsubstituted or mono-substituted) at one of the carbon atoms with fluoro; or ($C_1$-$C_6$)alkyl (preferably ($C_1$-$C_5$)alkyl), which is mono-substituted with heterocyclyl, which heterocyclyl is unsubstituted, or mono-substituted at a nitrogen atom with ($C_1$-$C_4$) alkyl (preferably methyl) and/or mono- or di-substituted at one of the carbon atoms with fluoro; or with an aryl- or heteroaryl-group, which groups are independently unsubstituted, mono-, or di-substituted (preferably mono-substituted), wherein the substituents are independently selected from the group consisting of ($C_1$-$C_4$)alkyl and —$CH_2NH_2$ (preferably —$CH_2NH_2$); or ($C_3$-$C_5$)fluoroalkyl, which is mono-substituted with heterocyclyl, which heterocyclyl is unsubstituted (preferred) or mono- or di-substituted at one of the carbon atoms with fluoro; or heterocyclyl, which is unsubstituted (preferred) or mono- or di-substituted at one of the carbon atoms with fluoro;

$R^3$ represents hydrogen or ($C_1$-$C_3$)alkyl (preferably hydrogen or methyl);

$R^4$ represents ($C_1$-$C_3$)alkyl (preferably methyl); and $R^5$ and $R^6$ represent independently from each other hydrogen or methyl; or $R^5$ and $R^6$ form, together with the nitrogen that carries them, a pyrrolidine or piperidine ring;

and to the salts (in particular pharmaceutically acceptable salts) of such compounds.

4) A further embodiment of the invention relates to bridged spiro[2.4]heptane ester derivatives according to any one of embodiments 1) to 3), wherein W represents —$CH_2CH_2$—;

and to the salts (in particular pharmaceutically acceptable salts) of such compounds.

5) A further embodiment of the invention relates to bridged spiro[2.4]heptane ester derivatives according to any one of embodiments 1) to 3), wherein W represents —CH=CH—;

and to the salts (in particular pharmaceutically acceptable salts) of such compounds.

6) A further embodiment of the invention relates to bridged spiro[2.4]heptane ester derivatives according to any one of embodiments 1) to 5), wherein Y represents a bond or a methandiyl group;

and to the salts (in particular pharmaceutically acceptable salts) of such compounds.

7) A further embodiment of the invention relates to bridged spiro[2.4]heptane ester derivatives according to any one of embodiments 1) to 5), wherein Y represents a bond;

and to the salts (in particular pharmaceutically acceptable salts) of such compounds.

8) A further embodiment of the invention relates to bridged spiro[2.4]heptane ester derivatives according to any one of embodiments 1) to 5), wherein Y represents a ($C_1$-$C_2$)alkandiyl group (preferably a methandiyl group);

and to the salts (in particular pharmaceutically acceptable salts) of such compounds.

9) A further embodiment of the invention relates to bridged spiro[2.4]heptane ester derivatives according to any one of embodiments 1) or 4) to 5), wherein Y represents a ethan-1,2-diyl group;

and to the salts (in particular pharmaceutically acceptable salts) of such compounds.

10) A further embodiment of the invention relates to bridged spiro[2.4]heptane ester derivatives according to any one of embodiments 1) to 9), wherein $R^1$ represents an aryl- or a heteroaryl-group, which groups are independently unsubstituted, mono- or di-substituted (preferably mono- or di-substituted), wherein the substituents are independently selected from the group consisting of halogen, $(C_1-C_4)$alkyl, $(C_1-C_4)$alkoxy and $(C_1-C_2)$fluoroalkyl (preferably from fluoro, chloro, bromo, methyl, methoxy and trifluoromethyl);

and to the salts (in particular pharmaceutically acceptable salts) of such compounds.

11) A further embodiment of the invention relates to bridged spiro[2.4]heptane ester derivatives according to any one of embodiments 1) to 9), wherein $R^1$ represents an aryl- or a heteroaryl-group, which groups are independently mono- or di-substituted, wherein the substituents are independently selected from the group consisting of halogen and $(C_1-C_4)$alkyl (preferably from bromo and methyl);

and to the salts (in particular pharmaceutically acceptable salts) of such compounds.

12) A further embodiment of the invention relates to bridged spiro[2.4]heptane ester derivatives according to any one of embodiments 1) to 9), wherein $R^1$ represents a phenyl group, which group is unsubstituted, mono- or di-substituted (preferably mono- or di-substituted), wherein the substituents are independently selected from the group consisting of halogen, $(C_1-C_4)$alkoxy and $(C_1-C_2)$fluoroalkyl (preferably from fluoro, bromo, methoxy and trifluoromethyl);

and to the salts (in particular pharmaceutically acceptable salts) of such compounds.

13) A further embodiment of the invention relates to bridged spiro[2.4]heptane ester derivatives according to any one of embodiments 1) to 9), wherein $R^1$ represents a heteroaryl-group, which group is unsubstituted, mono- or di-substituted (preferably mono-substituted), wherein the substituents are independently selected from the group consisting of halogen, $(C_1-C_4)$alkyl and $(C_1-C_2)$fluoroalkyl (preferably from chloro, bromo, methyl and trifluoromethyl);

and to the salts (in particular pharmaceutically acceptable salts) of such compounds.

14) A further embodiment of the invention relates to bridged spiro[2.4]heptane ester derivatives according to embodiment 13), wherein the heteroaryl-group is selected from isoxazolyl, thiazolyl, pyridyl and pyrazinyl;

and to the salts (in particular pharmaceutically acceptable salts) of such compounds.

15) A further embodiment of the invention relates to bridged spiro[2.4]heptane ester derivatives according to any one of embodiments 1), 2) or 4) to 14), wherein $R^2$ represents $(C_3-C_6)$cycloalkyl, which is unsubstituted or mono-substituted with $R^3R^4N$—$CH_2$— or heterocyclyl-methyl; or $(C_2-C_6)$alkyl, which is unsubstituted;

mono-substituted with —$NR^3R^4$, —$C(O)NR^5R^6$, $(C_1-C_4)$alkoxy, or $(C_1-C_4)$alkoxy which is mono-substituted with heterocyclyl, which heterocyclyl is unsubstituted, or mono-substituted at a nitrogen atom with $(C_1-C_4)$alkyl and/or independently mono- or di-substituted at one or two of the carbon atoms with substituents independently selected from halogen and $(C_1-C_4)$alkyl (preferably halogen); or mono- or di-substituted with hydroxy; or $(C_1-C_6)$alkyl (preferably $(C_1-C_5)$alkyl), which is mono-substituted with heterocyclyl, which heterocyclyl is unsubstituted, or mono-substituted at a nitrogen atom with $(C_1-C_4)$ alkyl and/or independently mono- or di-substituted at one or two of the carbon atoms with substituents independently selected from halogen and $(C_1-C_4)$ alkyl; or with an aryl- or heteroaryl-group, which groups are independently unsubstituted, mono-, or di-substituted, wherein the substituents are independently selected from the group consisting of halogen, $(C_1-C_4)$alkyl, —$CH_2NH_2$ and —$SO_2NH_2$ (preferably from $(C_1-C_4)$alkyl and —$CH_2NH_2$); or $(C_3-C_5)$fluoroalkyl, which is mono-substituted with heterocyclyl, which heterocyclyl is unsubstituted or independently mono- or di-substituted at one or two of the carbon atoms with substituents independently selected from halogen and $(C_1-C_4)$alkyl; or heterocyclyl, which is unsubstituted, or mono-substituted at a nitrogen atom with $(C_1-C_4)$alkyl or benzyl, and/or independently mono- or di-substituted at one or two of the carbon atoms with substituents independently selected from halogen and $(C_1-C_4)$alkyl;

and to the salts (in particular pharmaceutically acceptable salts) of such compounds.

16) A further embodiment of the invention relates to bridged spiro[2.4]heptane ester derivatives according to any one of embodiments 1) to 14), wherein $R^2$ represents cyclopentyl or cyclohexyl, which are independently unsubstituted or mono-substituted with $R^3R^4N$—$CH_2$— or heterocyclyl-methyl; or $(C_2-C_6)$alkyl (preferably $(C_2-C_5)$alkyl), which is mono-substituted with —$NR^3R^4$, —$C(O)NR^5R^6$, or $(C_1-C_4)$ alkoxy which is mono-substituted with heterocyclyl, which heterocyclyl is unsubstituted or mono- or di-substituted (preferably unsubstituted or mono-substituted) at one of the carbon atoms with fluoro; or $(C_1-C_6)$alkyl (preferably $(C_1-C_5)$alkyl), which is mono-substituted with heterocyclyl, which heterocyclyl is unsubstituted, or mono-substituted at a nitrogen atom with $(C_1-C_4)$ alkyl (preferably methyl) and/or mono- or di-substituted at one of the carbon atoms with fluoro; or with an aryl- or heteroaryl-group, which groups are independently unsubstituted, mono-, or di-substituted (preferably mono-substituted), wherein the substituents are independently selected from the group consisting of $(C_1-C_4)$alkyl and —$CH_2NH_2$ (preferably —$CH_2NH_2$); or $(C_3-C_5)$fluoroalkyl, which is mono-substituted with heterocyclyl, which heterocyclyl is unsubstituted (preferred) or mono- or di-substituted at one of the carbon atoms with fluoro; or heterocyclyl, which is unsubstituted (preferred) or mono- or di-substituted at one of the carbon atoms with fluoro;

and to the salts (in particular pharmaceutically acceptable salts) of such compounds.

17) A further embodiment of the invention relates to bridged spiro[2.4]heptane ester derivatives according to any one of embodiments 1) to 14), wherein $R^2$ represents cyclohexyl, which is mono-substituted with $R^3R^4N$—$CH_2$—; or $(C_2-C_6)$alkyl (preferably $(C_2-C_5)$alkyl), which is mono-substituted with —$NR^3R^4$, —$C(O)NR^5R^6$, or $(C_1-C_4)$ alkoxy which is mono-substituted with heterocyclyl, which heterocyclyl is unsubstituted or mono- or di-substituted (preferably unsubstituted or mono-substituted) at one of the carbon atoms with fluoro; or ($C_1$-$C_6$)alkyl (preferably ($C_1$-$C_5$)alkyl), which is mono-substituted with heterocyclyl, which heterocyclyl is unsubstituted, or mono-substituted at a nitrogen atom with methyl and/or mono- or di-substituted at one of the carbon atoms with fluoro; or ($C_3$-$C_5$)fluoroalkyl, which is mono-substituted with heterocyclyl, which heterocyclyl is unsubstituted (preferred) or mono- or di-substituted at one of the carbon atoms with fluoro; or heterocyclyl, which is unsubstituted;

and to the salts (in particular pharmaceutically acceptable salts) of such compounds.

18) A further embodiment of the invention relates to bridged spiro[2.4]heptane ester derivatives according to any one of embodiments 1), 2) or 4) to 14), wherein $R^2$ represents ($C_2$-$C_6$)alkyl (preferably ethyl or n-propyl), which is
  mono-substituted with ($C_1$-$C_4$)alkoxy (preferably methoxy); or
  di-substituted with hydroxy; or ($C_1$-$C_6$)alkyl (preferably methyl), which is mono-substituted with heterocyclyl, which heterocyclyl is unsubstituted, or mono- or di-substituted (preferably di-substituted) at one of the carbon atoms with ($C_1$-$C_4$)alkyl (preferably methyl); or heterocyclyl, which is unsubstituted, or mono-substituted at a nitrogen atom with ($C_1$-$C_4$)alkyl (preferably methyl) and/or independently mono- or di-substituted (preferably di-substituted) at one or two (preferably two) of the carbon atoms with ($C_1$-$C_4$)alkyl (preferably methyl);

and to the salts (in particular pharmaceutically acceptable salts) of such compounds.

19) A further embodiment of the invention relates to bridged spiro[2.4]heptane ester derivatives according to any one of embodiments 1) to 14), wherein $R^2$ represents ($C_3$-$C_6$)cycloalkyl (preferably cyclopentyl or cyclohexyl), which is unsubstituted or mono-substituted with $R^3R^4N$—$CH_2$— or heterocyclyl-methyl (preferably mono-substituted with $R^3R^4N$—$CH_2$— or heterocyclyl-methyl);

and to the salts (in particular pharmaceutically acceptable salts) of such compounds.

20) A further embodiment of the invention relates to bridged spiro[2.4]heptane ester derivatives according to any one of embodiments 1), 2) or 4) to 14), wherein $R^2$ represents ($C_2$-$C_6$)alkyl (preferably ($C_2$-$C_5$)alkyl), which is unsubstituted;

mono-substituted with —$NR^3R^4$, —$C(O)NR^5R^6$, ($C_1$-$C_4$)alkoxy, or ($C_1$-$C_4$)alkoxy which is mono-substituted with heterocyclyl, which heterocyclyl is unsubstituted, or mono-substituted at a nitrogen atom with ($C_1$-$C_4$)alkyl and/or independently mono- or di-substituted at one or two of the carbon atoms with substituents independently selected from halogen and ($C_1$-$C_4$)alkyl; or mono- or di-substituted with hydroxy; or and to the salts (in particular pharmaceutically acceptable salts) of such compounds.

21) A further embodiment of the invention relates to bridged spiro[2.4]heptane ester derivatives according to any one of embodiments 1) to 14), wherein $R^2$ represents ($C_2$-$C_6$)alkyl, which is mono-substituted with —$NR^3R^4$, —$C(O)NR^5R^6$, ($C_1$-$C_4$)alkoxy, or ($C_1$-$C_4$)alkoxy which is mono-substituted with heterocyclyl, which heterocyclyl is unsubstituted or mono- or di-substituted (preferably unsubstituted or mono-substituted) at one of the carbon atoms with fluoro; preferred is ($C_2$-$C_5$)alkyl, which is mono-substituted with —$NR^3R^4$, —$C(O)NR^5R^6$, or ($C_1$-$C_4$)alkoxy which is mono-substituted with heterocyclyl, which heterocyclyl is unsubstituted or mono-substituted at one of the carbon atoms with fluoro;

and to the salts (in particular pharmaceutically acceptable salts) of such compounds.

22) A further embodiment of the invention relates to bridged spiro[2.4]heptane ester derivatives according to any one of embodiments 1) or 4) to 14), wherein $R^2$ represents ($C_1$-$C_6$)alkyl (preferably ($C_1$-$C_5$)alkyl), which is mono-substituted with ($C_3$-$C_6$)cycloalkyl, which cycloalkyl is mono-substituted with —$NR^3R^4$;

with heterocyclyl, which heterocyclyl is unsubstituted, or mono-substituted at a nitrogen atom with ($C_1$-$C_4$)alkyl and/or independently mono- or di-substituted at one or two of the carbon atoms with substituents independently selected from halogen and ($C_1$-$C_4$)alkyl; or with an aryl- or heteroaryl-group, which groups are independently unsubstituted, mono-, di- or tri-substituted, wherein the substituents are independently selected from the group consisting of halogen, ($C_1$-$C_4$)alkyl, —$CH_2NH_2$ and —$SO_2NH_2$; and to the salts (in particular pharmaceutically acceptable salts) of such compounds.

23) A further embodiment of the invention relates to bridged spiro[2.4]heptane ester derivatives according to any one of embodiments 1), 2) or 4) to 14), wherein $R^2$ represents ($C_1$-$C_6$)alkyl (preferably ($C_1$-$C_5$)alkyl), which is mono-substituted with heterocyclyl, which heterocyclyl is unsubstituted, or mono-substituted at a nitrogen atom with ($C_1$-$C_4$)alkyl (preferably methyl) and/or independently mono- or di-substituted at one or two of the carbon atoms with substituents independently selected from halogen and ($C_1$-$C_4$)alkyl;

and to the salts (in particular pharmaceutically acceptable salts) of such compounds.

24) A further embodiment of the invention relates to bridged spiro[2.4]heptane ester derivatives according to any one of embodiments 1) to 14), wherein $R^2$ represents ($C_1$-$C_5$)alkyl, which is mono-substituted with heterocyclyl, which heterocyclyl is unsubstituted, or mono-substituted at a nitrogen atom with ($C_1$-$C_4$)alkyl (preferably methyl) and/or mono- or di-substituted at one of the carbon atoms with fluoro;

and to the salts (in particular pharmaceutically acceptable salts) of such compounds.

25) A further embodiment of the invention relates to bridged spiro[2.4]heptane ester derivatives according to any one of embodiments 1) to 14), wherein $R^2$ represents ($C_1$-$C_6$)alkyl (preferably ($C_1$-$C_5$)alkyl), which is mono-substituted with an aryl- or heteroaryl-group, which groups are independently unsubstituted, mono-, or di-substituted (preferably mono-substituted), wherein the substituents are independently selected from the group consisting of halogen, ($C_1$-$C_4$)alkyl, —$CH_2NH_2$ and —$SO_2NH_2$ (preferably from ($C_1$-$C_4$)alkyl and —$CH_2NH_2$);

and to the salts (in particular pharmaceutically acceptable salts) of such compounds.

26) A further embodiment of the invention relates to bridged spiro[2.4]heptane ester derivatives according to any one of embodiments 1), 2) or 4) to 14), wherein $R^2$ represents ($C_3$-$C_5$)fluoroalkyl, which is mono-substituted with heterocyclyl, which heterocyclyl is unsubstituted or independently mono- or di-substituted at one or two of the carbon atoms with substituents independently selected from halogen and ($C_1$-$C_4$)alkyl; and to the salts (in particular pharmaceutically acceptable salts) of such compounds.

27) A further embodiment of the invention relates to bridged spiro[2.4]heptane ester derivatives according to any one of embodiments 1) to 14), wherein R$^2$ represents (C$_3$-C$_5$)fluoroalkyl, which is mono-substituted with heterocyclyl, which heterocyclyl is unsubstituted (preferred) or mono- or di-substituted at one of the carbon atoms with fluoro;

and to the salts (in particular pharmaceutically acceptable salts) of such compounds.

28) A further embodiment of the invention relates to bridged spiro[2.4]heptane ester derivatives according to any one of embodiments 26) or 27), wherein (C$_3$-C$_5$)fluoroalkyl means 3-fluorobutyl (preferred) or 3,3-difluorobutyl;

and to the salts (in particular pharmaceutically acceptable salts) of such compounds.

29) A further embodiment of the invention relates to bridged spiro[2.4]heptane ester derivatives according to any one of embodiments 1), 2) or 4) to 14), wherein R$^2$ represents heterocyclyl, which is unsubstituted, or mono-substituted at a nitrogen atom with (C$_1$-C$_4$)alkyl or benzyl, and/or independently mono- or di-substituted at one or two of the carbon atoms with substituents independently selected from halogen and (C$_1$-C$_4$)alkyl;

and to the salts (in particular pharmaceutically acceptable salts) of such compounds.

30) A further embodiment of the invention relates to bridged spiro[2.4]heptane ester derivatives according to any one of embodiments 1) to 14), wherein R$^2$ represents heterocyclyl, which is unsubstituted (preferred) or mono- or di-substituted at one of the carbon atoms with fluoro;

and to the salts (in particular pharmaceutically acceptable salts) of such compounds.

31) A further embodiment of the invention relates to bridged spiro[2.4]heptane ester derivatives according to any one of embodiments 1) to 30), wherein R$^3$ represents hydrogen or (C$_1$-C$_3$)alkyl (preferably hydrogen or methyl);

and to the salts (in particular pharmaceutically acceptable salts) of such compounds.

32) A further embodiment of the invention relates to bridged spiro[2.4]heptane ester derivatives according to any one of embodiments 1) to 31), wherein R$^4$ represents (C$_1$-C$_3$)alkyl (preferably methyl);

and to the salts (in particular pharmaceutically acceptable salts) of such compounds.

33) A further embodiment of the invention relates to bridged spiro[2.4]heptane ester derivatives according to any one of embodiments 1) to 32), wherein R$^5$ and R$^6$ represent independently from each other hydrogen or methyl;

and to the salts (in particular pharmaceutically acceptable salts) of such compounds.

34) A further embodiment of the invention relates to bridged spiro[2.4]heptane ester derivatives according to any one of embodiments 1) to 32), wherein R$^5$ and R$^6$ form, together with the nitrogen that carries them, a pyrrolidine or piperidine ring; and to the salts (in particular pharmaceutically acceptable salts) of such compounds.

35) A further embodiment of the invention relates to bridged spiro[2.4]heptane ester derivatives according to any one of embodiments 1) to 34), wherein the term "heterocyclyl" means pyrrolidinyl or piperidinyl (preferably piperidinyl);

and to the salts (in particular pharmaceutically acceptable salts) of such compounds.

36) A further embodiment of the invention relates to bridged spiro[2.4]heptane ester derivatives according to any one of embodiments 1) to 35), wherein the absolute configuration of the stereogenic centers is as depicted in formula I$_{St1}$ above;

and to the salts (in particular pharmaceutically acceptable salts) of such compounds.

37) A further embodiment of the invention relates to bridged spiro[2.4]heptane ester derivatives according to any one of embodiments 1) to 35), wherein the absolute configuration of the stereogenic centers is as depicted in formula I$_{St2}$ above;

and to the salts (in particular pharmaceutically acceptable salts) of such compounds.

38) A further embodiment of the invention relates to bridged spiro[2.4]heptane ester derivatives according to any one of embodiments 1), 2), 4) to 15), 20) or 31) to 37), wherein R$^2$ is different from unsubstituted (C$_2$-C$_6$)alkyl;

and to the salts (in particular pharmaceutically acceptable salts) of such compounds.

39) A further embodiment of the invention relates to bridged spiro[2.4]heptane ester derivatives according to any one of embodiments 1), 2), 4) to 15), 20) or 31) to 37), with the exception of the following compounds:

(5R*)—N$^5$-(4-bromo-phenyl)-(6R*)-6-ethoxycarbonyl-(4S*,7R*)-[4,7-ethenylene-spiro[2.4]heptane]-5-carboxamide;

(5R*)—N$^5$-(4-bromo-phenyl)-(6R*)-6-ethoxycarbonyl-(4S*,7R*)-[4,7-ethylene-spiro[2.4]heptane]-5-carboxamide;

(5R*)—N$^5$-(5-methyl-thiazol-2-yl)-(6R*)-6-ethoxycarbonyl-(4S*,7R*)-[4,7-ethenylene-spiro[2.4]heptane]-5-carboxamide;

(5R*)—N$^5$-(4-bromophenyl-methyl)-(6R*)-6-ethoxycarbonyl-(4S*,7R*)-[4,7-ethenylene-spiro[2.4]heptane]-5-carboxamide;

(5R*)—N$^5$-(5-bromo-thiazol-2-yl)-(6R*)-6-ethoxycarbonyl-(4S*,7R*)-[4,7-ethenylene-spiro[2.4]heptane]-5-carboxamide;

(5R*)—N$^5$-(4-methyl-oxazol-2-yl)-(6R*)-6-ethoxycarbonyl-(4S*,7R*)-[4,7-ethenylene-spiro[2.4]heptane]-5-carboxamide;

(5R*)—N$^5$-(4,5-dimethyl-thiazol-2-yl)-(6R*)-6-ethoxycarbonyl-(4S*,7R*)-[4,7-ethenylene-spiro[2.4]heptane]-5-carboxamide; and (5R)—N$^5$-(4-bromo-phenyl)-(6R)-6-ethoxycarbonyl-(4S,7R)-[4,7-ethenylene-spiro[2.4]heptane]-5-carboxamide.

40) Preferred compounds of formula (I) as defined in embodiment 1) are selected from the group consisting of:

(1S,2R,3R,4R)-[Piperidin-4-ylmethyl 2-((6-bromopyridin-3-yl)carbamoyl)spiro[bicyclo[2.2.1]heptane-7,1'-cyclopropane]-3-carboxylate];

(1S,2R,3R,4R)-[Piperidin-4-yl 2-((6-bromopyridin-3-yl)carbamoyl)spiro[bicyclo[2.2.1]heptane-7,1'-cyclopropane]-3-carboxylate];

(1S,2R,3R,4R)-[Piperidin-4-ylmethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Piperidin-4-ylmethyl 2-((4-bromo-2-fluorobenzyl)carbamoyl)spiro[bicyclo[2.2.1]heptane-7,1'-cyclopropane]-3-carboxylate];

(1S,2R,3R,4R)-[(S*)-2,3-Dihydroxypropyl 2-((6-bromopyridin-3-yl)carbamoyl)spiro[bicyclo[2.2.1]heptane-7,1'-cyclopropane]-3-carboxylate];

(1S,2R,3R,4R)-[1-Methylpiperidin-4-yl 2-((6-bromopyridin-3-yl)carbamoyl)spiro[bicyclo[2.2.1]heptane-7,1'-cyclopropane]-3-carboxylate];

(1S,2R,3R,4R)-[2-Methoxyethyl 2-((6-bromopyridin-3-yl)carbamoyl)spiro[bicyclo[2.2.1]heptane-7,1'-cyclopropane]-3-carboxylate];

(1S,2R,3R,4R)-[1,2,2,6,6-Pentamethylpiperidin-4-yl 2-((6-bromopyridin-3-yl)carbamoyl)spiro[bicyclo[2.2.1]heptane-7,1'-cyclopropane]-3-carboxylate];

(1S,2R,3R,4R)-[Piperidin-3-yl 2-((6-bromopyridin-3-yl)carbamoyl)spiro[bicyclo[2.2.1]heptane-7,1'-cyclopropane]-3-carboxylate];

(1S,2R,3R,4R)-[2-(Piperidin-3-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[(S)-2-(Piperidin-2-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[Piperidin-3-ylmethyl 2-((6-bromopyridin-3-yl)carbamoyl)spiro[bicyclo[2.2.1]heptane-7,1'-cyclopropane]-3-carboxylate];

(1S,2R,3R,4R)-[(R)-Pyrrolidin-3-yl 2-((6-bromopyridin-3-yl)carbamoyl)spiro[bicyclo[2.2.1]heptane-7,1'-cyclopropane]-3-carboxylate];

(1S,2R,3R,4R)-[1-Methylpyrrolidin-3-yl 2-((6-bromopyridin-3-yl)carbamoyl)spiro[bicyclo[2.2.1]heptane-7,1'-cyclopropane]-3-carboxylate];

(1S,2R,3R,4R)-[1-Methylpyrrolidin-3-yl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Piperidin-3-yl 2-(((5-methylisoxazol-3-yl)methyl)carbamoyl)spiro[bicyclo[2.2.1]heptane-7,1'-cyclopropane]-3-carboxylate];

(1S,2R,3R,4R)-[2-(Piperidin-3-yl)ethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Piperidin-3-ylmethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[(R)-Pyrrolidin-3-yl 2-(((5-methylisoxazol-3-yl)methyl)carbamoyl)spiro[bicyclo[2.2.1]heptane-7,1'-cyclopropane]-3-carboxylate];

(1S,2R,3R,4R)-[(S)-2-(Piperidin-2-yl)ethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[1-Dimethylaminoprop-3-yl 2-((6-bromopyridin-3-yl)carbamoyl)spiro[bicyclo[2.2.1]heptane-7,1'-cyclopropane]-3-carboxylate];

(1S,2R,3R,4R)-[1-Methyl-piperidin-2-ylmethyl 2-((6-bromopyridin-3-yl)carbamoyl)spiro[bicyclo[2.2.1]heptane-7,1'-cyclopropane]-3-carboxylate];

(1S,2R,3R,4R)-[2-(2-oxopyrrolidin-1-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[Azetidin-3-yl 2-((6-bromopyridin-3-yl)carbamoyl)spiro[bicyclo[2.2.1]heptane-7,1'-cyclopropane]-3-carboxylate];

(1S,2R,3R,4R)-[1-Dimethylaminoprop-3-yl 2-(((5-methylisoxazol-3-yl)methyl)carbamoyl)spiro[bicyclo[2.2.1]heptane-7,1'-cyclopropane]-3-carboxylate];

(1S,2R,3R,4R)-[1-Methyl-piperidin-2-ylmethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[1-Dimethylaminoeth-2-yl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Isobutyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Cyclopentyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Propyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[2-(2-(Pyrrolidin-1-yl)ethoxy)ethyl 2-((6-bromopyridin-3-yl)carbamoyl)spiro[bicyclo[2.2.1]heptane-7,1'-cyclopropane]-3-carboxylate];

(1S,2R,3R,4R)-[2-(2-(Pyrrolidin-1-yl)ethoxy)ethyl 2-((4-bromo-2-fluorobenzyl)carbamoyl)spiro[bicyclo[2.2.1]heptane-7,1'-cyclopropane]-3-carboxylate];

(1S,2R,3R,4R)-[2-(2-(Pyrrolidin-1-yl)ethoxy)ethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[(S)-2-(2-(3-Fluoropyrrolidin-1-yl)ethoxy)ethyl 2-(((5-methylisoxazol-3-yl)methyl)carbamoyl)spiro[bicyclo[2.2.1]heptane-7,1'-cyclopropane]-3-carboxylate]; and (1R,4S,5R,6R)-[Piperidin-4-ylmethyl 5-((4-bromophenyl)carbamoyl)spiro[bicyclo[2.2.1]hept[2]ene-7,1'-cyclopropane]-6-carboxylate];

or salts (in particular pharmaceutically acceptable salts) of such compounds;

it is to be understood for any of the above listed compounds, that a stereogenic center, which is not specifically assigned, may be in absolute (R)- or absolute (S)-configuration and that a double bond, which is not specifically assigned, may be in (E)- or (Z)-configuration.

41) Further preferred compounds of formula (I) as defined in embodiment 1) are selected from the group consisting of:

(1S,2R,3R,4R)-[2-(Piperidin-4-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[2-(piperazin-1-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[2-(cis-3-Fluoro-piperidin-4-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[2-(cis-3-Fluoro-piperidin-4-yl)ethyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[2-(4-Fluoro-piperidin-4-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[(Piperidin-4-yl)methyl 2-((6-bromopyridin-3-yl)carbamoyl)spiro[bicyclo[2.2.1]heptane-7,1'-cyclopropane]-3-carboxylate];

(1S,2R,3R,4R)-[(S)-2-(2-(3-Fluoropyrrolidin-1-yl)ethoxy)ethyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[(trans-3-Fluoro-piperidin-4-yl)methyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[(cis-3-Fluoro-piperidin-4-yl)methyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[3-(Aminomethyl)benzyl 2-((6-bromopyridin-3-yl)carbamoyl)spiro[bicyclo[2.2.1]heptane-7,1'-cyclopropane]-3-carboxylate];

(1S,2R,3R,4R)-[(trans-3-Fluoro-piperidin-4-yl) 2-(((3-methylisoxazol-5-yl)methyl)carbamoyl)spiro[bicyclo[2.2.1]heptane-7,1'-cyclopropane]-3-carboxylate];

(1S,2R,3R,4R)-[2-(Piperidin-4-yl)ethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[(S)-2-(2-(3-Fluoropyrrolidin-1-yl)ethoxy) ethyl 2-((6-bromopyridin-3-yl)carbamoyl)spiro[bicyclo[2.2.1]heptane-7,1'-cyclopropane]-3-carboxylate];

(1S,2R,3R,4R)-[2-(4-Fluoro-piperidin-4-yl)ethyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[(Piperidin-4-yl)methyl 2-((4-bromophenyl)carbamoyl)spiro[bicyclo[2.2.1]heptane-7,1'-cyclopropane]-3-carboxylate];

(1S,2R,3R,4R)-[(4-Fluoro-piperidin-4-yl)methyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[(Piperidin-4-yl)methyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[(S)-4-(3-Fluoropyrrolidin-1-yl)butyl 2-((6-bromopyridin-3-yl)carbamoyl)spiro[bicyclo[2.2.1]heptane-7,1'-cyclopropane]-3-carboxylate];

(1S,2R,3R,4R)-[4-(Pyrrolidin-1-yl)butyl 2-((6-bromopyridin-3-yl)carbamoyl)spiro[bicyclo[2.2.1]heptane-7,1'-cyclopropane]-3-carboxylate];

(1S,2R,3R,4R)-[(4-Fluoro-piperidin-4-yl)methyl 2-((6-bromopyridin-3-yl)carbamoyl)spiro[bicyclo[2.2.1]heptane-7,1'-cyclopropane]-3-carboxylate];

(1S,2R,3R,4R)-[(3,3-Difluoro-piperidin-4-yl) 2-((6-bromopyridin-3-yl)carbamoyl)spiro[bicyclo[2.2.1]heptane-7,1'-cyclopropane]-3-carboxylate];

(1S,2R,3R,4R)-[(trans-3-Fluoro-piperidin-4-yl) 2-((6-bromopyridin-3-yl)carbamoyl)spiro[bicyclo[2.2.1]heptane-7,1'-cyclopropane]-3-carboxylate];

(1S,2R,3R,4R)-[2-(4-Fluoro-piperidin-4-yl)ethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[(4-Fluoro-piperidin-4-yl)methyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Piperidin-4-yl 2-((4-bromo-2-fluorobenzyl)carbamoyl)spiro[bicyclo[2.2.1]heptane-7,1'-cyclopropane]-3-carboxylate];

(1S,2R,3R,4R)-[(3,3-Difluoro-piperidin-4-yl) 2-(((3-methylisoxazol-5-yl)methyl)carbamoyl)spiro[bicyclo[2.2.1]heptane-7,1'-cyclopropane]-3-carboxylate];

(1S,2R,3R,4R)-[cis-(3-Fluoro-piperidin-4-yl) 2-(((3-methylisoxazol-5-yl)methyl)carbamoyl)spiro[bicyclo[2.2.1]heptane-7,1'-cyclopropane]-3-carboxylate];

(1S,2R,3R,4R)-[2-(piperazin-1-yl)ethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[(cis-3-Fluoro-piperidin-4-yl)methyl 2-((6-bromopyridin-3-yl)carbamoyl)spiro[bicyclo[2.2.1]heptane-7,1'-cyclopropane]-3-carboxylate];

(1S,2R,3R,4R)-[(3-Amino-3-oxopropyl) 2-(((3-methylisoxazol-5-yl)methyl)carbamoyl)spiro[bicyclo[2.2.1]heptane-7,1'-cyclopropane]-3-carboxylate];

(1S,2R,3R,4R)-[(3,3-Difluoro-piperidin-4-yl)ethyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[(4-Pyrrolidino-4-oxobutyl) 2-((6-bromopyridin-3-yl)carbamoyl)spiro[bicyclo[2.2.1]heptane-7,1'-cyclopropane]-3-carboxylate];

(1S,2R,3R,4R)-[(3-Amino-3-oxopropyl) 2-((6-bromopyridin-3-yl)carbamoyl)spiro[bicyclo[2.2.1]heptane-7,1'-cyclopropane]-3-carboxylate];

(1S,2R,3R,4R)-[(S)-2-(2-(3-Fluoropyrrolidin-1-yl)ethoxy) ethyl 2-((4-bromo-2-fluorobenzyl)carbamoyl)spiro[bicyclo[2.2.1]heptane-7,1'-cyclopropane]-3-carboxylate];

(1S,2R,3R,4R)-[(trans-3-Fluoro-piperidin-4-yl)methyl 2-((6-bromopyridin-3-yl)carbamoyl)spiro[bicyclo[2.2.1]heptane-7,1'-cyclopropane]-3-carboxylate];

(1S,2R,3R,4R)-[2-(piperazin-1-yl)ethyl 2-((4-bromo-2-fluorobenzyl)carbamoyl)spiro[bicyclo[2.2.1]heptane-7,1'-cyclopropane]-3-carboxylate];

(1S,2R,3R,4R)-[2-(Piperidin-4-yl)ethyl 2-((4-bromo-2-fluorobenzyl)carbamoyl)spiro[bicyclo[2.2.1]heptane-7,1'-cyclopropane]-3-carboxylate];

(1S,2R,3R,4R)-[2-(3,3-Difluoro-piperidin-4-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[cis-3-Fluoro-piperidin-4-yl 2-((6-bromopyridin-3-yl)carbamoyl)spiro[bicyclo[2.2.1]heptane-7,1'-cyclopropane]-3-carboxylate];

(1S,2R,3R,4R)-[2-(2-(3,3-Difluoropyrrolidin-1-yl)ethoxy) ethyl 2-((6-bromopyridin-3-yl)carbamoyl)spiro[bicyclo[2.2.1]heptane-7,1'-cyclopropane]-3-carboxylate];

(1S,2R,3R,4R)-[1-Benzyl-piperidin-4-yl 2-((6-bromopyridin-3-yl)carbamoyl)spiro[bicyclo[2.2.1]heptane-7,1'-cyclopropane]-3-carboxylate];

(1S,2R,3R,4R)-[(4,4-Difluoro-5-(pyrrolidin-1-yl))pent-2-yl 2-((6-bromopyridin-3-yl)carbamoyl)spiro[bicyclo[2.2.1]heptane-7,1'-cyclopropane]-3-carboxylate];

(1S,2R,3R,4R)-[(4,4-Difluoro-5-(pyrrolidin-1-yl))pent-1-yl 2-((6-bromopyridin-3-yl)carbamoyl)spiro[bicyclo[2.2.1]heptane-7,1'-cyclopropane]-3-carboxylate];

or salts (in particular pharmaceutically acceptable salts) of such compounds;

it is to be understood for any of the above listed compounds, that a stereogenic center, which is not specifically assigned, may be in absolute (R)— or absolute (S)-configuration and that a double bond, which is not specifically assigned, may be in (E)- or (Z)-configuration.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to any one of embodiments 1) to 41), or pharmaceutically acceptable salts thereof, are suitable for use as medicaments. In particular, compounds of formula (I) modulate the ALX receptor and/or FPRL2, i.e. they act as ALX receptor agonists and/or as FPRL2 agonists, and are useful for the prevention or treatment of diseases which respond to the activation of the ALX receptor and/or FPRL2 such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the modulation of immune responses (especially those elicited by vaccination). Especially, compounds of formula (I) are useful for the prevention or treatment of diseases such as inflammatory diseases, obstructive airway diseases, allergic conditions, cardiovascular disorders, neuroinflammation, neurological disorders, pain, prion-mediated diseases and amyloid-mediated disorders (especially Alzheimer's disease).

In particular, the compounds of formula (I) according to any one of embodiments 1) to 41), or pharmaceutically acceptable salts thereof, are suitable for the prevention or treatment of diseases selected from inflammatory diseases, obstructive airway diseases and allergic conditions.

Inflammatory diseases, obstructive airway diseases and allergic conditions include, but are not limited to, one, several or all of the following groups of diseases and disorders:

1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.

2) Further inflammatory diseases, obstructive airway diseases and allergic conditions include bronchitis of whatever type or genesis.

3) Further inflammatory diseases, obstructive airway diseases and allergic conditions include bronchiectasis, and pneumoconiosis of whatever type or genesis.

4) Further inflammatory diseases, obstructive airway diseases and allergic conditions include asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection.

5) In a further embodiment the compounds of formula (I) according to any one of embodiments 1) to 41), or pharmaceutically acceptable salts thereof, are particularly suitable for the prevention or treatment of inflammatory diseases. Inflammatory diseases include one, several or all of the following groups of diseases and disorders:

5a) In particular, inflammatory diseases refer to neutrophil related disorders, especially neutrophil related disorders of the airway including hyper-neutrophilia as it affects the airway and/or lungs. Further neutrophil related disorders also include periodontitis, glomerulonephritis, and cystic fibrosis.

5b) Further inflammatory diseases include skin diseases such as psoriasis, contact dermatitis, atopic dermatitis, dermatitis herpetiformis, scleroderma, hypersensitivity angiitis, urticaria, lupus erythematosus, and epidermolysis.

5c) Further inflammatory diseases also relate to diseases or conditions having an inflammatory component. Diseases or conditions having an inflammatory component include, but are not limited to, diseases and conditions affecting the eye such as uveitis (anterior, intermediate and posterior), Behget syndrome uveitis, conjunctivitis, keratoconjunctivitis sicca, Sjögren syndrome keratoconjunctivitis sicca, and vernal conjunctivitis (and especially conjunctivitis, keratoconjunctivitis sicca, and vernal conjunctivitis); diseases affecting the nose including rhinitis and allergic rhinitis (and especially allergic rhinitis); and inflammatory diseases in which autoimmune reactions are implicated or which have an autoimmune component or aetiology, such as systemic lupus erythematosus, ankylosing spondylitis, Behçet syndrome, Sjögren syndrome, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis (and especially systemic lupus erythematosus, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis).

5d) Further inflammatory diseases in which autoimmune reactions are implicated or which have an autoimmune component or aetiology include rheumatoid arthritis, Hashimoto's thyroid and diabetes type I or II.

Further, the compounds of formula (I) according to any one of embodiments 1) to 41), or pharmaceutically acceptable salts thereof, are suitable for the prevention or treatment of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation, particularly in the treatment of acute or chronic allo- and xenograft rejection or in the transplantation of insulin producing cells, e g pancreatic islet cells.

Further, the compounds of formula (I) according to any one of embodiments 1) to 41), or pharmaceutically acceptable salts thereof, are suitable for the prevention or treatment of HIV-mediated retroviral infections.

HIV-mediated retroviral infections include, but are not limited to, one, several or all of the groups of diseases and disorders caused by HIV-1 and HIV-2 strains such as GUN-4-v, GUN-7 wt, AG204, AG206, AG208, HCM305, HCM308, HCM342, mSTD104, and HCM309.

Further, the compounds of formula (I) according to any one of embodiments 1) to 41), or pharmaceutically acceptable salts thereof, are suitable for the prevention or treatment of cardiovascular disorders.

Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Further, the compounds of formula (I) according to any one of embodiments 1) to 41), or pharmaceutically acceptable salts thereof, are suitable for the prevention or treatment of neuroinflammation. Neuroinflammation refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Further, the compounds of formula (I) according to any one of embodiments 1) to 41), or pharmaceutically acceptable salts thereof, are suitable for the prevention or treatment of neurological disorders.

In particular, neurological disorders include, but are not limited to, epilepsy, stroke, cerebral ischemia, cerebral palsy, relapsing remitting multiple sclerosis, progressive multiple sclerosis, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea (and especially epilepsy, stroke, cerebral ischemia, cerebral palsy, relapsing remitting multiple sclerosis, progressive multiple sclerosis, Alpers' disease, amyotrophic lateral sclerosis (ALS), senile dementia, dementia with Lewy bodies, Rett syndrome, spinal cord trauma, traumatic brain injury, trigeminal neuralgia, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea).

Further, the compounds of formula (I) according to any one of embodiments 1) to 41), or pharmaceutically acceptable salts thereof, are suitable for the prevention or treatment of pain. Pain includes, but is not limited to, neuropathic pain exemplified by conditions such as diabetic neuropathy, postherpetic neuralgia, trigeminal neuralgia, painful diabetic polyneuropathy, post-stroke pain, post-amputation pain, myelopathic or radiculopathic pain, atypical facial pain and causalgia-like syndromes.

Further, the compounds of formula (I) according to any one of embodiments 1) to 41), or pharmaceutically acceptable salts thereof, are suitable for the prevention or treatment of prion-mediated diseases. Prion-mediated diseases, also known as transmissible spongiform encephalopathies (TSEs), include, but are not limited to, kuru, Gerstmann-Sträussler-Scheinker syndrome (GSS), Fatal Familial Insomnia (FFI) and Creutzfeldt-Jakob Disease (CJD).

Further, the compounds of formula (I) according to any one of embodiments 1) to 41), or pharmaceutically acceptable salts thereof, are suitable for the treatment of amyloid-mediated disorders. Amyloid-mediated disorders are defined as diseases and disorders, that are caused by or associated with amyloid or amyloid-like proteins. Diseases and disorders caused by or associated with amyloid or amyloid-like proteins include, but are not limited to, Alzheimer's Disease (AD), including diseases or conditions characterized by a loss of cognitive memory capacity such as, for example, mild cognitive impairment (MCI); dementia with Lewy bodies; Down's syndrome; cerebral hemorrhage with amyloidosis. In another embodiment, diseases and disorders caused by or associated with amyloid or amyloid-like proteins include progressive supranuclear palsy, amyloid light chain amyloidosis, familial amyloid neuropathies, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis (and especially progressive supranuclear palsy, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis).

Further, the compounds of formula (I) according to any one of embodiments 1) to 41), or pharmaceutically acceptable salts thereof, are suitable for the modulation of immune responses.

The modulation of immune responses includes, but is not limited to, methods based on the administration to a subject a composition of at least one antigen and at least one compound of formula (I) according to any one of embodiments 1) to 41), or pharmaceutically acceptable salts thereof. In some cases, the antigen-containing composition is administrated first, followed by administration of a composition of at least one compounds of formula (I) according to any one of embodiments 1) to 41), or pharmaceutically acceptable salts thereof. In other cases, the antigen-containing composition is administrated last. The different compositions may be administrated simultaneously, closely in sequence, or separated in time. Those methods and compositions are provided for therapeutic and prophylactic immunisation (i.e., the deliberate provocation, enhancement, intensification or modulation of an adaptative and/or innate immune response). Particular advantages may include one or more of the following:

1) An accelerated immune response following administration of at least one compound of formula (I) according to any one of embodiments 1) to 41), or pharmaceutically acceptable salts thereof, and the antigen, as compared to sole administration of the antigen;

2) A greater sensitivity to small amounts of antigen (e.g., toxin or pathogen) or antigens that do not habitually induce strong immune responses; and 3) More effective anti-tumor therapies.

Further, the compounds of formula (I) according to any one of embodiments 1) to 41), or pharmaceutically acceptable salts thereof, are suitable for the prevention or treatment of cystic fibrosis, pulmonary fibrosis, pulmonary hypertension, wound healing, diabetic nephropathy, reduction of inflammation in transplanted tissue, inflammatory diseases caused by pathogenic organisms.

Especially, compounds of formula (I) according to any one of embodiments 1) to 41), or pharmaceutically acceptable salts thereof, are suitable for the prevention or treatment of diseases selected from one, several or all of the following groups of diseases and disorders:

1) Inflammatory diseases, obstructive airway diseases and allergic conditions such as acute lung injury (ALI); adult/acute respiratory distress syndrome (ARDS); chronic obstructive pulmonary, airway or lung disease (COPD, COAD or COLD), including chronic bronchitis or dyspnea associated therewith; and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection (and especially acute lung injury (ALI); adult/acute respiratory distress syndrome (ARDS); and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection);

2) Inflammatory diseases such as neutrophil related disorders, especially neutrophil related disorders of the airway including hyper-neutrophilia as it affects the airway and/or lungs; periodontitis; glomerulonephritis; cystic fibrosis; and skin diseases such as psoriasis, contact dermatitis, atopic dermatitis, dermatitis herpetiformis, scleroderma, hypersensitivity angiitis, urticaria, lupus erythematosus, and epidermolysis;

3) Diseases having an inflammatory component such as diseases and conditions affecting the eye such as conjunctivitis, keratoconjunctivitis sicca, and vernal conjunctivitis; inflammatory disease in which autoimmune reactions are implicated or which have an autoimmune component or aetiology; and autoimmune inflammatory bowel disease (e.g. ulcerative colitis and Crohn's disease);

4) HIV-mediated retroviral infections such as diseases and disorders caused by HIV-1 and HIV-2 strains such as GUN-4-v, GUN-7 wt, AG204, AG206, AG208, HCM305, HCM308, HCM342, mSTD104, and HCM309;

5) Neuroinflammation which refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as amyloid β deposition of amyloid plaques;

6) Neurological disorders such as stroke, cerebral ischemia, Alzheimer's disease, and Parkinson's disease;

7) Prion-mediated diseases, also known as transmissible spongiform encephalopathies (TSEs), such as kuru, Gerstmann-Sträussler-Scheinker syndrome (GSS), Fatal Familial Insomnia (FFI) and Creutzfeldt-Jakob Disease (CJD);

8) Amyloid-mediated disorders;

9) Cystic fibrosis, wound healing and inflammatory diseases caused by pathogenic organisms.

The invention also relates to the use of a compound of formula (I) according to any one of embodiments 1) to 41) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 41).

A pharmaceutical composition according to the present invention contains at least one compound of formula (I) according to any one of embodiments 1) to 41) (or a pharmaceutically acceptable salt thereof) as the active agent and optionally carriers and/or diluents and/or adjuvants.

The compounds of formula (I) according to any one of embodiments 1) to 41) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 41), or a pharmaceutically acceptable salt thereof.

Any reference to a compound of formula I, $I_{ST1}$ or $I_{ST2}$ in this text is to be understood as referring also to the salts (and especially the pharmaceutically acceptable salts) of such compounds, as appropriate and expedient. The preferences indicated for the compounds of formula I of course apply mutatis mutandis to the compounds of formula $I_{ST1}$ and the compounds of formula $I_{ST2}$ as well as to the salts and pharmaceutically acceptable salts of the compounds of formula I, of formula $I_{ST1}$ or of formula $I_{ST2}$. The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5°

C. Besides, the term "room temperature" (rt) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups $R^1$, $R^2$, $R^3$, $R^4$, $R^5$, $R^6$, W and Y are as defined for formula (I). Other abbreviations used are defined in the experimental section.

Reactions of alcohols with methanesulfonyl chloride may result in the formation of the respective chloride or the respective mesylate derivative depending on the reaction conditions used; it is well known in the art that already small changes in such reaction conditions may have an influence on the outcome of said reactions; it should be understood that normally both reagents, the chloride and the mesylate, might be useful as electrophiles in reactions discussed below.

In some instances the generic groups $R^1$, $R^2$, $R^3$, $R^4$, $R^5$, $R^6$, W and Y might be incompatible with the assembly illustrated in the schemes below and will therefore require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups are as necessary in place.

A. Synthesis of Final Products

Sections A.a) to A.e) hereafter describe general methods for preparing compounds of formula (I).

A.a) The compounds of formula (I) can be prepared from carboxylic acids of structure 1 by reaction with an appropriate alcohol $R^2OH$ using standard coupling conditions such as EDC/HOBt, or DCC/HOAt, or PyBOP, or HATU in the presence of a base such as DIPEA or DMAP or a combination of both at a temperature ranging from rt to about 60° C. in a suitable solvent such as $CH_2Cl_2$ or THF/DMF. Alternatively, the compounds of formula (I) can be prepared by coupling carboxylic acids of structure 1 with an appropriate alcohol $R^2OH$ using $POCl_3$ in a suitable solvent such as DCE/pyridine (1:1). Alternatively, the compounds of formula (I) can be prepared by coupling carboxylic acids of structure 1 with an appropriate alcohol $R^2OH$ via formation of the acyl chloride (using standard conditions such as oxalyl chloride and a catalytic amount of DMF in a solvent such as toluene or $CH_2Cl_2$).

Structure 1

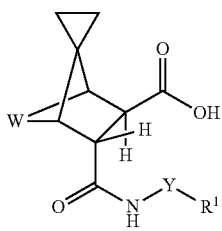

A.b) Alternatively, the compounds of formula (I) may be prepared from carboxylic acids of structure 3 with an appropriate amine $R^1$—Y—$NH_2$ using standard amide coupling conditions such as EDC/HOBt or DCC/HOAt in the presence of a base such as DIPEA or DMAP or a combination of both at a temperature about rt in a suitable solvent such as $CH_2Cl_2$. Alternatively, the compounds of formula (I) can be prepared by coupling carboxylic acids of structure 3 with an appropriate amine $R^1$—Y—$NH_2$ using $POCl_3$ in a suitable solvent such as DCE/pyridine (1:1). Alternatively, the compounds of formula (I) can be prepared by coupling carboxylic acids of structure 3 with an appropriate amine $R^1$—Y—$NH_2$ via formation of the acyl chloride (using standard conditions such as oxalyl chloride and a catalytic amount of DMF in a solvent such as toluene or $CH_2Cl_2$).

Structure 3

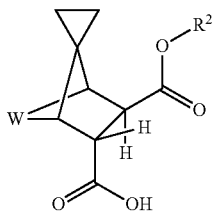

A.c) Alternatively, the compounds of formula (I) wherein $R^2$ contains a primary or secondary amino group may be prepared by deprotection of the corresponding protected amine such as N-tert-butoxycarbonyl protected amine, synthesized according to general methods A.a) or A.b), using an acid such as HCl in a solvent mixture such as dioxane and $CH_2Cl_2$ at a temperature about rt.

A.d) Alternatively, the compounds of formula (I) wherein $R^2$ contains an amide group (—C(O)$NR^5R^6$) may be prepared by saponification of the corresponding ester, synthesized according to general methods A.a) or A.b), followed by activation of the resulting carboxylic acid via a mixed anhydride for example using ethyl chloroformate and a base such as $Et_3N$ in a suitable solvent such as THF at a temperature ranging from about 0° C. to rt, and subsequent reaction with an appropriate amine $R^5R^6NH$.

A.e) Alternatively, the compounds of formula (I) wherein W represents —$CH_2CH_2$— can be prepared from compounds of formula (I) wherein W represents —CH=CH— by reduction of the double bond using $H_2$ and a catalyst such as $PtO_2$ in a suitable solvent such as ethyl acetate at a temperature about rt.

B. Synthesis of Intermediates

B1. Synthesis of Spiro Compounds

Scheme 1

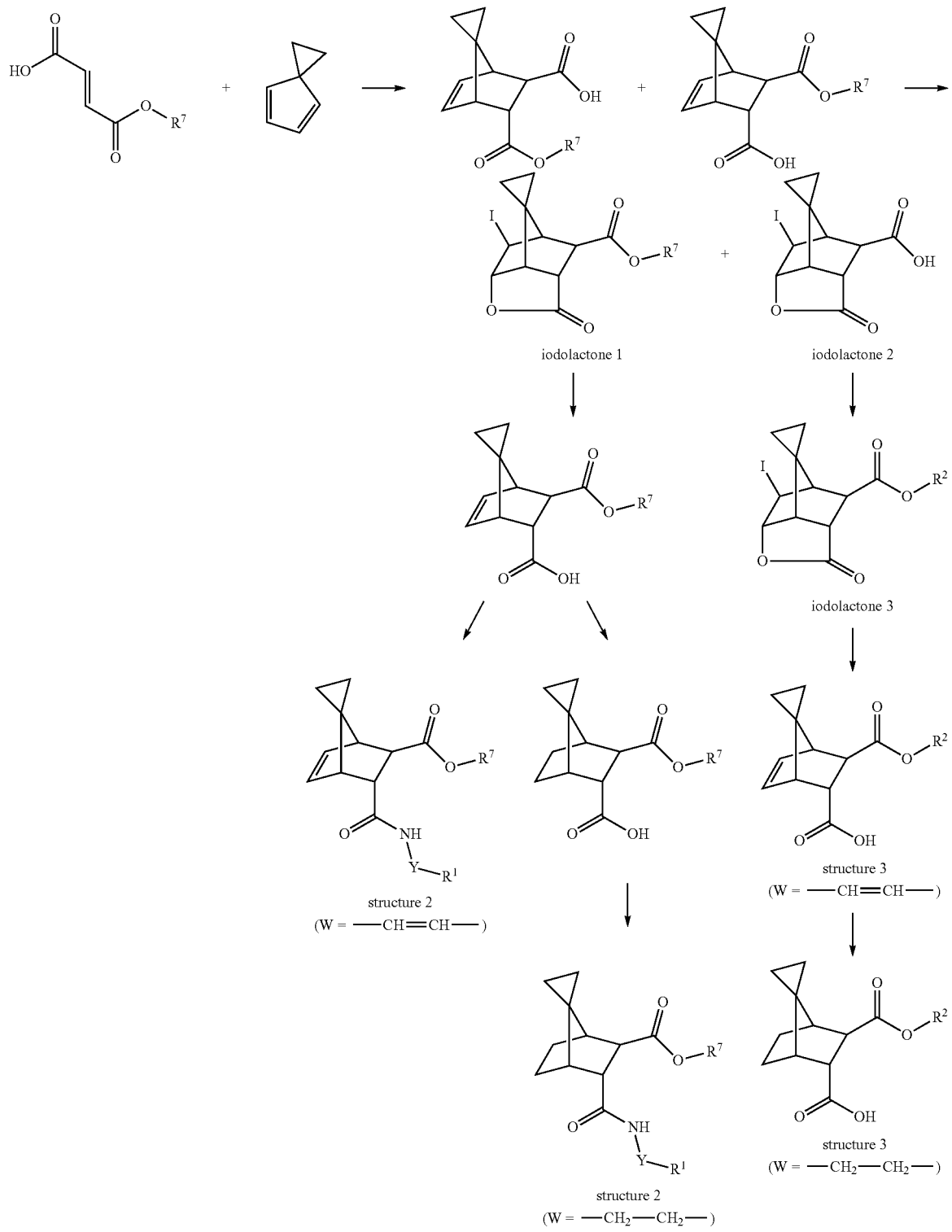

$R^7$ represents $(C_1-C_2)$alkyl

Compounds of structure 1 can be obtained by saponification of the ester moiety of compounds of structure 2 using a base such as LiOH or NaOH in a solvent such as a mixture of water and an organic solvent such as THF or EtOH.

Compounds of structure 2 wherein W represents —CH═CH— can be prepared by the following sequence (see scheme 1): a) Diels-Alder reaction between spiro[2.4] hepta-4,6-diene (prepared according to J. W. Coe et al. *Org.*

*Lett.* 2004, 6, 1589) and commercially available (E)-but-2-enedioic acid monoethyl ester in a suitable solvent such as MeOH to obtain a mixture of endo and exo products; b) iodolactonization using KI and I₂ in the presence of a base such as NaHCO₃ in a solvent such as CH₂Cl₂ at a temperature about rt to enable separation of the isomers (iodolactone 1 (ester) and iodolactone 2 (carboxylic acid)); c) retro-iodolactonization of the resulting iodolactone 1 using an excess of zinc in a solvent such as AcOH at a temperature about 65° C.; and d) amide coupling of the resulting carboxylic acid with an appropriate amine R¹—Y—NH₂ via formation of the acyl chloride (using standard conditions such as oxalyl chloride and a catalytic amount of DMF in a solvent such as toluene or CH₂Cl₂) in the presence of a base such as DIPEA, Et₃N or pyridine and in a suitable solvent such as CH₂Cl₂, THF or acetone or via activation of the carboxylic acid using standard amide coupling conditions such as EDC/HOBt in the presence of a base such as DIPEA or DMAP or a combination of both in a suitable solvent such as CH₂Cl₂.

Compounds of structure 2 wherein W represents —CH₂—CH₂— can be prepared by the following sequence (see scheme 1): a) Diels-Alder reaction between spiro[2.4]hepta-4,6-diene and commercially available (E)-but-2-enedioic acid monoethyl ester in a suitable solvent such as MeOH to obtain a mixture of endo and exo products; b) iodolactonization using KI and I₂ in the presence of a base such as NaHCO₃ in a solvent such as CH₂Cl₂ at a temperature about rt to enable separation of the isomers (iodolactone 1 (ester) and iodolactone 2 (carboxylic acid)); c) retro-iodolactonization of the resulting iodolactone 1 using an excess of zinc in a solvent such as AcOH at a temperature about 65° C.; d) reduction of the double bond using cyclohexene in the presence of Pd/C in a suitable solvent such as THF or using H₂ and a catalyst such as Pd/C in a suitable solvent such as THF; and e) amide coupling of the resulting carboxylic acid with an appropriate amine R¹—Y—NH₂ via formation of the acyl chloride (using standard conditions such as oxalyl chloride and a catalytic amount of DMF in a solvent such as toluene or CH₂Cl₂ in the presence of a base such as DIPEA, Et₃N or pyridine and in a suitable solvent such as CH₂Cl₂, THF or acetone or via activation of the carboxylic acid using standard amide coupling conditions such as EDC/HOBt in the presence of a base such as DIPEA or DMAP or a combination of both in a suitable solvent such as CH₂Cl₂.

Compounds of structure 3 wherein W represents —CH═CH— can be prepared by the following sequence (see scheme 1): a) coupling of iodolactone 2 with an appropriate alcohol R²OH, wherein R², if containing a primary or secondary amine function, might require protection for example as a N-tert-butoxycarbonyl protected amine, via formation of the acyl chloride (using standard conditions such as oxalyl chloride and a catalytic amount of DMF in a solvent such as toluene or CH₂Cl₂) in the presence of a base such as DIPEA and in a suitable solvent such as CH₂Cl₂ or via activation of the carboxylic acid using standard coupling conditions such as EDC/HOBt or HATU in the presence of a base such as DIPEA or DMAP or a combination of both in a suitable solvent such as CH₂Cl₂ or THF/DMF; and b) retro-iodolactonization of the resulting iodolactone 3 using an excess of zinc in a solvent such as AcOH at a temperature about 65° C.

Compounds of structure 3 wherein W represents —CH₂—CH₂— can be prepared by reduction of the double bond of compounds of structure 3 wherein W represents —CH═CH— using for example hydrogen in the presence of Pd/C in a suitable solvent such as EtOH or cyclohexene in the presence of Pd/C in a suitable solvent such as THF (see scheme 1).

Scheme 2

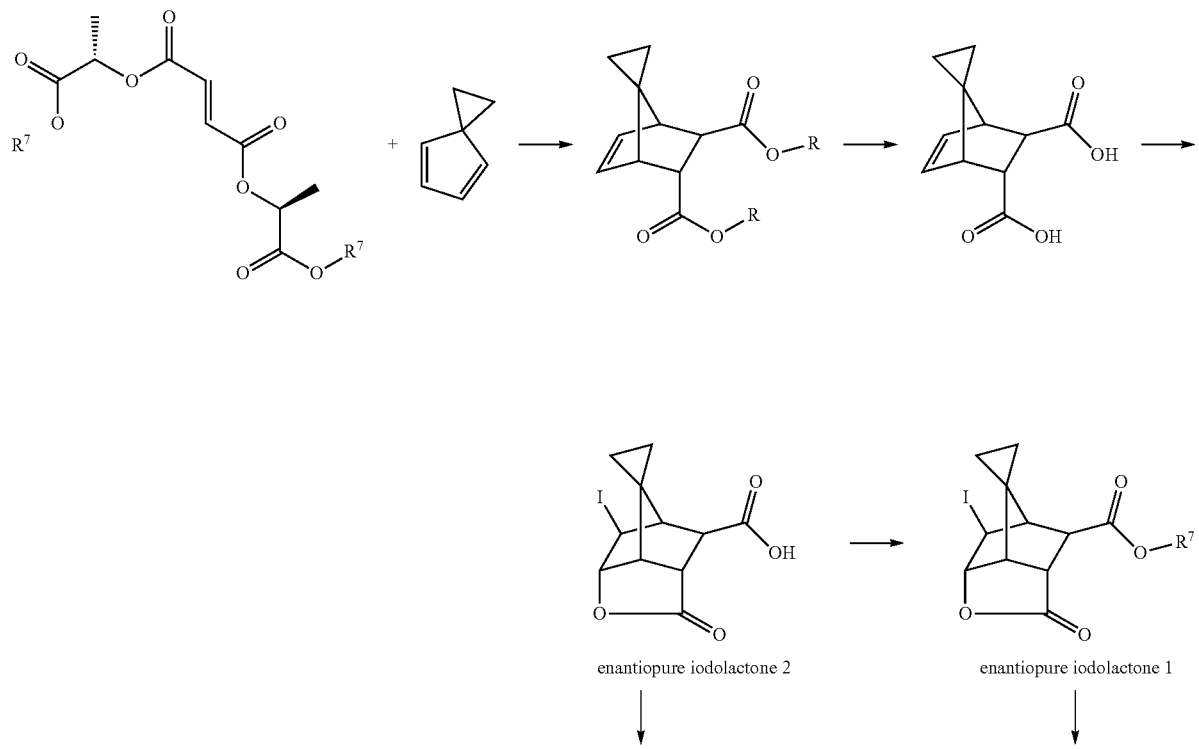

enantiopure iodolactone 2    enantiopure iodolactone 1

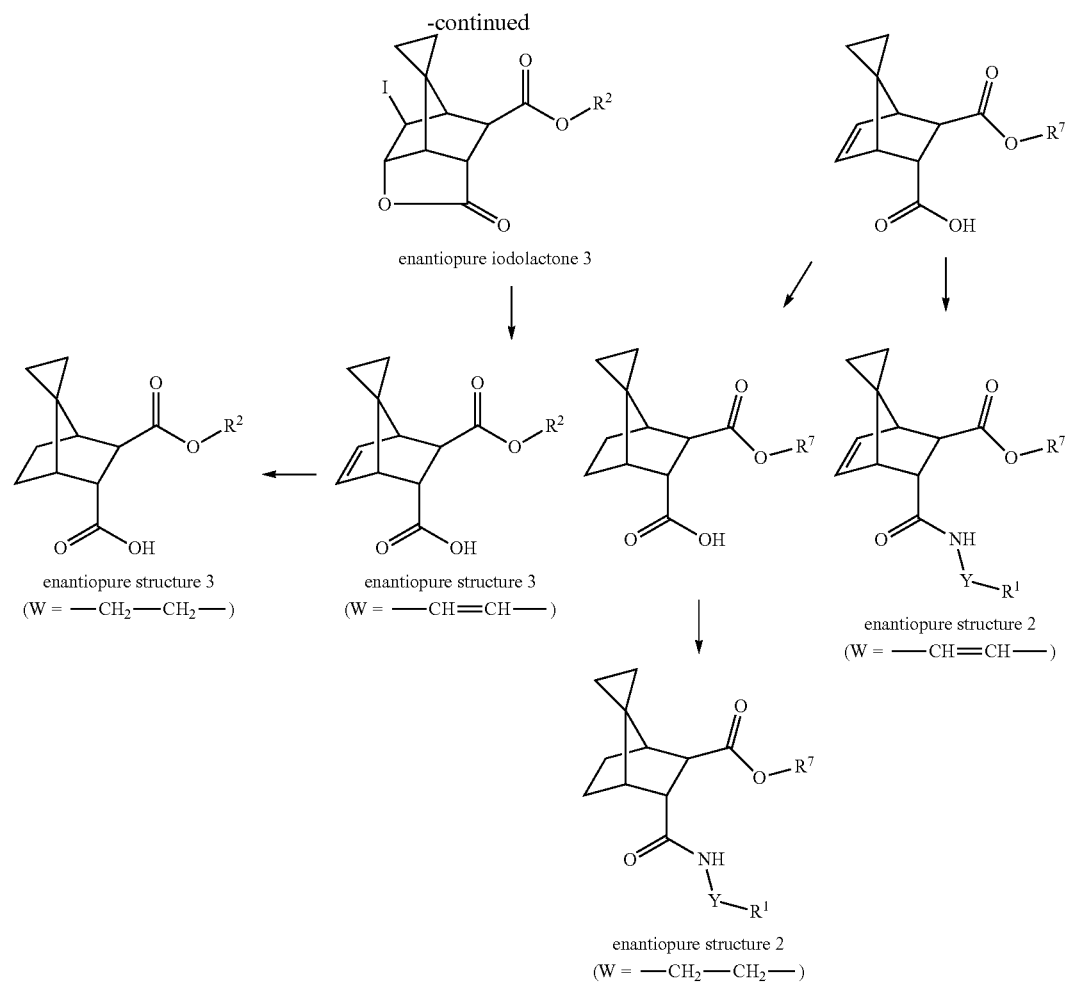

$R^7$ represents $(C_1-C_2)$alkyl and R represents $(S)$-CH(Me)COOR$^7$

Enantiopure compounds of structure 1 can be obtained by saponification of the ester moiety of enantiopure compounds of structure 2 using a base such as LiOH or NaOH in a solvent such as a mixture of water and an organic solvent such as THF or EtOH.

Enantiopure compounds of structure 2 wherein W represents —CH=CH— can be prepared by the following sequence (see scheme 2): a) Diels-Alder reaction between spiro[2.4]hepta-4,6-diene and commercially available (E)-1,2-bis-[((1S)-1-ethoxycarbonyl-ethoxy)-carbonyl]-ethene in a suitable solvent such as hexane; the assignment of the stereogenic centers of the obtained intermediates was made based on a literature reference (G. Helmchen et al., Angew. Chem. Int. Ed. 1987, 26, 1143), describing the Diels-Alder reaction between cyclopentadiene and (E)-1,2-bis-[((1S)-1-ethoxycarbonyl-ethoxy)-carbonyl]-ethene; b) saponification of the ester moieties using a base such as LiOH in a suitable solvent such as a mixture of THF and water; c) iodolactonization using KI and $I_2$ in the presence of a base such as NaHCO$_3$ in a solvent such as CH$_2$Cl$_2$ at a temperature about rt to give enantiopure iodolactone 2; d) esterification of the resulting carboxylic acid using standard conditions such as TMSCH$_2$N$_2$ in a suitable solvent such as MeOH or via formation of the acyl chloride (using standard conditions such as oxalyl chloride and a catalytic amount of DMF in a solvent such as toluene or CH$_2$Cl$_2$) and subsequent reaction with MeOH; e) retro-iodolactonization of the resulting iodolactone ester using an excess of zinc in a solvent such as AcOH at a temperature about 65° C.; and f) amide coupling of the resulting carboxylic acid with an appropriate amine R$^1$—Y—NH$_2$ via formation of the acyl chloride (using standard conditions such as oxalyl chloride and a catalytic amount of DMF in a solvent such as toluene or CH$_2$Cl$_2$) in the presence of a base such as DIPEA, Et$_3$N or pyridine and in a suitable solvent such as CH$_2$Cl$_2$, THF or acetone or via activation of the carboxylic acid using standard amide coupling conditions such as EDC/HOBt in the presence of a base such as DIPEA or DMAP or a combination of both in a suitable solvent such as CH$_2$Cl$_2$.

Enantiopure compounds of structure 2 wherein W represents —CH$_2$—CH$_2$— can be prepared by the following sequence (see scheme 2): a) esterification of enantiopure iodolactone 2 using standard conditions such as TMSCH$_2$N$_2$ in a suitable solvent such as MeOH or via formation of the acyl chloride (using standard conditions such as oxalyl chloride and a catalytic amount of DMF in a solvent such as toluene or CH$_2$Cl$_2$) and subsequent reaction with MeOH to give enantiopure iodolactone 1; b) retro-iodolactonization of the resulting iodolactone ester using an excess of zinc in a solvent such as AcOH at a temperature about 65° C.; c) reduction of the double bond using cyclohexene in the presence of Pd/C in a suitable solvent such as THF or using H$_2$ and a catalyst such as Pd/C in a suitable solvent such as THF; and d) amide coupling of the resulting carboxylic acid with an appropriate amine $R^1$—Y—$NH_2$ via formation of the acyl chloride (using standard conditions such as oxalyl chloride and a catalytic amount of DMF in a solvent such as toluene or $CH_2Cl_2$) in the presence of a base such as DIPEA, $Et_3N$ or pyridine and in a suitable solvent such as $CH_2Cl_2$, THF or acetone or via activation of the carboxylic acid using standard amide coupling conditions such as EDC/HOBt in the presence of a base such as DIPEA or DMAP or a combination of both in a suitable solvent such as $CH_2Cl_2$.

Enantiopure compounds of structure 3 wherein W represents —CH=CH— can be prepared by the following sequence (see scheme 2): a) coupling of enantiopure iodolactone 2 with an appropriate alcohol $R^2$OH, wherein $R^2$, if containing a primary or secondary amine function, might require protection for example as a N-tert-butoxycarbonyl protected amine, via formation of the acyl chloride (using standard conditions such as oxalyl chloride and a catalytic amount of DMF in a solvent such as toluene or $CH_2Cl_2$) in the presence of a base such as DIPEA and in a suitable solvent such as $CH_2Cl_2$ or via activation of the carboxylic acid using standard coupling conditions such as EDC/HOBt or HATU in the presence of a base such as DIPEA or DMAP or a combination of both in a suitable solvent such as $CH_2Cl_2$ or THF/DMF; and b) retro-iodolactonization of the resulting enantiopure iodolactone 3 using an excess of zinc in a solvent such as AcOH at a temperature about 65° C.

Enantiopure compounds of structure 3 wherein W represents —$CH_2$—$CH_2$— can be prepared by reduction of the double bond of enantiopure compounds of structure 3 wherein W represents —CH=CH— with, for instance, hydrogen in the presence of Pd/C in a suitable solvent such as EtOH or cyclohexene in the presence of Pd/C in a suitable solvent such as THF (see scheme 2).

In a general way, enantiopure compounds of structure 1 can be obtained either in analogy to the synthesis of racemic compounds of structure 1 starting from enantiopure iodolactone 1 or 2 or by chiral HPLC purification of a mixture of enantiomers.

B2. Synthesis of Amines $R^1$—Y—$NH_2$

Amines of formula $R^1$—Y—$NH_2$, if not commercially available, may be prepared for instance by the following sequence: a) conversion of alcohol $R^1$—Y—OH, wherein Y represents a ($C_1$-$C_2$)alkandiyl group, into the corresponding mesylate or chloride using for example MsCl in the presence of a base such as $Et_3N$ and DMAP in a suitable solvent such as $CH_2Cl_2$; b) conversion of the mesylate or chloride into the corresponding azide using for example $NaN_3$ in a solvent such as DMF at a temperature about 80° C.; c) reduction of the azide moiety either using $Ph_3P$ and water in a solvent such as THF at a temperature about 60° C., or by hydrogenation using a metal catalyst such as Pd/C in a suitable solvent such as MeOH.

Alternatively, amines of formula $R^1$—Y—$NH_2$, may be prepared by reduction of the corresponding nitrile using an appropriate reducing agent such as $BH_3$ in a suitable solvent such as THF.

Alternatively, amines of formula $R^1$—Y—$NH_2$, may be prepared by analogy to the methods described in the experimental part, or a combination of those and reported ones.

B3. Synthesis of Alcohols $R^2$—OH

Alcohols of formula $R^2$—OH, if not commercially available, may be prepared by reduction of the corresponding acids or esters using a suitable reducing agent.

Alcohols of formula $R^2$—OH, wherein $R^2$ represents ($C_3$-$C_6$)cycloalkyl, which is mono-substituted with $R^3R^4$N—$CH_2$— or heterocyclyl-methyl, if not commercially available, may be prepared for instance by alkylation of the appropriate halide with an appropriate amine $R^3R^4$NH or heterocycle or by selective protection/activation of the appropriate diol and subsequent alkylation with an appropriate amine $R^3R^4$NH or heterocycle.

Similarly, alcohols of formula $R^2$—OH, wherein $R^2$ represents ($C_2$-$C_6$)alkyl, which is mono-substituted with ($C_1$-$C_4$) alkoxy which is mono-substituted with heterocyclyl, if not commercially available, may be prepared for instance by alkylation of the appropriate halide with an appropriate heterocycle or by selective protection/activation of the appropriate diol and subsequent alkylation with an appropriate heterocycle.

Similarly, alcohols of formula $R^2$—OH, wherein $R^2$ represents ($C_1$-$C_6$)alkyl, which is mono-substituted either with ($C_3$-$C_6$)cycloalkyl, which cycloalkyl is mono-substituted with —$NR^3R^4$, or with heterocyclyl, if not commercially available, may be prepared for instance by alkylation of the appropriate halide with an appropriate amine $R^3R^4$NH or heterocycle or by selective protection/activation of the appropriate diol and subsequent alkylation with an appropriate amine $R^3R^4$NH or heterocycle.

Alcohols of formula $R^2$—OH, wherein $R^2$ represents ($C_3$-$C_5$)fluoroalkyl, which is mono-substituted with heterocyclyl, which heterocyclyl is unsubstituted or independently mono- or di-substituted at one or two of the carbon atoms with substituents independently selected from halogen and ($C_1$-$C_4$)alkyl, if not commercially available, may be prepared for instance by the following sequence: a) selective protection of the hydroxy group of an alkanol containing three to five carbon atoms, which is further substituted by, first, an halogen or —OH and, second, a further —OH group or an oxo group, by a suitable protecting group such as a benzyl group; b) alkylation of the appropriate halide with an appropriate heterocycle or selective activation of the appropriate alcohol and subsequent alkylation with an appropriate heterocycle; and c) introduction of the fluorine by displacement of an hydroxy group using a suitable reagent such as bis(2-methoxyethyl) aminosulfur trifluoride, or introduction of a di-fluorine moiety by reaction of an oxo group with a suitable reagent such as bis(2-methoxyethyl)aminosulfur trifluoride.

Alternatively, alcohols $R^2$—OH may be prepared by analogy to the methods described in the experimental part, or a combination of those and reported ones.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm) or AD-H (5-10 µm) column. Typical conditions of chiral HPLC are an isocratic mixture of eluent A (EtOH, in presence or absence of an amine such as $Et_3N$ or diethylamine) and eluent B (hexane), at a flow rate of 0.8 to 150 mL/min.

For instance, enantiopure compounds of structure 2 may be obtained by chiral HPLC separation of a mixture of enantiomers; for example, (5R)—$N^5$-(4-bromo-phenyl)-(6R)-6-ethoxycarbonyl-(4S,7R)-[4,7-ethenylene-spiro[2.4]heptane]-5-carboxamide may be obtained by chiral HPLC separation of (5R*)—$N^5$-(4-bromo-phenyl)-(6R*)-6-ethoxycarbonyl-(4S*,7R*)-[4,7-ethenylene-spiro[2.4]heptane]-5-carboxamide. Preferably such separations are performed using a Daicel ChiralPak AD-H column with a mixture of EtOH and hexane (15/85) as eluent.

EXPERIMENTAL PART

Abbreviations

As Used Herein and in the Description Above

Ac acetyl
AcCN acetonitrile
AcOH acetic acid
AIBN azo-bis-(isobutyronitrile)
aq. aqueous
atm atmosphere
9-BBN 9-borabicyclo[3.3.1]nonane
Boc tert-butoxycarbonyl
bp boiling point
ca. about
COAD chronic obstructive airway disease
COLD chronic obstructive lung disease
COPD chronic obstructive pulmonary disease
DAD diode array detector
DC dendritic cells
DCC N,N'-dicyclohexylcarbodiimide
DCE 1,2-dichloroethane
DIBAL-H diisobutylaluminiun hydride
DIPEA diisopropylethylamine
DMAP 4-N,N-dimethylaminopyridine
DMEM dulbecco's modified eagle's medium
DMF dimethylformamide
DMSO dimethylsulfoxide
EA ethyl acetate
$EC_{50}$ half maximal effective concentration
EDC N-(3-dimethylaminopropyl)-N-ethyl-carbodiimide
ELSD evaporative light-scattering detection
eq. equivalent(s)
ES+ electro-spray, positive ionization
Et ethyl
Ether or $Et_2O$ diethylether
$Et_3N$ triethylamine
EtOH ethanol
FA formic acid
FAD familial autosomic dominant
FC flash column chromatography on silica gel
FLIPR fluorescence imaging plate reader
FPRL1 formyl-peptide receptor like-1
FPRL2 formyl-peptide receptor like-2
h hour(s)
HATU 2-(7-aza-1H-benzotriazol-1-yl)-1,1,3,3-tetramethyluronium hexafluorophosphate
HEPES 4-(2-hydroxyethyl)-1-piperazineethanesulfonic acid
hept heptane
HIV human immunodeficiency virus
HOBt hydroxybenzotriazole
HOAt 7-aza-1-hydroxybenzotriazole
HPLC high performance liquid chromatography
LC-MS liquid chromatography-mass spectrometry
lem emission wavelength
lex excitation wavelength
LPS lipopolysaccharide
Me methyl
MeOH methanol
min minute(s)
mM millimolar
μM micromolar
mRNA messenger ribonucleic acid
MPLC medium pressure liquid chromatography
MS mass spectrometry
Ms methanesulfonyl
nm nanometer
nM nanomolar
NMR nuclear magnetic resonance
org. organic
PG protecting group
PyBOP benzotriazol-1-yl-oxy-tris-pyrrolidino-phosphonium-hexafluoro-phosphate
rf retention factor
rpm rotation per minute
rt room temperature
sat. saturated
t-Bu tert-butyl
TFA trifluoroacetic acid
THF tetrahydrofuran
TLC thin layer chromatography
$t_R$ retention time
UV ultra violet
V is visible I Chemistry General.

All temperatures are stated in degrees Celsius (° C.). Unless otherwise indicated, the reactions take place at rt.

As polymer supported hydrogen carbonate, $PL-HCO_3$ from Polymer Laboratories was used.

Analytical thin layer chromatography (TLC) was performed with 0.2 mm plates: Merck, Silica gel 60 $F_{254}$. Preparative thin layer chromatography (TLC) was performed with 0.2 or 0.5 mm plates: Merck, Silica gel 60 $F_{254}$. Detection was done with UV or with a solution of $KMnO_4$ (3 g), $K_2CO_3$ (20 g), NaOH 5% (3 mL) and $H_2O$ (300 mL) with subsequent heating.

Flash column chromatography (FC) and filtration were performed using silica gel 60 Merck (0.063-0.200 mm) or Macherey-Nagel silica gel (0.063-0.200 mm): elution with EA, $Et_2O$, hept, hexane, $CH_2Cl_2$, $CHCl_3$, MeOH, $NH_4OH$ or mixtures thereof.

MPLC were performed using Isolute® SPE Flash SI II columns from international sorbent technology, elution with EA, $Et_2O$, hept, hexane, $CH_2Cl_2$, $CHCl_3$, MeOH, $NH_4OH$ or mixtures thereof.

LC-MS-conditions 01 (if not indicated otherwise): Analytical: Thermo Finnigan MSQ Surveyor MS with Agilent 1100 Binary Pump and DAD. Column: Zorbax SB-AQ 5 μm, 4.6×50 mm ID from Agilent Technologies. Eluents: A: $H_2O$+ 0.04% TFA; B: AcCN; Gradient: 5% B→95% B over 1 min. Flow: 4.50 mL/min. Detection: UV/Vis and/or ELSD, and MS, $t_R$ is given in min.

LC-MS-conditions 02 (if not indicated otherwise): Analytical: Thermo Finnigan MSQ Plus MS with Agilent 1100 Binary Pump and DAD. Column: Zorbax SB-AQ 5 μm, 4.6× 50 mm ID from Agilent Technologies. Eluents: A: $H_2O$+ 0.04% TFA; B: AcCN; Gradient: 5% B→95% B over 1 min. Flow: 4.50 mL/min. Detection: UV/Vis and/or ELSD, and MS, $t_R$ is given in min.

LC-MS-conditions 07 (if not indicated otherwise): Analytical. Pump: Dionex HPG-3200RS, MS: Thermo MSQ Plus, DAD: Dionex DAD-3000RS, ELSD: Sedere Sedex 85. Column: Xbridge C18 2.5 μM, 4.6×30 mm ID from Waters, thermostated in the Dionex TCC-3200 compartment. Eluents: A: $H_2O$+0.04% TFA; B: AcCN. Method: Gradient: 5% B→95% B over 1.00 min. Flow: 4.5 mL/min. Detection: UV/Vis and/or ELSD, and MS, $t_R$ is given in min.

LC-MS-conditions 08 (if not indicated otherwise): Analytical. Pump: Dionex HPG-3200RS, MS: Thermo MSQ Plus, DAD: Dionex DAD-3000RS, ELSD: Sedere Sedex 85. Column: Zorbax SB-AQ 3.5 μm, 4.6×50 mm ID from Agilent Technologies, thermostated in the Dionex TCC-3200 compartment. Eluents: A: $H_2O+0.04\%$ TFA; B: AcCN. Method: Gradient: 5% B→95% B over 1.00 min. Flow: 4.5 mL/min. Detection: UV/Vis and/or ELSD, and MS, $t_R$ is given in min.

LC-MS-conditions FA (if not indicated otherwise): Analytical. Pump: Waters Acquity Binary Solvent Manager, MS: Waters SQ Detector, DAD: Acquity UPLC PDA Detector, ELSD: Acquity UPLC ELSD. Column: Acquity UPLC CSH C18 1.7 μm 2.1×50 mm ID from Waters, thermostated in the Acquity UPLC Column Manager at 60° C. Eluents: A: $H_2O+$ 0.05% FA; B: AcCN+0.04% FA. Method: Gradient: 2% B→98% B over 2.00 min. Flow: 1.2 mL/min. Detection: UV/Vis and/or ELSD, and MS, $t_R$ is given in min.

LC-MS-conditions TFA (if not indicated otherwise): Analytical. Pump: Waters Acquity Binary Solvent Manager, MS: Waters SQ Detector, DAD: Acquity UPLC PDA Detector, ELSD: Acquity UPLC ELSD. Column: Acquity UPLC BEH C18 1.7 μm 2.1×50 mm ID from Waters, thermostated in the Acquity UPLC Column Manager at 60° C. Eluents: A: $H_2O+$ 0.05% TFA; B: AcCN+0.045% FA. Method: Gradient: 2% B→98% B over 2.00 min. Flow: 1.2 mL/min. Detection: UV/Vis and/or ELSD, and MS, $t_R$ is given in min.

HPLC preparative: X-Bridge C18 5 μm, 50×19 mm ID from Waters. Eluents: A: $H_2O+0.5\%$ $NH_4OH$; B: AcCN; Gradient: 10% B→90% B over 5 min. Flow: 40.0 mL/min. Detection: UV/Vis and/or ELSD, and MS, $t_R$ is given in min.

HPLC chiral, analytical: a) Regis Whelk column, 4.6×250 mm, 10 μm. Eluent A: EtOH+0.05% $Et_3N$. Eluent B: hexane. Flow: 1 mL/min. b) ChiralPak AD, 4.6×250 mm, 5 μm. Eluent A: EtOH+0.05% $Et_3N$. Eluent B: hexane. Flow: 1 mL/min. c) ChiralCel OD, 4.6×250 mm, 10 μm. Eluent A: EtOH+0.1% $Et_3N$. Eluent B: hexane. Flow: 0.8 mL/min. Detection: UV/Vis, $t_R$ is given in min.

HPLC chiral, preparative: a) Regis Whelk 01 column, 50×250 mm. Flow: 100 mL/min. b) ChiralPak AD, 20×250 mm. Flow: 10 mL/min. c) ChiralCel OD, 20 μm, 50 mm×250 mm. Flow: 100 mL/min. Detection: UV/Vis, $t_R$ is given in min.

NMR: Bruker Avance 400 (400 MHz); Varian Mercury 300 (300 MHz); chemical shifts are given in ppm relative to the solvent used; multiplicities: s=singlet, d=doublet, t=triplet, q=quadruplet, p=pentuplet, hex=hextet, hept=heptet, m=multiplet, br=broad, coupling constants are given in Hz.

The following examples illustrate the invention but do not at all limit the scope thereof.

General Procedures

General Procedure A: Ester Formation (1)

In a flame dried round-bottomed flask equipped with a magnetic stir bar and under inert atmosphere ($N_2$), to a solution of the carboxylic acid (1.0 eq.) in $CH_2Cl_2$ (0.2 M) were added an alcohol (1.0-2.0 eq.), EDC HCl (2.0-4.0 eq.), HOBt (1.2-2.4 eq.) and DIPEA (3.0-6.0 eq.). The reaction mixture was stirred at rt until completion of the reaction. Water was then added, the layers separated and the org. layer dried over $MgSO_4$, filtered, and concentrated under reduced pressure. Purification of the residue, when necessary, by FC or HPLC gave the desired compound.

General Procedure B: Ester Formation (2)

In a glass vial, under inert atmosphere ($N_2$), to an alcohol (1.2 eq.) was added a solution of the carboxylic acid (1.0 eq.) in $CH_2Cl_2$ (0.1 M), EDC.HCl (1.1-1.3 eq.) and DMAP (1.0-1.2 eq.). The reaction mixture was stirred at rt or 40° C. until completion of the reaction. PL-HCO_3 was added and the mixture stirred at rt for 2 h, filtered and the filtrate concentrated under reduced pressure. Purification of the residue, when necessary, by HPLC gave the desired compound.

General Procedure C: Ester Formation (3)

In a flame dried round-bottomed flask equipped with a magnetic stir bar and under inert atmosphere ($N_2$), to a mixture of the carboxylic acid (1.0 eq.), an alcohol (2.0 eq.) and HATU (2.0 eq.) in THF/DMF 4:1 (1 mL per 0.2 mmol of HATU) was added DIPEA (3.0-6.0 eq.). The reaction mixture was stirred at rt or 60° C. until completion of the reaction. Water was then added and the mixture extracted with EA (3×). The combined org. extracts were washed with brine, dried over $MgSO_4$, filtered and concentrated under reduced pressure. Purification of the residue, when necessary, by FC or HPLC gave the desired compound.

General Procedure D: Boc Deprotection

In a glass vial, under inert atmosphere ($N_2$), a solution of the Boc-protected amine (1.0 eq.) in $CH_2Cl_2$ was treated with 4N HCl in dioxane (10.0 eq.) and the reaction mixture was stirred at 0° C. or rt until completion of the reaction. The reaction mixture was then concentrated under reduced pressure and the residue purified, when necessary, by FC or HPLC to give the desired compound.

General Procedure E: Dioxolane Deprotection

In a flame dried round-bottomed flask equipped with a magnetic stir bar and under inert atmosphere ($N_2$), a solution of the dioxolane-protected diol (1.0 eq.) in $THF/H_2O$ (1:1, 0.06 M) was treated with AcOH (28.0 eq.) and the reaction mixture was stirred at 60° C. until completion of the reaction. The reaction mixture was cooled down to rt, partitioned between sat. aq. $NaHCO_3$ and EA. The layers were separated and the aq. layer extracted with EA (2×). The combined org. extracts were then dried over $MgSO_4$, filtered and concentrated under reduced pressure and the residue purified, when necessary, by FC or HPLC to give the desired compound.

General Procedure F: Double Bond Reduction

In a flame dried round-bottomed flask equipped with a magnetic stir bar, a suspension of alkene (1.0 eq.) and $PtO_2$ (0.1-0.2 eq.) in dry EA was stirred at rt under a $H_2$ atmospheric pressure until completion of the reaction. The mixture was then filtered, washed with EA, and the filtrate concentrated under reduced pressure. The crude residue was purified, when necessary, by FC or HPLC to give the desired compound.

Synthesis of Intermediates

Spiro[2.4]hepta-4,6-diene

In a flame dried round-bottomed flask equipped with a magnetic stir bar and under inert atmosphere ($N_2$), a mixture of benzyltriethylammonium chloride (18.0 g, 78 mmol) in 50% aqueous NaOH solution (1.2 L) was heated to 45° C. A chilled solution of cyclopentadiene (formed by cracking of cyclopentadiene dimer at 180° C., 140 mL, 1.70 mol) in 1,2-dichloroethane (122 mL, 1.55 mol) was added to the stirred NaOH solution while keeping the internal temperature below 55° C. After completion of the addition (ca. 1.75 h), the reaction mixture was stirred at 50° C. for 2 h and allowed to cool down to rt. The layers were separated, the organic layer washed with 1M NaOH, dried ($Na_2SO_4$) and filtered. The crude brown liquid was distilled under reduced pressure (85-95 mbar) and the title compound was obtained as a colorless liquid (bp=45-50° C. at 80 mbar). $^1H$ NMR (400 MHz, $CDCl_3$) δ 6.58 (m, 2H), 6.19 (m, 2H), 1.71 (s, 4H).

2-(2-(Pyrrolidin-1-yl)ethoxy)ethanol

In a flame dried round-bottomed flask equipped with a magnetic stir bar and under inert atmosphere ($N_2$), to a solution of pyrrolidine (0.35 mL, 4.22 mmol) and 2-(2-chloroethoxy)ethanol (0.45 mL, 4.22 mmol) in dry toluene (7 mL) was added $K_2CO_3$ (3.21 g, 23.20 mmol) at rt followed by KI (70 mg, 0.42 mmol). The reaction mixture was stirred at reflux for 15 h. The mixture was filtered and the filtrate concentrated under reduced pressure to give crude 2-(2-(pyrrolidin-1-yl)ethoxy)ethanol as a yellow oil. TLC:rf (90:10: 0.5 $CH_2Cl_2$-MeOH—$NH_4OH$)=0.17.

(S)-2-(2-(3-Fluoropyrrolidin-1-yl)ethoxy)ethanol

In a flame dried round-bottomed flask equipped with a magnetic stir bar and under inert atmosphere ($N_2$), to a solution of (5)-3-fluoropyrrolidine hydrochloride (250 mg, 1.99 mmol) and 2-(2-chloroethoxy)ethanol (0.21 mL, 1.99 mmol) in dry toluene (7 mL) was added $K_2CO_3$ (1.51 g, 10.95 mmol) at rt followed by KI (33 mg, 0.20 mmol). The reaction mixture was stirred at reflux for 15 h. The mixture was filtered and the filtrate concentrated under reduced pressure to give crude (S)-2-(2-(3-fluoropyrrolidin-1-yl)ethoxy)ethanol as a yellow oil. TLC:rf (90:10:0.5 $CH_2Cl_2$-MeOH—$NH_4OH$)=0.23.

Diels Alder reaction—formation of (5R,6R)-5,6-bis-[(1-(1S)-ethoxycarbonyl)-ethoxy-carbonyl]-(4S,7R)-[4,7-ethenylene-spiro[2.4]heptane]

In a flame dried round-bottomed flask equipped with a magnetic stir bar and under inert atmosphere ($N_2$), to a solution of (E)-1,2-bis-[((1S)-1-ethoxycarbonyl)-ethoxy-carbonyl]-ethene (7.40 g, 22.7 mmol) in n-hexane (76 mL) was added spiro[2.4]hepta-4,6-diene (3.14 g, 34.0 mmol) at rt. The reaction mixture was stirred at this temperature overnight. The mixture was concentrated under reduced pressure and the crude residue purified by FC (hept/EA, 9:1). The title compound was obtained as a pale yellow oil. TLC:rf (9:1 hept-EA)=0.25. LC-MS-conditions 02: $t_R$=1.12 min; $[M+H]^+$=409.00. $^1$H NMR (400 MHz, $CDCl_3$) δ 6.44 (dd, J=5.5, 3.0 Hz, 1H), 6.32 (dd, J=5.5, 2.8 Hz, 1H), 5.12 (q, J=7.1 Hz, 1H), 5.06 (q, J=7.1 Hz, 1H), 4.28-4.14 (m, 4H), 3.76 (app. t, J=4.0 Hz, 1H), 2.92 (d, J=4.8 Hz, 1H), 2.86 (m, 1H), 2.80 (m, 1H), 1.55-1.47 (m, 6H), 1.29 (t, J=7.3 Hz, 3H), 1.29 (t, J=7.3 Hz, 3H), 0.70 (m, 1H), 0.56-0.44 (m, 3H).

Saponification—formation of (4S,7R)-[4,7-ethenylene-spiro[2.4]heptane]-(5R,6R)-5,6-bis-carboxylic acid To a solution of (5R,6R)-5,6-bis-[(1-(1S)-ethoxycarbonyl)-ethoxy-carbonyl]-(4S,7R)-[4,7-ethenylene-spiro[2.4] heptane] (9.51 g, 23.28 mmol) in $THF/H_2O$ (1:1, 232 mL) was added LiOH (3.91 g, 93.13 mmol). The reaction mixture was stirred at rt overnight. 1N HCl was added in order to adjust the pH of the reaction mixture to pH=3, the layers separated and the aq. layer extracted with EA (3×). The combined org. extracts were dried over $MgSO_4$, filtered, and concentrated under reduced pressure. The crude residue was purified by FC ($CH_2Cl_2$/MeOH, 9:1) to give the title compound as a colorless oil. TLC:rf (9:1 $CH_2Cl_2$/MeOH)=0.31. LC-MS-conditions 02: $t_R$=0.72 min; $[M+AcCN+H]^+$= 250.18.

Iodolactonization—Formation of Enantiopure Iodolactone 2

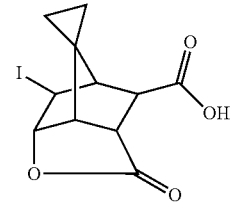 [SMILES: O=C(O)C1C2C(=O)OC3C(I)C1C1(CC1)C32]

To a solution of (4S,7R)-[4,7-ethenylene-spiro[2.4]heptane]-(5R,6R)-5,6-bis-carboxylic acid (5.60 g, 22.32 mmol) in $CH_2Cl_2$ (33 mL) were added $NaHCO_3$ (2.06 g, 24.56 mmol), water (100 mL), KI (1.37 g, 82.60 mmol) and $I_2$ (6.80 g, 26.79 mmol). The reaction mixture was stirred at rt for 3 h. The reaction was quenched by the addition of sat. aq. $Na_2S_2O_3$. The layers were separated and the aq. layer extracted with $CH_2Cl_2$ (3×). The combined org. extracts were dried over $MgSO_4$, filtered, and concentrated under reduced pressure. The crude foam was purified by FC (EA) to give enantiopure iodolactone 2 as a white solid. TLC: rf (EA)= 0.33.

Esterification—Formation of Enantiopure Iodolactone 1 ($R^7$=Me)

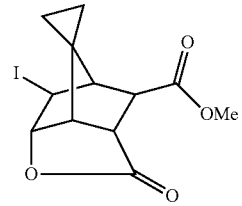 [SMILES: COC(=O)C1C2C(=O)OC3C(I)C1C1(CC1)C32]

In a name cried round-bottomed flask equipped with a magnetic stir bar and under inert atmosphere ($N_2$), to a solution of enantiopure iodolactone 2 (5.00 g, 14.96 mmol) in dry MeOH (75 mL) was added $TMSCH_2N_2$ (2.0 M in hexanes, 37.0 mL, 74.83 mmol). The reaction mixture was stirred at rt overnight, concentrated under reduced pressure and purified by FC (hept-EA, 4:1) to give enantiopure iodolactone 1 ($R^7$=Me) as a white solid. TLC:rf (4:1 hept-EA)=0.18.

Retro-iodolactonization—formation of (6R)-6-methoxycarbonyl-(4S,7R)-[4,7-ethenylene-spiro[2.4]heptane]-(5R)-5-carboxylic acid In a flame dried round-bottomed flask equipped with a magnetic stir bar and under inert atmosphere ($N_2$), to a solution of enantiopure iodolactone 1 ($R^7$=Me) (2.86 g, 8.21 mmol) in acetic acid (29 mL) was added zinc powder (8.06 g, 123.23 mmol). The reaction mixture was stirred at 65° C. for 4 h, cooled down to rt, filtered and partitioned between water and EA. The layers were separated and the aq. layer extracted with EA (3×). The combined org. extracts were washed with brine, dried over $MgSO_4$, filtered, and concentrated under reduced pressure. The crude residue was purified by FC (hept-EA, 1:1) and the title compound was obtained as a colorless oil. TLC:rf (1:1 hept-EA)=0.41.

Amide coupling (with 4-bromo-aniline)—formation of (5R)—N$^5$-(4-bromo-phenyl)-(6R)-6-methoxycarbonyl-(4S,7R)-[4,7-ethenylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethenylene-spiro[2.4]heptane]-(5R)-5-carboxylic acid (2.00 g, 9.00 mmol) in dry CH$_2$Cl$_2$ (25 mL) were added a few drops of DMF and oxalyl chloride (0.84 mL, 10.00 mmol). The reaction mixture was stirred at rt for 30 minutes. A solution of 4-bromo-aniline (2.32 g, 13.50 mmol) in dry CH$_2$Cl$_2$ (12.5 mL) was then added at rt followed by DIPEA (6.2 mL, 36.00 mmol). The reaction mixture was stirred at rt for 30 min, diluted with EA and successively washed with aq. 1N HCl, sat. aq. NaHCO$_3$ and brine. The org. layer was dried over MgSO$_4$, filtered, and concentrated under reduced pressure. The crude residue was purified by FC (hept-EA, 3:2) and the title compound obtained as a white solid. TLC:rf (3:2 hept-EA)=0.57. LC-MS-conditions 02: $t_R$=1.05 min; [M+H]$^+$=376.30.

(5R)—N$^5$-(4-Bromo-phenyl)-(6R)-6-hydroxycarbonyl-(4S,7R)-[4,7-ethenylene-spiro[2.4]heptane]-5-carboxamide To a solution of (5R)—N$^5$-(4-bromo-phenyl)-(6R)-6-methoxycarbonyl-(4S,7R)-[4,7-ethenylene-spiro[2.4]heptane]-5-carboxamide (3.30 g, 8.77 mmol) in THF (35 mL) was added aq. 1N NaOH (17 mL, 17.00 mmol). The reaction mixture was stirred at rt until completion of the reaction. The mixture was then poured into aq. 1N HCl and extracted with EA (3×). The combined org. extracts were washed with brine, dried over MgSO$_4$, filtered, and concentrated under reduced pressure to give the title compound as a yellow solid. LC-MS-conditions 01: $t_R$=0.92 min; [M+H]$^+$=361.90.

Double bond reduction—formation of (6R)-6-methoxycarbonyl-(4S,7R)-[4,7-ethylene-spiro[2.4]heptane]-(5R)-5-carboxylic acid In a flame dried round-bottomed flask equipped with a magnetic stir bar and under inert atmosphere (N$_2$), a deoxygenated suspension of (6R)-6-methoxycarbonyl-(4S,7R)-[4,7-ethenylene-spiro[2.4]heptane]-(5R)-5-carboxylic acid (220 mg, 0.99 mmol), Pd/C 10% (44 mg) and cyclohexene (0.20 mL, 1.98 mmol) in dry THF (2.5 mL) was stirred at reflux for 2 h. The reaction mixture was filtered through celite and the filter cake washed with THF. The filtrate was concentrated under reduced pressure and the title compound obtained as a white solid. TLC:rf (2:3 hept-EA)=0.48.

Amide coupling (with 4-bromo-2-fluorobenzylamine)—formation of (5R)—N$^5$-(4-bromo-2-fluorophenyl-methyl)-(6R)-6-methoxycarbonyl-(4S,7R)-[4,7-ethylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethylene-spiro[2.4]heptane]-(5R)-5-carboxylic acid (160 mg, 0.71 mmol) in dry CH$_2$Cl$_2$ (4 mL) were added 3 drops of DMF and oxalyl chloride (0.07 mL, 0.81 mmol). The reaction mixture was stirred at rt for 60 minutes and concentrated under reduced pressure.

To a suspension of 4-bromo-2-fluorobenzylamine hydrochloride (171 mg, 0.71 mmol) in pyridine (0.84 mL) was added a solution of the acyl chloride in acetone (4 mL). The reaction mixture was stirred at rt for 1 h, diluted with EA and successively washed with aq. 1N HCl, sat. aq. NaHCO$_3$ and brine. The org. layer was dried over MgSO$_4$, filtered, and concentrated under reduced pressure to give the title compound obtained as a yellow oil. LC-MS-conditions 02: $t_R$=1.06 min; [M+H]$^+$=410.67.

(5R)—N$^5$-(4-Bromo-2-fluorophenyl-methyl)-(6R)-6-hydroxycarbonyl-(4S,7R)-[4,7-ethylene-spiro[2.4]heptane]-5-carboxamide To a solution of (5R)—N$^5$-(4-bromo-2-fluorophenyl-methyl)-(6R)-6-methoxycarbonyl-(4S,7R)-[4,7-ethylene-spiro[2.4]heptane]-5-carboxamide (290 mg, 0.71 mmol) in THF (5 mL) was added aq. 1N NaOH (2.8 mL, 2.80 mmol). The reaction mixture was stirred at rt until completion of the reaction. The mixture was then poured into aq. 1N HCl and extracted with EA (3×). The combined org. extracts were washed with brine, dried over MgSO$_4$, filtered, and concentrated under reduced pressure to give the title compound as a white foam. LC-MS-conditions 01: $t_R$=0.93 min; [M+H]$^+$=395.95.

Amide coupling (with 5-amino-2-bromo-pyridine)—formation of (5R)—N$^5$-(2-bromo-pyrid-5-yl)-(6R)-6-methoxycarbonyl-(4S,7R)-[4,7-ethylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethylene-spiro[2.4]heptane]-(5R)-5-carboxylic acid (2.55 g, 11.37 mmol) in dry CH$_2$Cl$_2$ (60 mL) were added 10 drops of DMF and oxalyl chloride (1.20 mL, 13.65 mmol). The reaction mixture was stirred at rt for 60 minutes and concentrated under reduced pressure.

To a suspension of 5-amino-2-bromo-pyridine (1.97 g, 11.37 mmol) in pyridine (2.75 mL) was added a solution of the acyl chloride in acetone (60 mL). The reaction mixture was stirred at rt for 30 minutes, diluted with EA and successively washed with aq. 1N HCl, sat. aq. NaHCO$_3$ and brine. The org. layer was dried over MgSO$_4$, filtered, and concentrated under reduced pressure. The crude residue was purified by FC (hept-EA, 1:0→1:1) and the title compound obtained as a white solid. TLC:rf (2:1 hept-EA)=0.44. LC-MS-conditions 07: $t_R$=0.84 min; [M+H]$^+$=379.04.

(5R)-N$^5$-(2-Bromo-pyrid-5-yl)-(6R)-6-hydroxycarbonyl-(4S,7R)-[4,7-ethylene-spiro[2.4]heptane]-5-carboxamide To a solution of (5R)—N$^5$-(2-bromo-pyrid-5-yl)-(6R)-6-methoxycarbonyl-(4S,7R)-[4,7-ethylene-spiro[2.4]heptane]-5-carboxamide (3.81 g, 10.05 mmol) in THF (100 mL) was added aq. 2N NaOH (20 mL, 40.00 mmol). The reaction mixture was stirred at rt until completion of the reaction. The mixture was then poured into aq. 1N HCl and extracted with EA (3×). The combined org. extracts were washed with brine, dried over MgSO$_4$, filtered, and concentrated under reduced pressure to give the title compound as a white solid. LC-MS-conditions 07: $t_R$=0.72 min; [M+H]$^+$=365.22.

Amide coupling (with (5-methylisoxazol-3-yl) methanamine)—formation of (5R)—N$^5$-((5-methyl isoxazol-3-yl)methyl)-(6R)-6-methoxycarbonyl-(4S, 7R)-[4,7-ethylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethylene-spiro[2.4]heptane]-(5R)-5-carboxylic acid (1.75 g, 7.79 mmol) in dry CH$_2$Cl$_2$ (30 mL) were added 5 drops of DMF and oxalyl chloride (0.82 mL, 9.34 mmol). The reaction mixture was stirred at rt for 60 minutes and concentrated under reduced pressure.

To a suspension of (5-methylisoxazol-3-yl)methanamine (0.90 g, 7.79 mmol) in pyridine (1.9 mL) was added a solution of the acyl chloride in acetone (30 mL). The reaction mixture was stirred at rt for 30 minutes, diluted with EA and successively washed with aq. 1N HCl, sat. aq. NaHCO$_3$ and brine. The org. layer was dried over MgSO$_4$, filtered, and concentrated under reduced pressure. The crude residue was purified by FC (hept-EA, 5:1) and the title compound obtained as an off-white solid. TLC:rf (1:1 hept-EA)=0.38. LC-MS-conditions 07 $t_R$=0.70 min; [M+H]$^+$=319.12.

(5R)—N$^5$-((5-Methyl isoxazol-3-yl)methyl)-(6R)-6-hydroxycarbonyl-(4S,7R)-[4,7-ethylene-spiro[2.4]heptane]-5-carboxamide To a solution of (5R)—N$^5$-((5-methylisoxazol-3-yl)methyl)-(6R)-6-methoxycarbonyl-(4S,7R)-[4,7-ethylene-spiro[2.4]heptane]-5-carboxamide (1.95 g, 6.12 mmol) in THF (40 mL) was added aq. 2N NaOH (15 mL, 30.00 mmol). The reaction mixture was stirred at rt until completion of the reaction. The mixture was then poured into aq. 1N HCl and extracted with EA (3×). The combined org. extracts were washed with brine, dried over MgSO$_4$, filtered, and concentrated under reduced pressure to give the title compound as a pale yellow solid. LC-MS-conditions 07: $t_R$=0.59 min; [M+H]$^+$=305.05.

Amide coupling (with (3-methylisoxazol-5-yl) methanamine)—formation of (5R)—N$^5$-((3-methyl isoxazol-5-yl)methyl)-(6R)-6-methoxycarbonyl-(4S, 7R)-[4,7-ethylene-spiro[2.4]heptane]-5-carboxamide In a flame dried round-bottomed flask equipped with a magnetic stir bar and under inert atmosphere (N$_2$), to a solution of (6R)-6-methoxycarbonyl-(4S,7R)-[4,7-ethylene-spiro[2.4]heptane]-(5R)-5-carboxylic acid (3.64 g, 16.00 mmol) in dry CH$_2$Cl$_2$ (20 mL) were added 6 drops of DMF and oxalyl chloride (1.64 mL, 19.00 mmol). The reaction mixture was stirred at rt for 120 minutes and concentrated under reduced pressure.

To a suspension of (3-methylisoxazol-5-yl)methanamine (2.40 g, 21.00 mmol) in pyridine (3.9 mL) was added a solution of the acyl chloride in acetone (11 mL). The reaction mixture was stirred at rt for 2 h, diluted with EA and successively washed with aq. 1N HCl, sat. aq. NaHCO$_3$ and brine. The org. layer was dried over MgSO$_4$, filtered, and concentrated under reduced pressure. The crude residue was purified by FC (hept-EA, 9:1→1:1) and the title compound obtained as a pale yellow solid. LC-MS-conditions 08: $t_R$=0.77 min; [M+H]$^+$=319.04.

(5R)—N$^5$-((3-Methyl isoxazol-5-yl)methyl)-(6R)-6-hydroxycarbonyl-(4S,7R)-[4,7-ethylene-spiro[2.4]heptane]-5-carboxamide To a solution of (5R)—N$^5$-((3-methylisoxazol-5-yl)methyl)-(6R)-6-methoxycarbonyl-(4S,7R)-[4,7-ethylene-spiro[2.4]heptane]-5-carboxamide (3.91 g, 12.28 mmol) in THF (78 mL) was added aq. 2N NaOH (43 mL, 86.00 mmol). The reaction mixture was stirred at rt until completion of the reaction. The mixture was then washed with Et$_2$O, poured into aq. 2N HCl and extracted with EA (3×). The combined org. extracts were washed with brine, dried over MgSO$_4$, filtered, and concentrated under reduced pressure to give the title compound as a white foam. LC-MS-conditions 08: $t_R$=0.67 min; [M+H]$^+$=305.01.

2-(2-(3,3-Difluoropyrrolidin-1-yl)ethoxy)ethanol

In a flame dried round-bottomed flask equipped with a magnetic stir bar and under inert atmosphere (N$_2$), to a solution of 3,3-difluoropyrrolidine hydrochloride (258 mg, 1.74 mmol) and 2-(2-chloroethoxy)ethanol (3.77 mL, 34.83 mmol) in dry toluene (10 mL) were added K$_2$CO$_3$ (1.32 g, 9.58 mmol) and KI (29 mg, 0.17 mmol). The reaction mixture was stirred at reflux for 2 d. The mixture was cooled down to rt, filtered and concentrated under reduced pressure. The crude residue was purified by FC(CH$_2$Cl$_2$/MeOH/NH$_4$OH, 1:0:0→98:2:0.5) and the title compound obtained as a pale yellow oil.

tert-Butyl 3,3-difluoro-4-(2-hydroxyethyl)piperidine-1-carboxylate

In a flame dried round-bottomed flask equipped with a magnetic stir bar and under inert atmosphere (N$_2$), to a solution of tert-butyl 4-(2-ethoxy-2-oxoethyl)-3,3-difluoropiperidine-1-carboxylate (177 mg, 0.57 mmol) in dry THF (5.8 mL) was added DIBAL-H (1.0 M solution in THF, 1.15 mL, 1.15 mmol) at 0° C. The reaction mixture was stirred at rt for 2 h. The mixture was cooled down to 0° C., successively treated with H$_2$O (0.23 mL) and 2N aq. NaOH (0.45 mL). The mixture was stirred at rt for 20 min, filtered through celite, washed with EA and the filtrate concentrated under reduced pressure. The crude residue was purified by FC (hept-EA, 1:1→1:2) and the title compound obtained as a colorless oil. LC-MS-conditions 08: $t_R$=0.74 min; [M-CH$_3$+H]$^+$=251.34.

tert-Butyl 4-(2-ethoxy-2-oxoethyl)-3,3-difluoropiperidine-1-carboxylate

In a flame dried round-bottomed flask equipped with a magnetic stir bar, a suspension of tert-butyl 4-(2-ethoxy-2-oxoethylidene)-3,3-difluoropiperidine-1-carboxylate (462 mg, 1.51 mmol) and Pd/C (10%, 70 mg) in dry EtOH (8 mL) was stirred at rt under a H$_2$ atmospheric pressure until completion of the reaction. The mixture was then filtered, washed with EA/EtOH, and the filtrate concentrated under reduced pressure. The crude residue was purified by FC (hept-EA, 1:0→1:1) and the title compound obtained as a colorless oil. LC-MS-conditions 08: $t_R$=0.89 min; [M-CH$_3$+H]$^+$=293.29.

tert-Butyl 4-(2-ethoxy-2-oxoethylidene)-3,3-difluoropiperidine-1-carboxylate

In a flame dried round-bottomed flask equipped with a magnetic stir bar and under inert atmosphere (N$_2$), to an ice-cold solution of tert-butyl 3,3-difluoro-4-hydroxypiperidine-1-carboxylate (2.40 g, 10.00 mmol) in dry $CH_2Cl_2$ (50 mL) was added a solution of Dess-Martin periodinane (50 mL of a 15% solution in $CH_2Cl_2$, 24.00 mmol). The reaction mixture was stirred at rt until completion of the reaction. Sat. aq. $NaHCO_3$ (50 mL) was then added followed by 10% aq. $Na_2SO_3$ (50 mL). The mixture was stirred at rt for 1 h, the layers separated and the aq. layer extracted with $CH_2Cl_2$ (3×). The combined org. extracts were dried over $MgSO_4$, filtered, and concentrated under reduced pressure. The crude residue was redissolved in $CH_2Cl_2$ (30 mL) and stirred in the presence of molecular sieves for 24 h, filtered and concentrated under reduced pressure to give tert-butyl 3,3-difluoro-4-oxopiperidine-1-carboxylate as a yellow solid.

In a flame dried round-bottomed flask equipped with a magnetic stir bar and under inert atmosphere ($N_2$), to NaH (45 mg, 1.12 mmol, 60% dispersion in oil washed with heptane) was added a solution of triethyl phosphonoacetate (262 mg, 1.17 mmol) in dry THF (10 mL) at 0° C. The reaction mixture was stirred at 0° C. for 30 min. Molecular sieves were then added followed by a solution of tert-butyl 3,3-difluoro-4-oxopiperidine-1-carboxylate (220 mg, 0.93 mmol) in THF (5 mL). The reaction mixture was stirred at 0° C. for 30 min and at rt for 1 h. Water was then added and the mixture extracted with EA (3×). The combined org. extracts were dried over $MgSO_4$, filtered, and concentrated under reduced pressure to give the title compound as a yellow oil (mixture of E and Z isomers). LC-MS-conditions 08: $t_R$=0.88 and 0.93 min; $[M-CH_3+H]^+$=291.27.

tert-Butyl 3,3-difluoro-4-hydroxypiperidine-1-carboxylate

In a flame dried round-bottomed flask equipped with a magnetic stir bar and under inert atmosphere ($N_2$), to a solution of 3,3-difluoropiperidin-4-ol (700 mg, 5.10 mmol) in dry $CH_2Cl_2$ (50 mL) was added $Boc_2O$ (1.11 g, 5.10 mmol). The reaction mixture was stirred at rt for 2 h. Water was then added, the layers separated and the aq. layer extracted with $CH_2Cl_2$ (3×). The combined org. extracts were washed with brine, dried over $MgSO_4$, filtered, and concentrated under reduced pressure to give the title compound as a yellow solid. LC-MS-conditions 08: $t_R$=0.69 min; $[M-CH_3+H]^+$=223.30.

3,3-Difluoropiperidin-4-ol

In a flame dried round-bottomed flask equipped with a magnetic stir bar, a suspension of 1-benzyl-3,3-difluoropiperidin-4-ol (1.73 g, 7.62 mmol) and $Pd(OH)_2$ (20% Pd, 107 mg) in dry EtOH (50 mL) was stirred at rt under a $H_2$ atmospheric pressure until completion of the reaction. The mixture was then filtered, washed with EA/EtOH, and the filtrate concentrated under reduced pressure to give the title compound as a beige solid.

1-Benzyl-3,3-difluoropiperidin-4-ol

In a flame dried round-bottomed flask equipped with a magnetic stir bar and under inert atmosphere ($N_2$), to a solution of 1-benzyl-3,3-difluoropiperidine-4,4-diol (WO2008/121687 and WO2005/040120) (2.88 g, 11.85 mmol) in dry MeOH (58 mL) was added $NaBH_4$ (672 mg, 17.76 mmol) portionwise at 0° C. The reaction mixture was stirred at 0° C. for 15 min. Aq. 0.1M $NaHCO_3$ (5 mL) was then added and the mixture further stirred for 5 min, dried ($MgSO_4$), filtered and concentrated under reduced pressure. The crude residue was purified by FC (hept-EA, 2:1→1:1) and the title compound obtained as a beige oil. LC-MS-conditions 08: $t_R$=0.42 min; $[M+H]^+$=228.32.

cis-tert-Butyl 3-fluoro-4-(2-hydroxyethyl)piperidine-1-carboxylate

In a flame dried round-bottomed flask equipped with a magnetic stir bar, a suspension of tert-butyl 4-(2-ethoxy-2-oxoethylidene)-3-fluoropiperidine-1-carboxylate (WO2010/056633) (2.17 g, 7.55 mmol) and Pd/C (10% Pd, 217 mg) in dry EtOH (7 mL) was stirred at rt under a $H_2$ atmospheric pressure until completion of the reaction. The mixture was then filtered, washed with EA/EtOH, and the filtrate concentrated under reduced pressure. The crude residue was purified by FC (hept-EA, 6:1) to give cis-tert-butyl 4-(2-ethoxy-2-oxoethyl)-3-fluoropiperidine-1-carboxylate as a pale yellow oil. LC-MS-conditions 08: $t_R$=0.86 min; $[M-CH_3+H]^+$=275.32.

In a flame dried round-bottomed flask equipped with a magnetic stir bar and under inert atmosphere ($N_2$), to an ice-cold solution of tert-butyl 4-(2-ethoxy-2-oxoethyl)-3-fluoropiperidine-1-carboxylate (348 mg, 1.20 mmol) in dry THF (9 mL) was added DIBAL-H (2.41 mL of a 1M solution in toluene, 2.41 mmol). The reaction mixture was stirred at rt for 2 h. DIBAL-H (0.60 mL of a 1M solution in toluene, 0.60 mmol) was added again and the reaction mixture further stirred at rt for 1 h before being cooled to 0° C. Water (0.15 mL) was added followed by aq. 2N NaOH (0.30 mL). The mixture was stirred for 20 min, filtered through celite, washed with EA and concentrated under reduced pressure. The crude residue was purified by FC (hept-EA, 7:3→1:1) to give the title compound as a colorless oil. LC-MS-conditions 08: $t_R$=0.69 min; $[M-CH_3+H]^+$=233.35.

trans-tert-Butyl 3-fluoro-4-(hydroxymethyl)piperidine-1-carboxylate and cis-tert-butyl 3-fluoro-4-(hydroxymethyl)piperidine-1-carboxylate In a flame dried round-bottomed flask equipped with a magnetic stir bar and under inert atmosphere ($N_2$), to a solution of tert-butyl 3-fluoro-4-methylenepiperidine-1-carboxylate (545 mg, 2.53 mmol) in THF (17 mL) was added dropwise a 0.5 M solution of 9-BBN (12.7 ml) at 0° C. The resulting solution was stirred for 16 h at rt. A solution of NaOAc 5M in water (1.7 mL) was added followed by $H_2O_2$ 30% (1.7 mL), and the mixture was stirred for 14 h at rt. The mixture was then partitioned between EA and aq. sat. $NaHCO_3$. The aqueous layer was extracted with EA, and the combined organic extracts were washed with brine, dried over $MgSO_4$, filtered, and concentrated under reduced pressure. The residue was purified by FC (hexanes-EA, 3:2) to afford cis-tert-butyl 3-fluoro-4-(hydroxymethyl)piperidine-1-carboxylate as a colorless oil and trans-tert-butyl 3-fluoro-4-(hydroxymethyl)piperidine-1-carboxylate as a colorless oil. LC-MS-conditions 08: $t_R$=0.65 min; $[M-CH_3+H]^+$=220.35 and $t_R$=0.68 min; $[M-CH_3+H]^+$=220.36.

tert-Butyl 3-fluoro-4-methylenepiperidine-1-carboxylate

In a flame dried round-bottomed flask equipped with a magnetic stir bar and under inert atmosphere ($N_2$), to a suspension of methyltriphenylphosphonium bromide (1.68 g, 4.60 mmol) in dry THF (30 mL) was added potassium tert-butoxide (544 mg, 4.60 mmol) at rt. The reaction mixture was stirred at rt for 30 min. A solution of tert-butyl 3-fluoro-4- oxopiperidine-1-carboxylate (500 mg, 2.30 mmol) in dry THF (10 mL) was then added and the resulting suspension stirred at rt for 16 h. Aq. 10% NaHSO$_3$ was then added, the mixture extracted with EA. The org. layer was dried over MgSO$_4$, filtered, and concentrated under reduced pressure. The residue was purified by FC (hexanes-EA, 19:1) to afford the title compound as a colorless oil. LC-MS-conditions 08: $t_R$=0.84 min; [M−CH$_3$+H]$^+$=201.33.

tert-Butyl 3-fluoro-4-oxopiperidine-1-carboxylate

In a flame dried round-bottomed flask equipped with a magnetic stir bar and under inert atmosphere (N$_2$), to a solution of tert-butyl 4-oxopiperidine-1-carboxylate (5.00 g, 25.09 mmol) in dry DMF (25 mL) was added trimethylsilyl chloride (5.77 mL, 45.17 mmol) followed by Et$_3$N (8.38 mL, 60.23 mmol) at rt. The reaction mixture was stirred at 80° C. for 24 h. The mixture was then cooled to rt, diluted with hexanes and washed with sat. aq. NaHCO$_3$. The layers were separated and the org. layer dried over MgSO$_4$, filtered, and concentrated under reduced pressure. The residue was purified by FC (hexanes-EA, 9:1) to afford tert-butyl 4-((trimethylsilyl)oxy)-5,6-dihydropyridine-1(2H)-carboxylate as a colorless oil.

In a flame dried round-bottomed flask equipped with a magnetic stir bar and under inert atmosphere (N$_2$), to a solution of tert-butyl 4-((trimethylsilyl)oxy)-5,6-dihydropyridine-1(2H)-carboxylate (5.30 g, 19.53 mmol) in dry acetonitrile (25 mL) was added Selectfluor® (8.01 g, 21.48 mmol) at rt. The reaction mixture was stirred at rt for 2 h then poured into EA and successively washed with aq. 1% NaHCO$_3$ and brine. The org. layer was dried over MgSO$_4$, filtered, and concentrated under reduced pressure. The residue was purified by FC (hexanes-EA, 4:1) to afford the title compound as a pale yellow solid. LC-MS-conditions 08: $t_R$=0.55 min.

tert-Butyl
4-fluoro-4-(hydroxymethyl)piperidine-1-carboxylate

In a flame dried round-bottomed flask equipped with a magnetic stir bar and under inert atmosphere (N$_2$), to an ice-cold solution of tert-butyl 1-oxa-6-azaspiro[2.5]octane-6-carboxylate (2.50 g, 11.72 mmol) in dry CH$_2$Cl$_2$ (20 mL) was added HF.Pyridine (1.00 mL, 8.20 mmol). The mixture was stirred at 0° C. for 1 h, then more HF.Pyridine (0.50 mL, 4.10 mmol) was added and the mixture further stirred at 0° C. for 1 h. Ice-water (100 mL) was then added followed by 2N aq. NaOH to reach neutral pH. The layers were separated and the aq. layer extracted with CH$_2$Cl$_2$ (3×). The combined org. extracts were dried over MgSO$_4$, filtered, and concentrated under reduced pressure. The residue was purified by FC (hept-EA, 1:0→1:1) to afford the title compound as a colorless oil. LC-MS-conditions 08: $t_R$=0.66 min.

4,4-Difluoro-5-(pyrrolidin-1-yl)pentan-2-ol and 4,4-difluoro-5-(pyrrolidin-1-yl)pentan-1-ol In a flame dried round-bottomed flask equipped with a magnetic stir bar and under inert atmosphere (N$_2$), to a solution of 2,2-difluoro-1-(pyrrolidin-1-yl)pent-4-en-1-one (260 mg, 1.37 mmol) in dry THF (15 mL) was added BH$_3$-THF (6.6 mL of a 1M solution in THF, 6.60 mmol) at rt. The reaction mixture was stirred at reflux for 18 h, cooled down to rt and concentrated under reduced pressure. The residue was redissolved in MeOH (slow addition) and concentrated under reduced pressure (2×). The resulting oil was then redissolved in THF (5 mL), treated with aq. 2N NaOH (0.8 mL) and aq. 30% H$_2$O$_2$ (0.8 mL). The mixture was stirred at rt for 2 h. Water was then added, the layers separated and the aq. layer extracted with EA. The combined org. extracts were washed with brine, dried (MgSO$_4$), filtered and concentrated under reduced pressure. The crude residue was purified by FC (hept-EA, 1:1→3:7) to give 4,4-difluoro-5-(pyrrolidin-1-yl)pentan-2-ol as a colorless oil and 4,4-difluoro-5-(pyrrolidin-1-yl)pentan-1-ol as a yellow oil. LC-MS-conditions 08: $t_R$=0.38 min; [M+H]$^+$=194.39 and $t_R$=0.51 min; [M+H]$^+$=194.38.

2,2-Difluoro-1-(pyrrolidin-1-yl)pent-4-en-1-one

In a flame dried round-bottomed flask equipped with a magnetic stir bar and under inert atmosphere (N$_2$), to a solution of 2-bromo-2,2-difluoro-1-(pyrrolidin-1-yl)ethanone (600 mg, 2.63 mmol) in dry toluene (18 mL) was added allyltributyltin (0.84 mL, 2.63 mmol) and AIBN (9 mg, 0.05 mmol) at rt. The reaction mixture was stirred at 100° C. for 1 h. AIBN (9 mg, 0.05 mmol) was then added again and the reaction mixture further stirred at 100° C. for 30 h. The solvent was removed under reduced pressure and the crude residue purified by FC (SiO$_2$ containing 10% KF, hept-EA, 1:0→4:1) to give the title compound as a colorless oil. LC-MS-conditions 08: $t_R$=0.73 min; [M+H]$^+$=190.30.

2-Bromo-2,2-difluoro-1-(pyrrolidin-1-yl)ethanone

In a flame dried round-bottomed flask equipped with a magnetic stir bar and under inert atmosphere (N$_2$), ethyl bromodifluoroacetate (0.88 mL, 6.89 mmol) was added dropwise to pyrrolidine (0.58 mL, 6.89 mmol) at rt. The reaction mixture was stirred at 50° C. for 2 h and at rt for 18 h. The mixture was then filtered through silica and the title compound obtained as a colorless oil. LC-MS-conditions 08: $t_R$=0.70 min; [M+H]$^+$=228.01.

(S)-4-(3-Fluoropyrrolidin-1-yl)butanol

In a flame dried round-bottomed flask equipped with a magnetic stir bar and under inert atmosphere (N$_2$), a suspension of 4-bromo-1-butanol (187 mg, 1.20 mmol), (S)-3-fluoropyrrolidine (186 mg, 1.44 mmol) and K$_2$CO$_3$ (392 mg, 1.56 mmol) in CH$_3$CN (8 mL) was heated to 100° C. under microwave irradiations for 25 min. The mixture was then filtered and the solvent removed under reduced pressure to give the title compound as a colorless oil.

4-Hydroxy-1-(pyrrolidin-1-yl)butan-1-one

In a flame dried round-bottomed flask equipped with a magnetic stir bar and under inert atmosphere (N$_2$), a solution of 4-benzyloxybutyric acid (246 mg, 1.27 mmol), pyrrolidine (0.13 mL, 1.52 mmol), EDC.HCl (493 mg, 2.53 mmol), HOBt (262 mg, 1.90 mL) and DIPEA (0.65 mL, 3.80 mmol) in CH$_2$Cl$_2$ (10 mL) was heated at rt until completion of the reaction. Water was added, the layers separated and the aq. layer extracted with CH$_2$Cl$_2$ (2×). The combined org. extracts were washed with brine, dried (MgSO$_4$), filtered and concentrated under reduced pressure. The crude residue was purified by FC (hept-EA, 1:0→0:1) to give 4-(benzyloxy)-1-(pyrrolidin-1-yl)butan-1-one as a colorless oil. LC-MS-conditions 08: $t_R$=0.77 min; [M+H]$^+$=247.95.

In a flame dried round-bottomed flask equipped with a magnetic stir bar, a suspension of 4-(benzyloxy)-1-(pyrrolidin-1-yl)butan-1-one (284 mg, 1.15 mmol) and Pd/C (10% Pd, 122 mg) in dry MeOH (10 mL) was stirred at rt under a H$_2$ atmospheric pressure until completion of the reaction. The mixture was then filtered, and the filtrate concentrated under reduced pressure to give the title compound as a colorless oil.
LC-MS-conditions 08: $t_R$=0.41 min; [M+H]$^+$=158.07.

3-Hydroxypropanamide

In a flame dried round-bottomed flask equipped with a magnetic stir bar and under inert atmosphere (N$_2$), to an ice-cold solution of ethyl 3-amino-3-oxopropanoate (1.00 g, 7.25 mmol) in EtOH (40 mL) was added NaBH$_4$ (1.02 g, 26.42 mmol). The reaction mixture was stirred at rt for 24 h, filtered and the filtrate quenched by slow addition of H$_2$O at 0° C. The mixture was stirred at rt for 15 min, concentrated under reduced pressure and co-evaporated with toluene (3×). The crude residue was suspended in 2-butanone and the solid filtered off. This operation was repeated twice to give the title compound as a pale yellow oil.

Preparation of Examples

Example 1

(1S,2R,3R,4R)-[Piperidin-4-ylmethyl 2-((6-bromopyridin-3-yl)carbamoyl)spiro[bicyclo[2.2.1]heptane-7,1'-cyclopropane]-3-carboxylate]

Following general procedures A then D, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and tert-butyl 4-(hydroxymethyl)piperidine-1-carboxylate.
LC-MS-conditions FA: $t_R$=0.63 min; [M+H]$^+$=462.20.

Example 2

(1S,2R,3R,4R)-[Piperidin-4-yl 2-((6-bromopyridin-3-yl)carbamoyl)spiro[bicyclo[2.2.1]heptane-7,1'-cyclopropane]-3-carboxylate]

Following general procedures A then D, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and tert-butyl 4-hydroxypiperidine-1-carboxylate.
LC-MS-conditions FA: $t_R$=0.61 min; [M+H]$^+$=448.20.

Example 3

(1S,2R,3R,4R)-[Piperidin-4-ylmethyl 2-(((5-methylisoxazol-3-yl)methyl)carbamoyl)spiro[bicyclo[2.2.1]heptane-7,1'-cyclopropane]-3-carboxylate]hydrochloride Following general procedures A then D, starting from (5R)—N$^5$-((5-methylisoxazol-3-yl)methyl)-(6R)-6-hydroxycarbonyl-(4S,7R)-[4,7-ethylene-spiro[2.4]heptane]-5-carboxamide and tert-butyl 4-(hydroxymethyl)piperidine-1-carboxylate.
LC-MS-conditions FA: $t_R$=0.52 min; [M+H]$^+$=402.30.

Example 4

(1S,2R,3R,4R)-[Piperidin-4-ylmethyl 2-((4-bromo-2-fluorobenzyl)carbamoyl)spiro[bicyclo[2.2.1]heptane-7,1'-cyclopropane]-3-carboxylate]hydrochloride Following general procedures A then D, starting from (5R)—N$^5$-(4-bromo-2-fluorophenyl-methyl)-(6R)-6-hydroxycarbonyl-(4S,7R)-[4,7-ethylene-spiro[2.4]heptane]-5-carboxamide and tert-butyl 4-(hydroxymethyl)piperidine-1-carboxylate.
LC-MS-conditions FA: $t_R$=0.70 min; [M+H]$^+$=493.20.

Example 5

(1S,2R,3R,4R)-[(S*)-2,3-Dihydroxypropyl 2-((6-bromopyridin-3-yl)carbamoyl)spiro[bicyclo[2.2.1]heptane-7,1'-cyclopropane]-3-carboxylate]

Following general procedures A then E, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and (S*)-(2,2-dimethyl-1,3-dioxolan-4-yl)methanol.
LC-MS-conditions FA: $t_R$=0.82 min; [M+H]$^+$=439.10.

Example 6

(1S,2R,3R,4R)-[1-Methylpiperidin-4-yl 2-((6-bromopyridin-3-yl)carbamoyl)spiro[bicyclo[2.2.1]heptane-7,1'-cyclopropane]-3-carboxylate]

Following general procedure A, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and 1-methylpiperidin-4-ol.
LC-MS-conditions FA: $t_R$=0.61 min; [M+H]$^+$=462.20.

Example 7

(1S,2R,3R,4R)-[2-Methoxyethyl 2-((6-bromopyridin-3-yl)carbamoyl)spiro[bicyclo[2.2.1]heptane-7,1'-cyclopropane]-3-carboxylate]

Following general procedure A, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and 2-methoxyethanol.
LC-MS-conditions FA: $t_R$=1.03 min; [M+H]$^+$=423.10.

Example 8

(1S,2R,3R,4R)-[1,2,2,6,6-Pentamethyl piperidin-4-yl 2-((6-bromopyridin-3-yl)carbamoyl)spiro[bicyclo[2.2.1]heptane-7,1'-cyclopropane]-3-carboxylate]

Following general procedure A, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and 1,2,2,6,6-pentamethylpiperidin-4-ol.
LC-MS-conditions FA: $t_R$=0.68 min; [M+H]$^+$=518.20.

Example 9

(1S,2R,3R,4R)-[Piperidin-3-yl 2-((6-bromopyridin-3-yl)carbamoyl)spiro[bicyclo[2.2.1]heptane-7,1'-cyclopropane]-3-carboxylate]hydrochloride Following general procedures B then D, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and tert-butyl 3-hydroxypiperidine-1-carboxylate.
LC-MS-conditions FA: $t_R$=0.60 min; [M+H]$^+$=448.20.

Example 10

(1S,2R,3R,4R)-[2-(Piperidin-3-yl)ethyl 2-((6-bromopyridin-3-yl)carbamoyl)spiro[bicyclo[2.2.1]heptane-7,1'-cyclopropane]-3-carboxylate]hydrochloride Following general procedures B then D, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and tert-butyl 3-(2-hydroxyethyl)piperidine-1-carboxylate.

LC-MS-conditions FA: $t_R$=0.66 min; [M+H]$^+$=476.20.

Example 11

(1S,2R,3R,4R)-[(S)-2-(Piperidin-2-yl)ethyl 2-((6-bromopyridin-3-yl)carbamoyl)spiro[bicyclo[2.2.1]heptane-7,1'-cyclopropane]-3-carboxylate]hydrochloride Following general procedures B then D, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and (S)-tert-butyl 2-(2-hydroxyethyl)piperidine-1-carboxylate.

LC-MS-conditions FA: $t_R$=0.65 min; [M+H]$^+$=476.20.

Example 12

(1S,2R,3R,4R)-[Piperidin-3-ylmethyl 2-((6-bromopyridin-3-yl)carbamoyl)spiro[bicyclo[2.2.1]heptane-7,1'-cyclopropane]-3-carboxylate]hydrochloride Following general procedures B then D, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and tert-butyl 3-(hydroxymethyl)piperidine-1-carboxylate.

LC-MS-conditions FA: $t_R$=0.62 min; [M+H]$^+$=462.20.

Example 13

(1S,2R,3R,4R)-[(R)-Pyrrolidin-3-yl 2-((6-bromopyridin-3-yl)carbamoyl)spiro[bicyclo[2.2.1]heptane-7,1'-cyclopropane]-3-carboxylate]hydrochloride Following general procedures B then D, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and (R)-tert-butyl 3-hydroxypyrrolidine-1-carboxylate.

LC-MS-conditions FA: $t_R$=0.59 min; [M+H]$^+$=434.20.

Example 14

(1S,2R,3R,4R)-[1-Methylpyrrolidin-3-yl 2-((6-bromopyridin-3-yl)carbamoyl)spiro[bicyclo[2.2.1]heptane-7,1'-cyclopropane]-3-carboxylate]

Following general procedure B, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and 1-methylpyrrolidin-3-ol.

LC-MS-conditions FA: $t_R$=0.60 min; [M+H]$^+$=448.20.

Example 15

(1S,2R,3R,4R)-[1-Methylpyrrolidin-3-yl 2-(((5-methylisoxazol-3-yl)methyl)carbamoyl)spiro[bicyclo[2.2.1]heptane-7,1'-cyclopropane]-3-carboxylate]

Following general procedure B, starting from (5R)—N$^5$-((5-methylisoxazol-3-yl)methyl)-(6R)-6-hydroxycarbonyl-(4S,7R)-[4,7-ethylene-spiro[2.4]heptane]-5-carboxamide and 1-methylpyrrolidin-3-ol.

LC-MS-conditions FA: $t_R$=0.49 min; [M+H]$^+$=388.00.

Example 16

(1S,2R,3R,4R)-[Piperidin-3-yl 2-(((5-methylisoxazol-3-yl)methyl)carbamoyl)spiro[bicyclo[2.2.1]heptane-7,1'-cyclopropane]-3-carboxylate]hydrochloride Following general procedures B then D, starting from (5R)—N$^5$-((5-methylisoxazol-3-yl)methyl)-(6R)-6-hydroxycarbonyl-(4S,7R)-[4,7-ethylene-spiro[2.4]heptane]-5-carboxamide and tert-butyl 3-hydroxypiperidine-1-carboxylate.

LC-MS-conditions FA: $t_R$=0.50 min; [M+H]$^+$=388.30.

Example 17

(1S,2R,3R,4R)-[2-(Piperidin-3-yl)ethyl 2-(((5-methylisoxazol-3-yl)methyl)carbamoyl)spiro[bicyclo[2.2.1]heptane-7,1'-cyclopropane]-3-carboxylate]hydrochloride Following general procedures B then D, starting from (5R)—N$^5$-((5-methylisoxazol-3-yl)methyl)-(6R)-6-hydroxycarbonyl-(4S,7R)-[4,7-ethylene-spiro[2.4]heptane]-5-carboxamide and tert-butyl 3-(2-hydroxyethyl)piperidine-1-carboxylate.

LC-MS-conditions FA: $t_R$=0.55 min; [M+H]$^+$=416.30.

Example 18

(1S,2R,3R,4R)-[Piperidin-3-ylmethyl 2-(((5-methylisoxazol-3-yl)methyl)carbamoyl)spiro[bicyclo[2.2.1]heptane-7,1'-cyclopropane]-3-carboxylate]hydrochloride Following general procedures B then D, starting from (5R)—N$^5$-((5-methylisoxazol-3-yl)methyl)-(6R)-6-hydroxycarbonyl-(4S,7R)-[4,7-ethylene-spiro[2.4]heptane]-5-carboxamide and tert-butyl 3-(hydroxymethyl)piperidine-1-carboxylate.

LC-MS-conditions FA: $t_R$=0.52 min; [M+H]$^+$=402.30.

Example 19

(1S,2R,3R,4R)-[(R)-Pyrrolidin-3-yl 2-(((5-methylisoxazol-3-yl)methyl)carbamoyl)spiro[bicyclo[2.2.1]heptane-7,1'-cyclopropane]-3-carboxylate]hydrochloride Following general procedures B then D, starting from (5R)—N$^5$-((5-methylisoxazol-3-yl)methyl)-(6R)-6-hydroxycarbonyl-(4S,7R)-[4,7-ethylene-spiro[2.4]heptane]-5-carboxamide and (R)-tert-butyl 3-hydroxypyrrolidine-1-carboxylate.

LC-MS-conditions FA: $t_R$=0.49 min; [M+H]$^+$=374.30.

Example 20

(1S,2R,3R,4R)-[(S)-2-(Piperidin-2-yl)ethyl 2-(((5-methylisoxazol-3-yl)methyl)carbamoyl)spiro[bicyclo[2.2.1]heptane-7,1'-cyclopropane]-3-carboxylate] hydrochloride Following general procedures B then D, starting from (5R)—$N^5$-((5-methylisoxazol-3-yl)methyl)-(6R)-6-hydroxycarbonyl-(4S,7R)-[4,7-ethylene-spiro[2.4]heptane]-5-carboxamide and (S)-tert-butyl 2-(2-hydroxyethyl)piperidine-1-carboxylate.

LC-MS-conditions FA: $t_R$=0.55 min; [M+H]$^+$=416.30.

Example 21

(1S,2R,3R,4R)-[1-Dimethylaminoprop-3-yl 2-((6-bromopyridin-3-yl)carbamoyl)spiro[bicyclo[2.2.1]heptane-7,1'-cyclopropane]-3-carboxylate]

Following general procedure B, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and 3-(dimethylamino)propan-1-ol.

LC-MS-conditions FA: $t_R$=0.61 min; [M+H]$^+$=450.20.

Example 22

(1S,2R,3R,4R)-[1-Methyl-piperidin-2-ylmethyl 2-((6-bromopyridin-3-yl)carbamoyl)spiro[bicyclo[2.2.1]heptane-7,1'-cyclopropane]-3-carboxylate]

Following general procedure B, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and (1-methylpiperidin-2-yl)methanol.

LC-MS-conditions FA: $t_R$=0.63 min; [M+H]$^+$=476.20.

Example 23

(1S,2R,3R,4R)-[2-(2-Oxopyrrolidin-1-yl)ethyl 2-((6-bromopyridin-3-yl)carbamoyl)spiro[bicyclo[2.2.1]heptane-7,1'-cyclopropane]-3-carboxylate]

Following general procedure B, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and 1-(2-hydroxyethyl)pyrrolidin-2-one.

LC-MS-conditions FA: $t_R$=0.95 min; [M+H]$^+$=476.10.

Example 24

(1S,2R,3R,4R)-[Azetidin-3-yl 2-((6-bromopyridin-3-yl)carbamoyl)spiro[bicyclo[2.2.1]heptane-7,1'-cyclopropane]-3-carboxylate]hydrochloride Following general procedures B then D, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and tert-butyl 3-hydroxyazetidine-1-carboxylate.

LC-MS-conditions FA: $t_R$=0.59 min; [M+H]$^+$=420.20.

Example 25

(1S,2R,3R,4R)-[1-Dimethylaminoprop-3-yl 2-(((5-methylisoxazol-3-yl)methyl)carbamoyl)spiro[bicyclo[2.2.1]heptane-7,1'-cyclopropane]-3-carboxylate]

Following general procedure B, starting from (5R)—$N^5$-((5-methylisoxazol-3-yl)methyl)-(6R)-6-hydroxycarbonyl-(4S,7R)-[4,7-ethylene-spiro[2.4]heptane]-5-carboxamide and 3-(dimethylamino)propan-1-ol.

LC-MS-conditions FA: $t_R$=0.50 min; [M+H]$^+$=390.30.

Example 26

(1S,2R,3R,4R)-[1-Methyl-piperidin-2-ylmethyl 2-(((5-methyl isoxazol-3-yl)methyl)carbamoyl)spiro[bicyclo[2.2.1]heptane-7,1'-cyclopropane]-3-carboxylate]

Following general procedure B, starting from (5R)—$N^5$-((5-methylisoxazol-3-yl)methyl)-(6R)-6-hydroxycarbonyl-(4S,7R)-[4,7-ethylene-spiro[2.4]heptane]-5-carboxamide and (1-methylpiperidin-2-yl)methanol.

LC-MS-conditions FA: $t_R$=0.52 min; [M+H]$^+$=416.30.

Example 27

(1S,2R,3R,4R)-[1-Dimethylaminoeth-2-yl 2-(((5-methylisoxazol-3-yl)methyl)carbamoyl)spiro[bicyclo[2.2.1]heptane-7,1'-cyclopropane]-3-carboxylate]

Following general procedure B, starting from (5R)—$N^5$-((5-methylisoxazol-3-yl)methyl)-(6R)-6-hydroxycarbonyl-(4S,7R)-[4,7-ethylene-spiro[2.4]heptane]-5-carboxamide and 2-(dimethylamino)ethan-1-ol.

LC-MS-conditions FA: $t_R$=0.48 min; [M+H]$^+$=376.30.

Example 28

(1S,2R,3R,4R)-[Isobutyl 2-(((5-methyl isoxazol-3-yl)methyl)carbamoyl)spiro[bicyclo[2.2.1]heptane-7,1'-cyclopropane]-3-carboxylate]

Following general procedure B, starting from (5R)—$N^5$-((5-methylisoxazol-3-yl)methyl)-(6R)-6-hydroxycarbonyl-(4S,7R)-[4,7-ethylene-spiro[2.4]heptane]-5-carboxamide and 2-methylpropan-1-ol.

LC-MS-conditions FA: $t_R$=1.06 min; [M+H]$^+$=361.30.

Example 29

(1S,2R,3R,4R)-[Cyclopentyl 2-(((5-methylisoxazol-3-yl)methyl)carbamoyl)spiro[bicyclo[2.2.1]heptane-7,1'-cyclopropane]-3-carboxylate]

Following general procedure B, starting from (5R)—$N^5$-((5-methylisoxazol-3-yl)methyl)-(6R)-6-hydroxycarbonyl-(4S,7R)-[4,7-ethylene-spiro[2.4]heptane]-5-carboxamide and cyclopentanol.

LC-MS-conditions FA: $t_R$=1.07 min; [M+H]$^+$=373.30.

Example 30

(1S,2R,3R,4R)-[Propyl 2-(((5-methyl isoxazol-3-yl)methyl)carbamoyl)spiro[bicyclo[2.2.1]heptane-7,1'-cyclopropane]-3-carboxylate]

Following general procedure B, starting from (5R)—$N^5$-((5-methylisoxazol-3-yl)methyl)-(6R)-6-hydroxycarbonyl-(4S,7R)-[4,7-ethylene-spiro[2.4]heptane]-5-carboxamide and propanol.

LC-MS-conditions FA: $t_R$=1.00 min; [M+H]$^+$=347.30.

Example 31

(1S,2R,3R,4R)-[2-(2-(Pyrrolidin-1-yl)ethoxy)ethyl 2-((6-bromopyridin-3-yl)carbamoyl)spiro[bicyclo[2.2.1]heptane-7,1'-cyclopropane]-3-carboxylate]

Following general procedure A, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and 2-(2-(pyrrolidin-1-yl)ethoxy)ethanol.
LC-MS-conditions 07: $t_R$=0.66 min; [M+H]$^+$=505.92.

Example 32

(1S,2R,3R,4R)-[2-(2-(Pyrrolidin-1-yl)ethoxy)ethyl 2-((4-bromo-2-fluorobenzyl)carbamoyl)spiro[bicyclo[2.2.1]heptane-7,1'-cyclopropane]-3-carboxylate]

Following general procedure A, starting from (5R)—$N^5$-(4-bromo-2-fluorophenyl-methyl)-(6R)-6-hydroxycarbonyl-(4S,7R)-[4,7-ethylene-spiro[2.4]heptane]-5-carboxamide and 2-(2-(pyrrolidin-1-yl)ethoxy)ethanol.
LC-MS-conditions 07: $t_R$=0.73 min; [M+H]$^+$=536.85.

Example 33

(1S,2R,3R,4R)-[2-(2-(Pyrrolidin-1-yl)ethoxy)ethyl 2-(((5-methylisoxazol-3-yl)methyl)carbamoyl)spiro[bicyclo[2.2.1]heptane-7,1'-cyclopropane]-3-carboxylate]

Following general procedure A, starting from (5R)—$N^5$-((5-methylisoxazol-3-yl)methyl)-(6R)-6-hydroxycarbonyl-(4S,7R)-[4,7-ethylene-spiro[2.4]heptane]-5-carboxamide and 2-(2-(pyrrolidin-1-yl)ethoxy)ethanol.
LC-MS-conditions 07: $t_R$=0.55 min; [M+H]$^+$=446.22.

Example 34

(1S,2R,3R,4R)-[(S)-2-(2-(3-Fluoropyrrolidin-1-yl)ethoxy)ethyl 2-(((5-methyl isoxazol-3-yl)methyl)carbamoyl)spiro[bicyclo[2.2.1]heptane-7,1'-cyclopropane]-3-carboxylate]

Following general procedure A, starting from (5R)—$N^5$-((5-methylisoxazol-3-yl)methyl)-(6R)-6-hydroxycarbonyl-(4S,7R)-[4,7-ethylene-spiro[2.4]heptane]-5-carboxamide and (S)-2-(2-(3-fluoropyrrolidin-1-yl)ethoxy)ethanol.
LC-MS-conditions 07: $t_R$=0.55 min; [M+H]$^+$=464.29.

Example 35

(1R,4S,5R,6R)-[Piperidin-4-ylmethyl 5-((4-bromophenyl)carbamoyl)spiro[bicyclo[2.2.1]hept[2]ene-7,1'-cyclopropane]-6-carboxylate]

Following general procedures A then D, starting from (5R)—$N^5$-(4-bromo-phenyl)-(6R)-6-hydroxycarbonyl-(4S,7R)-[4,7-ethenylene-spiro[2.4]heptane]-5-carboxamide and tert-butyl 4-(hydroxymethyl)piperidine-1-carboxylate.
LC-MS-conditions 07: $t_R$=0.68 min; [M+H]$^+$=459.10.

Example 36

(1S,2R,3R,4R)-[2-(Piperidin-4-yl)ethyl 2-((6-bromopyridin-3-yl)carbamoyl)spiro[bicyclo[2.2.1]heptane-7,1'-cyclopropane]-3-carboxylate]hydrochloride Following general procedures A and D, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and tert-butyl-4-(2-hydroxyethyl)piperidine-1-carboxylate.
LC-MS-conditions 07: $t_R$=0.68 min; [M+H]$^+$=476.12.

Example 37

(1S,2R,3R,4R)-[2-(piperazin-1-yl)ethyl 2-((6-bromopyridin-3-yl)carbamoyl)spiro[bicyclo[2.2.1]heptane-7,1'-cyclopropane]-3-carboxylate]dihydrochloride Following general procedures A and D, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and tert-butyl-4-(2-hydroxyethyl)piperazine-1-carboxylate.
LC-MS-conditions TFA: $t_R$=0.67 min; [M+H]$^+$=477.20.

Example 38

(1S,2R,3R,4R)-[2-(cis-3-Fluoro-piperidin-4-yl)ethyl 2-((6-bromopyridin-3-yl)carbamoyl)spiro[bicyclo[2.2.1]heptane-7,1'-cyclopropane]-3-carboxylate]

Following general procedures A and D, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and cis-tert-butyl 3-fluoro-4-(2-hydroxyethyl)piperidine-1-carboxylate.
LC-MS-conditions 08: $t_R$=0.70 min; [M+H]$^+$=494.35.

Example 39

(1S,2R,3R,4R)-[2-(cis-3-Fluoro-piperidin-4-yl)ethyl 2-(((3-methylisoxazol-5-yl)methyl)carbamoyl)spiro[bicyclo[2.2.1]heptane-7,1'-cyclopropane]-3-carboxylate]

Following general procedures A and D, starting from (5R)—$N^5$-((3-methylisoxazol-5-yl)methyl)-(6R)-6-hydroxycarbonyl-(4S,7R)-[4,7-ethylene-spiro[2.4]heptane]-5-carboxamide and cis-tert-butyl 3-fluoro-4-(2-hydroxyethyl)piperidine-1-carboxylate.
LC-MS-conditions 08: $t_R$=0.63 min; [M+H]$^+$=434.28.

Example 40

(1S,2R,3R,4R)-[2-(4-Fluoro-piperidin-4-yl)ethyl 2-((6-bromopyridin-3-yl)carbamoyl)spiro[bicyclo[2.2.1]heptane-7,1'-cyclopropane]-3-carboxylate]

Following general procedures A and D, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and tert-butyl 4-fluoro-4-(2-hydroxyethyl)piperidine-1-carboxylate (WO2010/081859).
LC-MS-conditions TFA: $t_R$=0.80 min; [M+H]$^+$=494.30

Example 41

(1S,2R,3R,4R)-[(Piperidin-4-yl)methyl 2-((6-bromopyridin-3-yl)carbamoyl)spiro[bicyclo[2.2.1]heptane-7,1'-cyclopropane]-3-carboxylate]hydrochloride Following general procedures A and D, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and tert-butyl-4-(hydroxymethyl)piperidine-1-carboxylate.
LC-MS-conditions 07: $t_R$=0.64 min; [M+H]$^+$=461.94.

Example 42

(1S,2R,3R,4R)-[(S)-2-(2-(3-Fluoropyrrolidin-1-yl)ethoxy)ethyl 2-(((3-methyl isoxazol-5-yl)methyl)carbamoyl)spiro[bicyclo[2.2.1]heptane-7,1'-cyclopropane]-3-carboxylate]

Following general procedure A, starting from (5R)—N$^5$-((3-methylisoxazol-5-yl)methyl)-(6R)-6-hydroxycarbonyl-(4S,7R)-[4,7-ethylene-spiro[2.4]heptane]-5-carboxamide and (S)-2-(2-(3-fluoropyrrolidin-1-yl)ethoxy)ethanol.
LC-MS-conditions 08: $t_R$=0.64 min; [M+H]$^+$=464.40.

Example 43

(1S,2R,3R,4R)-[(trans-3-Fluoro-piperidin-4-yl)methyl 2-(((3-methylisoxazol-5-yl)methyl)carbamoyl)spiro[bicyclo[2.2.1]heptane-7,1'-cyclopropane]-3-carboxylate]

Following general procedures A and D, starting from (5R)—N$^5$-((3-methylisoxazol-5-yl)methyl)-(6R)-6-hydroxycarbonyl-(4S,7R)-[4,7-ethylene-spiro[2.4]heptane]-5-carboxamide and trans-tert-butyl 3-fluoro-4-(hydroxymethyl)piperidine-1-carboxylate.
LC-MS-conditions 08: $t_R$=0.62 min; [M+H]$^+$=420.36.

Example 44

(1S,2R,3R,4R)-[(cis-3-Fluoro-piperidin-4-yl)methyl 2-(((3-methylisoxazol-5-yl)methyl)carbamoyl)spiro[bicyclo[2.2.1]heptane-7,1'-cyclopropane]-3-carboxylate]

Following general procedures A and D, starting from (5R)—N$^5$-((3-methylisoxazol-5-yl)methyl)-(6R)-6-hydroxycarbonyl-(4S,7R)-[4,7-ethylene-spiro[2.4]heptane]-5-carboxamide and cis-tert-butyl 3-fluoro-4-(hydroxymethyl)piperidine-1-carboxylate.
LC-MS-conditions 08: $t_R$=0.61 min; [M+H]$^+$=420.37.

Example 45

(1S,2R,3R,4R)-[3-(Aminomethyl)benzyl 2-((6-bromopyridin-3-yl)carbamoyl)spiro[bicyclo[2.2.1]heptane-7,1'-cyclopropane]-3-carboxylate]

Following general procedures A and D, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and tert-butyl 3-(hydroxymethyl)benzylcarbamate.
LC-MS-conditions 08: $t_R$=0.73 min; [M+H]$^+$=484.14.

Example 46

(1S,2R,3R,4R)-[(trans-3-Fluoro-piperidin-4-yl) 2-(((3-methylisoxazol-5-yl)methyl)carbamoyl)spiro[bicyclo[2.2.1]heptane-7,1'-cyclopropane]-3-carboxylate]

Following general procedures A and D, starting from (5R)—N$^5$-((3-methylisoxazol-5-yl)methyl)-(6R)-6-hydroxycarbonyl-(4S,7R)-[4,7-ethylene-spiro[2.4]heptane]-5-carboxamide and trans-tert-butyl 3-fluoro-4-hydroxypiperidine-1-carboxylate (WO2011/061679).
LC-MS-conditions 08: $t_R$=0.61 min; [M+H]$^+$=406.33.

Example 47

(1S,2R,3R,4R)-[2-(Piperidin-4-yl)ethyl 2-(((5-methylisoxazol-3-yl)methyl)carbamoyl)spiro[bicyclo[2.2.1]heptane-7,1'-cyclopropane]-3-carboxylate]

Following general procedures A and D, starting from (5R)—N$^5$-((5-methylisoxazol-3-yl)methyl)-(6R)-6-hydroxycarbonyl-(4S,7R)-[4,7-ethylene-spiro[2.4]heptane]-5-carboxamide and tert-butyl-4-(2-hydroxyethyl)piperidine-1-carboxylate.
LC-MS-conditions 07: $t_R$=0.56 min; [M+H]$^+$=416.17.

Example 48

(1S,2R,3R,4R)-[(S)-2-(2-(3-Fluoropyrrolidin-1-yl)ethoxy)ethyl 2-((6-bromopyridin-3-yl)carbamoyl)spiro[bicyclo[2.2.1]heptane-7,1'-cyclopropane]-3-carboxylate]

Following general procedure A, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and (S)-2-(2-(3-fluoropyrrolidin-1-yl)ethoxy)ethanol.
LC-MS-conditions 07: $t_R$=0.65 min; [M+H]$^+$=524.10.

Example 49

(1S,2R,3R,4R)-[2-(4-Fluoro-piperidin-4-yl)ethyl 2-(((3-methylisoxazol-5-yl)methyl)carbamoyl)spiro[bicyclo[2.2.1]heptane-7,1'-cyclopropane]-3-carboxylate]

Following general procedures A and D, starting from (5R)—N$^5$-((3-methylisoxazol-5-yl)methyl)-(6R)-6-hydroxycarbonyl-(4S,7R)-[4,7-ethylene-spiro[2.4]heptane]-5-carboxamide and tert-butyl 4-fluoro-4-(2-hydroxyethyl)piperidine-1-carboxylate.
LC-MS-conditions 08: $t_R$=0.64 min; [M+H]$^+$=434.27.

Example 50

(1S,2R,3R,4R)-[(Piperidin-4-yl)methyl 2-((4-bromophenyl)carbamoyl)spiro[bicyclo[2.2.1]heptane-7,1'-cyclopropane]-3-carboxylate]hydrochloride Following general procedures A, F and D, starting from (5R)—N$^5$-(4-bromo-phenyl)-(6R)-6-hydroxycarbonyl-(4S,7R)-[4,7-ethylene-spiro[2.4]heptane]-5-carboxamide and tert-butyl-4-(hydroxymethyl)piperidine-1-carboxylate.
LC-MS-conditions 07: $t_R$=0.74 min; [M+H]$^+$=460.94.

Example 51

(1S,2R,3R,4R)-[(4-Fluoro-piperidin-4-yl)methyl 2-(((3-methylisoxazol-5-yl)methyl)carbamoyl)spiro[bicyclo[2.2.1]heptane-7,1'-cyclopropane]-3-carboxylate]

Following general procedures A and D, starting from (5R)—N$^5$-((3-methylisoxazol-5-yl)methyl)-(6R)-6-hydroxycarbonyl-(4S,7R)-[4,7-ethylene-spiro[2.4]heptane]-5-carboxamide and tert-butyl 4-fluoro-4-(hydroxymethyl)piperidine-1-carboxylate.
LC-MS-conditions 08: $t_R$=0.62 min; [M+H]$^+$=420.34.

Example 52

(1S,2R,3R,4R)-[(Piperidin-4-yl)methyl 2-(((3-methylisoxazol-5-yl)methyl)carbamoyl)spiro[bicyclo[2.2.1]heptane-7,1'-cyclopropane]-3-carboxylate]

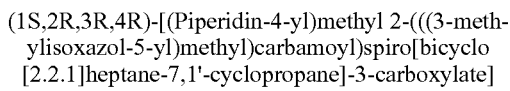

Following general procedures A and D, starting from (5R)—$N^5$-((3-methylisoxazol-5-yl)methyl)-(6R)-6-hydroxycarbonyl-(4S,7R)-[4,7-ethylene-spiro[2.4]heptane]-5-carboxamide and tert-butyl 4-(hydroxymethyl)piperidine-1-carboxylate.

LC-MS-conditions 07: $t_R$=0.61 min; [M+H]$^+$=402.14.

Example 53

(1S,2R,3R,4R)-[(S)-4-(3-Fluoropyrrolidin-1-yl)butyl 2-((6-bromopyridin-3-yl)carbamoyl)spiro[bicyclo[2.2.1]heptane-7,1'-cyclopropane]-3-carboxylate]

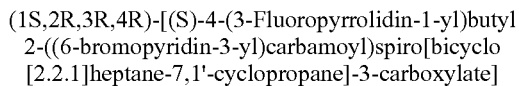

Following general procedure A, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and (S)-4-(3-fluoropyrrolidin-1-yl)butanol.

LC-MS-conditions 08: $t_R$=0.73 min; [M+H]$^+$=508.12.

Example 54

(1S,2R,3R,4R)-[4-(Pyrrolidin-1-yl)butyl 2-((6-bromopyridin-3-yl)carbamoyl)spiro[bicyclo[2.2.1]heptane-7,1'-cyclopropane]-3-carboxylate]

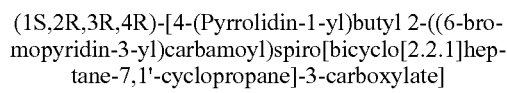

Following general procedure A, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and 4-(pyrrolidin-1-yl)butan-1-ol.

LC-MS-conditions 08: $t_R$=0.74 min; [M+H]$^+$=490.15.

Example 55

(1S,2R,3R,4R)-[(4-Fluoro-piperidin-4-yl)methyl 2-((6-bromopyridin-3-yl)carbamoyl)spiro[bicyclo[2.2.1]heptane-7,1'-cyclopropane]-3-carboxylate]

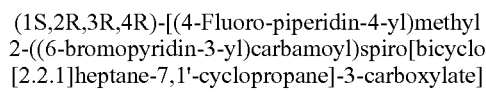

Following general procedures A and D, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and tert-butyl 4-fluoro-4-(hydroxymethyl)piperidine-1-carboxylate.

LC-MS-conditions 08: $t_R$=0.70 min; [M+H]$^+$=480.34.

Example 56

(1S,2R,3R,4R)-[(3,3-Difluoro-piperidin-4-yl) 2-((6-bromopyridin-3-yl)carbamoyl)spiro[bicyclo[2.2.1]heptane-7,1'-cyclopropane]-3-carboxylate]

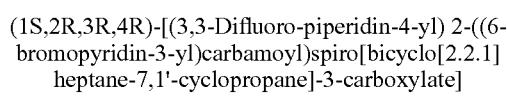

Following general procedures A and D, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and tert-butyl 3,3-difluoro-4-hydroxypiperidine-1-carboxylate.

LC-MS-conditions 08: $t_R$=0.71 min; [M+H]$^+$=484.31.

Example 57

(1S,2R,3R,4R)-[(trans-3-Fluoro-piperidin-4-yl) 2-((6-bromopyridin-3-yl)carbamoyl)spiro[bicyclo[2.2.1]heptane-7,1'-cyclopropane]-3-carboxylate]

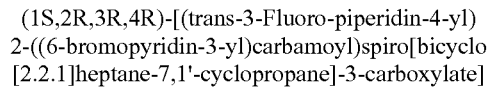

Following general procedures A and D, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and trans-tert-butyl 3-fluoro-4-hydroxypiperidine-1-carboxylate (WO2009/054941).

LC-MS-conditions 08: $t_R$=0.68 min; [M+H]$^+$=466.22.

Example 58

(1S,2R,3R,4R)-[2-(4-Fluoro-piperidin-4-yl)ethyl 2-(((5-methylisoxazol-3-yl)methyl)carbamoyl)spiro[bicyclo[2.2.1]heptane-7,1'-cyclopropane]-3-carboxylate]

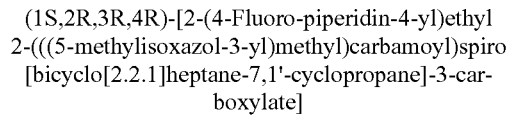

Following general procedures A and D, starting from (5R)—$N^5$-((5-methylisoxazol-3-yl)methyl)-(6R)-6-hydroxycarbonyl-(4S,7R)-[4,7-ethylene-spiro[2.4]heptane]-5-carboxamide and tert-butyl 4-fluoro-4-(2-hydroxyethyl)piperidine-1-carboxylate.

LC-MS-conditions 08: $t_R$=0.65 min; [M+H]$^+$=434.28.

Example 59

(1S,2R,3R,4R)-[(4-Fluoro-piperidin-4-yl)methyl 2-(((5-methylisoxazol-3-yl)methyl)carbamoyl)spiro[bicyclo[2.2.1]heptane-7,1'-cyclopropane]-3-carboxylate]

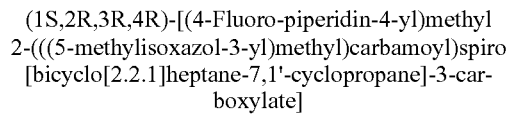

Following general procedures A and D, starting from (5R)—$N^5$-((5-methylisoxazol-3-yl)methyl)-(6R)-6-hydroxycarbonyl-(4S,7R)-[4,7-ethylene-spiro[2.4]heptane]-5-carboxamide and tert-butyl 4-fluoro-4-(hydroxymethyl)piperidine-1-carboxylate.

LC-MS-conditions 08: $t_R$=0.63 min; [M+H]$^+$=420.36.

Example 60

(1S,2R,3R,4R)-[Piperidin-4-yl 2-((4-bromo-2-fluorobenzyl)carbamoyl)spiro[bicyclo[2.2.1]heptane-7,1'-cyclopropane]-3-carboxylate]

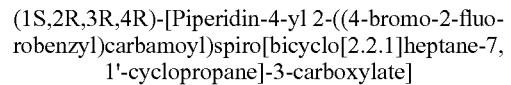

Following general procedures A and D, starting from (5R)—$N^5$-(4-bromo-2-fluorophenyl-methyl)-(6R)-6-hydroxycarbonyl-(4S,7R)-[4,7-ethylene-spiro[2.4]heptane]-5-carboxamide and tert-butyl 4-hydroxypiperidine-1-carboxylate.

LC-MS-conditions 07: $t_R$=0.69 min; [M+H]$^+$=479.09.

Example 61

(1S,2R,3R,4R)-[(3,3-Difluoro-piperidin-4-yl) 2-(((3-methylisoxazol-5-yl)methyl)carbamoyl)spiro[bicyclo[2.2.1]heptane-7,1'-cyclopropane]-3-carboxylate]

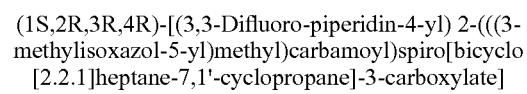

Following general procedures A and D, starting from (5R)—$N^5$-((3-methylisoxazol-5-yl)methyl)-(6R)-6-hydroxycarbonyl-(4S,7R)-[4,7-ethylene-spiro[2.4]heptane]-5-carboxamide and tert-butyl 3,3-difluoro-4-hydroxypiperidine-1-carboxylate.

LC-MS-conditions 08: $t_R$=0.63 min; [M+H]$^+$=424.32.

Example 62

(1S,2R,3R,4R)-[cis-(3-Fluoro-piperidin-4-yl) 2-(((3-methylisoxazol-5-yl)methyl)carbamoyl)spiro[bicyclo[2.2.1]heptane-7,1'-cyclopropane]-3-carboxylate]

Following general procedures A and D, starting from (5R)—$N^5$-((3-methylisoxazol-5-yl)methyl)-(6R)-6-hydroxycarbonyl-(4S,7R)-[4,7-ethylene-spiro[2.4]heptane]-5-carboxamide and cis-tert-butyl 3-fluoro-4-hydroxypiperidine-1-carboxylate (WO2011/061679).
LC-MS-conditions 08: $t_R$=0.60 min; [M+H]$^+$=406.34.

Example 63

(1S,2R,3R,4R)-[2-(piperazin-1-yl)ethyl 2-(((5-methylisoxazol-3-yl)methyl)carbamoyl)spiro[bicyclo[2.2.1]heptane-7,1'-cyclopropane]-3-carboxylate]

Following general procedures A and D, starting from (5R)—$N^5$-((5-methylisoxazol-3-yl)methyl)-(6R)-6-hydroxycarbonyl-(4S,7R)-[4,7-ethylene-spiro[2.4]heptane]-5-carboxamide and tert-butyl-4-(2-hydroxyethyl)piperazine-1-carboxylate.
LC-MS-conditions 07: $t_R$=0.47 min; [M+H]$^+$=417.00.

Example 64

(1S,2R,3R,4R)-[(cis-3-Fluoro-piperidin-4-yl)methyl 2-((6-bromopyridin-3-yl)carbamoyl)spiro[bicyclo[2.2.1]heptane-7,1'-cyclopropane]-3-carboxylate]

Following general procedures A and D, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and cis-tert-butyl 3-fluoro-4-(hydroxymethyl)piperidine-1-carboxylate.
LC-MS-conditions 08: $t_R$=0.69 min; [M+H]$^+$=480.37.

Example 65

(1S,2R,3R,4R)-[(3-Amino-3-oxopropyl) 2-(((3-methylisoxazol-5-yl)methyl)carbamoyl)spiro[bicyclo[2.2.1]heptane-7,1'-cyclopropane]-3-carboxylate]

Following general procedure A, starting from (5R)—$N^5$-((3-methylisoxazol-5-yl)methyl)-(6R)-6-hydroxycarbonyl-(4S,7R)-[4,7-ethylene-spiro[2.4]heptane]-5-carboxamide and 3-hydroxypropanamide.
LC-MS-conditions 08: $t_R$=0.65 min; [M+H]$^+$=376.24.

Example 66

(1S,2R,3R,4R)-[(3,3-Difluoro-piperidin-4-yl)ethyl 2-(((3-methylisoxazol-5-yl)methyl)carbamoyl)spiro[bicyclo[2.2.1]heptane-7,1'-cyclopropane]-3-carboxylate]

Following general procedures A and D, starting from (5R)—$N^5$-((3-methylisoxazol-5-yl)methyl)-(6R)-6-hydroxycarbonyl-(4S,7R)-[4,7-ethylene-spiro[2.4]heptane]-5-carboxamide and tert-butyl 3,3-difluoro-4-(2-hydroxyethyl)piperidine-1-carboxylate.
LC-MS-conditions 08: $t_R$=0.65 min; [M+H]$^+$=452.39.

Example 67

(1S,2R,3R,4R)-[(4-Pyrrolidino-4-oxobutyl) 2-((6-bromopyridin-3-yl)carbamoyl)spiro[bicyclo[2.2.1]heptane-7,1'-cyclopropane]-3-carboxylate]

Following general procedures A and D, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and 4-hydroxy-1-(pyrrolidin-1-yl)butan-1-one
LC-MS-conditions 08: $t_R$=0.89 min; [M+H]$^+$=504.17.

Example 68

(1S,2R,3R,4R)-[(3-Amino-3-oxopropyl) 2-((6-bromopyridin-3-yl)carbamoyl)spiro[bicyclo[2.2.1]heptane-7,1'-cyclopropane]-3-carboxylate]

Following general procedure A, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and 3-hydroxypropanamide.
LC-MS-conditions 07: $t_R$=0.67 min; [M+H]$^+$=435.84.

Example 69

(1S,2R,3R,4R)-[(S)-2-(2-(3-Fluoropyrrolidin-1-yl)ethoxy)ethyl 2-((4-bromo-2-fluorobenzyl)carbamoyl)spiro[bicyclo[2.2.1]heptane-7,1'-cyclopropane]-3-carboxylate]

Following general procedure A, starting from (5R)—$N^5$-(4-bromo-2-fluorophenyl-methyl)-(6R)-6-hydroxycarbonyl-(4S,7R)-[4,7-ethylene-spiro[2.4]heptane]-5-carboxamide and (S)-2-(2-(3-fluoropyrrolidin-1-yl)ethoxy)ethanol.
LC-MS-conditions 07: $t_R$=0.71 min; [M+H]$^+$=555.08.

Example 70

(1S,2R,3R,4R)-[(trans-3-Fluoro-piperidin-4-yl)methyl 2-((6-bromopyridin-3-yl)carbamoyl)spiro[bicyclo[2.2.1]heptane-7,1'-cyclopropane]-3-carboxylate]

Following general procedures A and D, starting from (5R)—$N^5$-(2-bromo-pyrid-5-yl)-(6R)-6-hydroxycarbonyl-(4S,7R)-[4,7-ethylene-spiro[2.4]heptane]-5-carboxamide and trans-tert-butyl 3-fluoro-4-(hydroxymethyl)piperidine-1-carboxylate.
LC-MS-conditions 08: $t_R$=0.70 min; [M+H]$^+$=480.35.

Example 71

(1S,2R,3R,4R)-[2-(piperazin-1-yl)ethyl 2-((4-bromo-2-fluorobenzyl)carbamoyl)spiro[bicyclo[2.2.1]heptane-7,1'-cyclopropane]-3-carboxylate]dihydrochloride Following general procedures A and D, starting from (5R)—$N^5$-(4-bromo-2-fluorophenyl-methyl)-(6R)-6-hydroxycarbonyl-(4S,7R)-[4,7-ethylene-spiro[2.4]heptane]-5-carboxamide and tert-butyl-4-(2-hydroxyethyl)piperazine-1-carboxylate.
LC-MS-conditions TFA: $t_R$=0.76 min; [M+H]$^+$=508.30.

Example 72

(1S,2R,3R,4R)-[2-(Piperidin-4-yl)ethyl 2-((4-bromo-2-fluorobenzyl)carbamoyl)spiro[bicyclo[2.2.1]heptane-7,1'-cyclopropane]-3-carboxylate]hydrochloride Following general procedures A and D, starting from (5R)—N$^5$-(4-bromo-2-fluorophenyl-methyl)-(6R)-6-hydroxycarbonyl-(4S,7R)-[4,7-ethylene-spiro[2.4]heptane]-5-carboxamide and tert-butyl 4-(2-hydroxyethyl)piperidine-1-carboxylate.

LC-MS-conditions 07: $t_R$=0.73 min; [M+H]$^+$=507.13.

Example 73

(1S,2R,3R,4R)-[2-(3,3-Difluoro-piperidin-4-yl)ethyl 2-((6-bromopyridin-3-yl)carbamoyl)spiro[bicyclo[2.2.1]heptane-7,1'-cyclopropane]-3-carboxylate]

Following general procedures A and D, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and tert-butyl 3,3-difluoro-4-(2-hydroxyethyl)piperidine-1-carboxylate.

LC-MS-conditions 08: $t_R$=0.72 min; [M+H]$^+$=512.33.

Example 74

(1S,2R,3R,4R)-[cis-3-Fluoro-piperidin-4-yl 2-((6-bromopyridin-3-yl)carbamoyl)spiro[bicyclo[2.2.1]heptane-7,1'-cyclopropane]-3-carboxylate]

Following general procedures A and D, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and cis-tert-butyl 3-fluoro-4-hydroxypiperidine-1-carboxylate.

LC-MS-conditions 08: $t_R$=0.68 min; [M+H]$^+$=466.22.

Example 75

(1S,2R,3R,4R)-[2-(2-(3,3-Difluoropyrrolidin-1-yl)ethoxy)ethyl 2-((6-bromopyridin-3-yl)carbamoyl)spiro[bicyclo[2.2.1]heptane-7,1'-cyclopropane]-3-carboxylate]

Following general procedure A, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and 2-(2-(3,3-difluoropyrrolidin-1-yl)ethoxy)ethanol.

LC-MS-conditions TFA: $t_R$=0.81 min; [M+Na]$^+$=564.10.

Example 76

(1S,2R,3R,4R)-[1-Benzyl-piperidin-4-yl 2-((6-bromopyridin-3-yl)carbamoyl)spiro[bicyclo[2.2.1]heptane-7,1'-cyclopropane]-3-carboxylate]

Following general procedure A, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and 1-benzylpiperidin-4-ol.

LC-MS-conditions 08: $t_R$=0.79 min; [M+H]$^+$=538.38.

Example 77

(1S,2R,3R,4R)-[(4,4-Difluoro-5-(pyrrolidin-1-yl))pent-2-yl 2-((6-bromopyridin-3-yl)carbamoyl)spiro[bicyclo[2.2.1]heptane-7,1'-cyclopropane]-3-carboxylate]

Following general procedure A, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and 4,4-difluoro-5-(pyrrolidin-1-yl)pentan-2-ol.

LC-MS-conditions 08: $t_R$=0.75 min; [M+H]$^+$=540.35.

Example 78

(1S,2R,3R,4R)-[(4,4-Difluoro-5-(pyrrolidin-1-yl))pent-1-yl 2-((6-bromopyridin-3-yl)carbamoyl)spiro[bicyclo[2.2.1]heptane-7,1'-cyclopropane]-3-carboxylate]

Following general procedure A, starting from (5R)—N$^5$-(2-bromo-pyrid-5-yl)-(6R)-6-hydroxycarbonyl-(4S,7R)-[4,7-ethylene-spiro[2.4]heptane]-5-carboxamide and 4,4-difluoro-5-(pyrrolidin-1-yl)pentan-1-ol.

LC-MS-conditions 08: $t_R$=0.75 min; [M+H]$^+$=540.36.

II. Biological Assays

In Vitro Assay

The ALX receptor and FPRL2 agonistic activities of the compounds of formula (I) are determined in accordance with the following experimental method.

Experimental Method:

Intracellular Calcium Measurements:

Cells expressing recombinant human ALX receptor and the G-protein Gα16 (HEK293-hALXR-Gα16) were grown to 80% confluency in Growing Medium (GM). Cells were detached from culture dishes with a cell dissociation buffer (Invitrogen, 13151-014), and collected by centrifugation at 1,000 rpm at rt for 5 min in Assay Buffer (AB) (equal parts of Hank's BSS (Gibco, 14065-049) and DMEM without Phenol Red (Gibco, 11880-028)). After 60 min incubation at 37° C. under 5% $CO_2$ in AB supplemented with 1 µM Fluo-4 (AM) (Invitrogen, F14202), and 20 mM HEPES (Gibco, 15630-056), the cells were washed and resuspended in AB. They were then seeded onto 384-well FLIPR assay plates (Greiner, 781091) at 50,000 cells in 70 µl per well and sedimented by centrifugation at 1,000 rpm for 1 min. Stock solutions of test compounds were made up at a concentration of 10 mM in DMSO, and serially diluted in AB to concentrations required for activation dose response curves. WKYMVm (Phoenix Peptides) was used as a reference agonist. FLIPR384 or FLIPR Tetra instruments (Molecular Devices) were operated according to the manufacturer's standard instructions, adding 4 µl of test compound dissolved at 10 mM in DMSO and diluted prior to the experiment in assay buffer to obtain the desired final concentration. Changes in fluorescence were monitored before and after the addition of test compounds at lex=488 nm and lem=540 nm. Emission peak values above base level after compounds addition were exported after base line subtraction. Values were normalized to high-level control (WKYMVm compound, 10 nM final concentration) after subtraction of the base line value (AB addition).

Agonistic activities of exemplified compounds are displayed in Table 1.

TABLE 1

| Compound | ALX receptor EC$_{50}$ [nM] |
|---|---|
| Example 1 | 8.1 |
| Example 2 | 15.1 |
| Example 3 | 22.7 |
| Example 4 | 52.1 |
| Example 5 | 242 |
| Example 6 | 257 |
| Example 7 | 303 |
| Example 8 | 753 |
| Example 9 | 2.5 |
| Example 10 | 3.1 |
| Example 11 | 8.8 |
| Example 12 | 15.5 |
| Example 13 | 17.9 |
| Example 14 | 25.8 |
| Example 15 | 34.6 |
| Example 16 | 53.7 |
| Example 17 | 79.4 |
| Example 18 | 87.7 |
| Example 19 | 105 |
| Example 20 | 118 |
| Example 21 | 146 |
| Example 22 | 217 |
| Example 23 | 281 |
| Example 24 | 289 |
| Example 25 | 330 |
| Example 26 | 406 |
| Example 27 | 585 |
| Example 28 | 734 |
| Example 29 | 790 |
| Example 30 | 808 |
| Example 31 | 2.2 |
| Example 32 | 226 |
| Example 33 | 30.7 |
| Example 34 | 21.6 |
| Example 35 | 2.9 |
| Example 36 | 0.4 |
| Example 37 | 1.4 |
| Example 38 | 1.8 |
| Example 39 | 3.7 |
| Example 40 | 4.6 |
| Example 41 | 5.2 |
| Example 42 | 7.2 |
| Example 43 | 7.6 |
| Example 44 | 8.1 |
| Example 45 | 9.3 |
| Example 46 | 9.7 |
| Example 47 | 9.7 |
| Example 48 | 9.9 |
| Example 49 | 10.4 |
| Example 50 | 10.8 |
| Example 51 | 11.3 |
| Example 52 | 11.5 |
| Example 53 | 11.9 |
| Example 54 | 14.6 |
| Example 55 | 18.5 |
| Example 56 | 28.2 |
| Example 57 | 33.4 |
| Example 58 | 36.7 |
| Example 59 | 41.4 |
| Example 60 | 43.4 |
| Example 61 | 50.1 |
| Example 62 | 77.5 |
| Example 63 | 79.0 |
| Example 64 | 106 |
| Example 65 | 107 |
| Example 66 | 113 |
| Example 67 | 125 |
| Example 68 | 135 |
| Example 69 | 145 |
| Example 70 | 157 |
| Example 71 | 162 |
| Example 72 | 262 |
| Example 73 | 270 |
| Example 74 | 280 |
| Example 75 | 403 |
| Example 76 | 2060 |

TABLE 1-continued

| Compound | ALX receptor EC$_{50}$ [nM] |
|---|---|
| Example 77 | 1750 |
| Example 78 | 3740 |

The invention claimed is:
1. A compound of the formula (I)

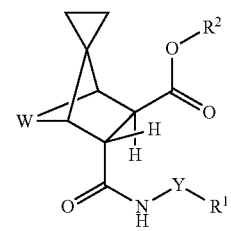

wherein
W represents —CH$_2$CH$_2$— or —CH=CH—;
Y represents a bond or a (C$_1$-C$_2$)alkandiyl group;
R$^1$ represents an aryl- or a heteroaryl-group, wherein the groups are independently unsubstituted, mono-, di- or tri-substituted, wherein the substituents are independently halogen, (C$_1$-C$_4$)alkyl, (C$_1$-C$_4$)alkoxy, (C$_1$-C$_2$)fluoroalkyl or (C$_1$-C$_2$)fluoroalkoxy;
R$^2$ represents
(C$_3$-C$_6$)cycloalkyl, which is unsubstituted or mono-substituted with R$^3$R$^4$N—CH$_2$— or heterocyclyl-methyl;
(C$_2$-C$_6$)alkyl, which is
mono-substituted with —NR$^3$R$^4$, —C(O)NR$^5$R$^6$, (C$_1$-C$_4$)alkoxy, or (C$_1$-C$_4$)alkoxy which is mono-substituted with heterocyclyl, wherein the heterocyclyl is unsubstituted, or mono-substituted at a nitrogen atom with (C$_1$-C$_4$)alkyl and/or independently mono- or di-substituted at one or two of the carbon atoms with substituents independently selected from halogen or (C$_1$-C$_4$)alkyl; or
mono- or di-substituted with hydroxy;
(C$_1$-C$_6$)alkyl, which is mono-substituted
with (C$_3$-C$_6$)cycloalkyl, which cycloalkyl is mono-substituted with —NR$^3$R$^4$;
with heterocyclyl, wherein the heterocyclyl is unsubstituted, or mono-substituted at a nitrogen atom with (C$_1$-C$_4$)alkyl and/or independently mono- or di-substituted at one or two of the carbon atoms with substituents independently selected from halogen or (C$_1$-C$_4$)alkyl; or
with an aryl- or heteroaryl-group, wherein the groups are independently unsubstituted, mono-, di- or tri-substituted, wherein the substituents are independently halogen, (C$_1$-C$_4$)alkyl, —CH$_2$NH$_2$ or —SO$_2$NH$_2$;
(C$_3$-C$_5$)fluoroalkyl, which is mono-substituted with heterocyclyl, wherein the heterocyclyl is unsubstituted or independently mono- or di-substituted at one or two of the carbon atoms with substituents independently selected from halogen or (C$_1$-C$_4$)alkyl; or
heterocyclyl, which is unsubstituted, or mono-substituted at a nitrogen atom with (C$_1$-C$_4$)alkyl or benzyl, and/or independently mono- or di-substituted at one or two of the carbon atoms with substituents independently selected from halogen or $(C_1-C_4)$alkyl;

$R^3$ and $R^4$ represent independently from each other hydrogen or $(C_1-C_3)$alkyl; and $R^5$ and $R^6$ represent independently from each other hydrogen or methyl; or $R^5$ and $R^6$ form, together with the nitrogen that carries them, a pyrrolidine or piperidine ring; or a salt thereof.

2. The compound according to claim 1, wherein

Y represents a bond or a methandiyl group;

$R^1$ represents an aryl- or a heteroaryl-group, wherein the groups are independently unsubstituted, mono- or di-substituted, wherein the substituents are independently halogen, $(C_1-C_4)$alkyl, $(C_1-C_4)$alkoxy or $(C_1-C_2)$fluoroalkyl;

$R^2$ represents cyclopentyl or cyclohexyl, which are independently unsubstituted or mono-substituted with $R^3R^4N-CH_2-$ or heterocyclyl-methyl;

$(C_2-C_6)$alkyl, which is mono-substituted with $-NR^3R^4$, $-C(O)NR^5R^6$, or $(C_1-C_4)$alkoxy which is mono-substituted with heterocyclyl, wherein the heterocyclyl is unsubstituted or mono- or di-substituted at one of the carbon atoms with fluoro; or $(C_1-C_6)$alkyl, which is mono-substituted
with heterocyclyl, wherein the heterocyclyl is unsubstituted, or mono-substituted at a nitrogen atom with $(C_1-C_4)$alkyl and/or mono- or di-substituted at one of the carbon atoms with fluoro; or with an aryl- or heteroaryl-group, wherein the groups are independently unsubstituted, mono-, or di-substituted, wherein the substituents are independently $(C_1-C_4)$alkyl or $-CH_2NH_2$;

$(C_3-C_5)$fluoroalkyl, which is mono-substituted with heterocyclyl, wherein the heterocyclyl is unsubstituted or mono- or di-substituted at one of the carbon atoms with fluoro; or heterocyclyl, which is unsubstituted or mono- or di-substituted at one of the carbon atoms with fluoro;

$R^3$ represents hydrogen or $(C_1-C_3)$alkyl;

$R^4$ represents $(C_1-C_3)$alkyl; and $R^5$ and $R^6$ form, together with the nitrogen that carries them, a pyrrolidine or piperidine ring; or a salt thereof.

3. The compound according to claim 1, wherein W represents $-CH_2CH_2-$; or a salt thereof.

4. The compound according to claim 1, wherein W represents $-CH=CH-$; or a salt thereof.

5. The compound according to claim 1, wherein Y represents a bond or a methandiyl group; or a salt thereof.

6. The compound according to claim 1, wherein $R^1$ represents an aryl- or a heteroaryl-group, wherein the groups are independently mono- or di-substituted, wherein the substituents are independently halogen or $(C_1-C_4)$alkyl; or a salt thereof.

7. The compound according to claim 1, wherein $R^2$ represents cyclopentyl or cyclohexyl, which are independently unsubstituted or mono-substituted with $R^3R^4N-CH_2-$ or heterocyclyl-methyl;

$(C_2-C_6)$alkyl, which is mono-substituted with $-NR^3R^4$, $-C(O)NR^5R^6$, or $(C_1-C_4)$alkoxy which is mono-substituted with heterocyclyl, wherein the heterocyclyl is unsubstituted or mono- or di-substituted at one of the carbon atoms with fluoro; or $(C_1-C_6)$alkyl, which is mono-substituted
with heterocyclyl, wherein the heterocyclyl is unsubstituted, or mono-substituted at a nitrogen atom with $(C_1-C_4)$alkyl and/or mono- or di-substituted at one of the carbon atoms with fluoro; or with an aryl- or heteroaryl-group, wherein the groups are independently unsubstituted, mono-, or di-substituted, wherein the substituents are independently $(C_1-C_4)$alkyl or $-CH_2NH_2$;

$(C_3-C_5)$fluoroalkyl, which is mono-substituted with heterocyclyl, wherein the heterocyclyl is unsubstituted or mono- or di-substituted at one of the carbon atoms with fluoro; or heterocyclyl, which is unsubstituted or mono- or di-substituted at one of the carbon atoms with fluoro;

or a salt thereof.

8. The compound according to claim 1, wherein $R^2$ represents $(C_1-C_5)$alkyl, which is mono-substituted with heterocyclyl, wherein the heterocyclyl is unsubstituted, or mono-substituted at a nitrogen atom with $(C_1-C_4)$alkyl and/or mono- or di-substituted at one of the carbon atoms with fluoro; or a salt thereof.

9. The compound according to claim 1, wherein $R^4$ represents $(C_1-C_3)$alkyl; or a salt thereof.

10. The compound according to claim 1, wherein the compound is:

(1S,2R,3R,4R)-[Piperidin-4-ylmethyl 2-((6-bromopyridin-3-yl)carbamoyl)spiro[bicyclo[2.2.1]heptane-7,1'-cyclopropane]-3-carboxylate];

(1S,2R,3R,4R)-[Piperidin-4-yl 2-((6-bromopyridin-3-yl)carbamoyl)spiro[bicyclo[2.2.1]heptane-7,1'-cyclopropane]-3-carboxylate];

(1S,2R,3R,4R)-[Piperidin-4-ylmethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Piperidin-4-ylmethyl 2-((4-bromo-2-fluorobenzyl)carbamoyl)spiro[bicyclo[2.2.1]heptane-7,1'-cyclopropane]-3-carboxylate];

(1S,2R,3R,4R)-[(S*)-2,3-Dihydroxypropyl 2-((6-bromopyridin-3-yl)carbamoyl)spiro[bicyclo[2.2.1]heptane-7,1'-cyclopropane]-3-carboxylate];

(1S,2R,3R,4R)-[1-Methylpiperidin-4-yl 2-((6-bromopyridin-3-yl)carbamoyl)spiro[bicyclo[2.2.1]heptane-7,1'-cyclopropane]-3-carboxylate];

(1S,2R,3R,4R)-[2-Methoxyethyl 2-((6-bromopyridin-3-yl)carbamoyl)spiro[bicyclo[2.2.1]heptane-7,1'-cyclopropane]-3-carboxylate];

(1S,2R,3R,4R)-[1,2,2,6,6-Pentamethylpiperidin-4-yl 2-((6-bromopyridin-3-yl)carbamoyl)spiro[bicyclo[2.2.1]heptane-7,1'-cyclopropane]-3-carboxylate];

(1S,2R,3R,4R)-[Piperidin-3-yl 2-((6-bromopyridin-3-yl)carbamoyl)spiro[bicyclo[2.2.1]heptane-7,1'-cyclopropane]-3-carboxylate];

(1S,2R,3R,4R)-[2-(Piperidin-3-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[(S)-2-(Piperidin-2-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[Piperidin-3-ylmethyl 2-((6-bromopyridin-3-yl)carbamoyl)spiro[bicyclo[2.2.1]heptane-7,1'-cyclopropane]-3-carboxylate];

(1S,2R,3R,4R)-[(R)-Pyrrolidin-3-yl 2-((6-bromopyridin-3-yl)carbamoyl)spiro[bicyclo[2.2.1]heptane-7,1'-cyclopropane]-3-carboxylate];

(1S,2R,3R,4R)-[1-Methylpyrrolidin-3-yl 2-((6-bromopyridin-3-yl)carbamoyl)spiro[bicyclo[2.2.1]heptane-7,1'-cyclopropane]-3-carboxylate];

(1S,2R,3R,4R)-[1-Methylpyrrolidin-3-yl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Piperidin-3-yl 2-(((5-methylisoxazol-3-yl)methyl)carbamoyl)spiro[bicyclo[2.2.1]heptane-7,1'-cyclopropane]-3-carboxylate];

(1S,2R,3R,4R)-[2-(Piperidin-3-yl)ethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Piperidin-3-ylmethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[(R)-Pyrrolidin-3-yl 2-(((5-methylisoxazol-3-yl)methyl)carbamoyl)spiro[bicyclo[2.2.1]heptane-7,1'-cyclopropane]-3-carboxylate];

(1S,2R,3R,4R)-[(S)-2-(Piperidin-2-yl)ethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[1-Dimethylaminoprop-3-yl 2-((6-bromopyridin-3-yl)carbamoyl)spiro[bicyclo[2.2.1]heptane-7,1'-cyclopropane]-3-carboxylate];

(1S,2R,3R,4R)-[1-Methyl-piperidin-2-ylmethyl 2-((6-bromopyridin-3-yl)carbamoyl)spiro[bicyclo[2.2.1]heptane-7,1'-cyclopropane]-3-carboxylate];

(1S,2R,3R,4R)-[2-(2-Oxopyrrolidin-1-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[Azetidin-3-yl 2-((6-bromopyridin-3-yl)carbamoyl)spiro[bicyclo[2.2.1]heptane-7,1'-cyclopropane]-3-carboxylate];

(1S,2R,3R,4R)-[1-Dimethylaminoprop-3-yl 2-(((5-methylisoxazol-3-yl)methyl)carbamoyl)spiro[bicyclo[2.2.1]heptane-7,1'-cyclopropane]-3-carboxylate];

(1S,2R,3R,4R)-[1-Methyl-piperidin-2-ylmethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[1-Dimethylaminoeth-2-yl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Isobutyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Cyclopentyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Propyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[2-(2-(Pyrrolidin-1-yl)ethoxy)ethyl 2-((6-bromopyridin-3-yl)carbamoyl)spiro[bicyclo[2.2.1]heptane-7,1'-cyclopropane]-3-carboxylate];

(1S,2R,3R,4R)-[2-(2-(Pyrrolidin-1-yl)ethoxy)ethyl 2-((4-bromo-2-fluorobenzyl)carbamoyl)spiro[bicyclo[2.2.1]heptane-7,1'-cyclopropane]-3-carboxylate];

(1S,2R,3R,4R)-[2-(2-(Pyrrolidin-1-yl)ethoxy)ethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[(S)-2-(2-(3-Fluoropyrrolidin-1-yl)ethoxy)ethyl 2-(((5-methylisoxazol-3-yl)methyl)carbamoyl)spiro[bicyclo[2.2.1]heptane-7,1'-cyclopropane]-3-carboxylate]; or (1R,4S,5R,6R)-[Piperidin-4-ylmethyl 5-((4-bromophenyl)carbamoyl)spiro[bicyclo[2.2.1]hept[2]ene-7,1'-cyclopropane]-6-carboxylate];

or a salt thereof.

11. The compound according to claim 1, wherein the compound is:

(1S,2R,3R,4R)-[2-(Piperidin-4-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[2-(Piperazin-1-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[2-(cis-3-Fluoro-piperidin-4-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[2-(cis-3-Fluoro-piperidin-4-yl)ethyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[2-(4-Fluoro-piperidin-4-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[(Piperidin-4-yl)methyl 2-((6-bromopyridin-3-yl)carbamoyl)spiro[bicyclo[2.2.1]heptane-7,1'-cyclopropane]-3-carboxylate];

(1S,2R,3R,4R)-[(S)-2-(2-(3-Fluoropyrrolidin-1-yl)ethoxy)ethyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[(trans-3-Fluoro-piperidin-4-yl)methyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[(cis-3-Fluoro-piperidin-4-yl)methyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[3-(Aminomethyl)benzyl 2-((6-bromopyridin-3-yl)carbamoyl)spiro[bicyclo[2.2.1]heptane-7,1'-cyclopropane]-3-carboxylate];

(1S,2R,3R,4R)-[(trans-3-Fluoro-piperidin-4-yl) 2-(((3-methylisoxazol-5-yl)methyl)carbamoyl)spiro[bicyclo[2.2.1]heptane-7,1'-cyclopropane]-3-carboxylate];

(1S,2R,3R,4R)-[2-(Piperidin-4-yl)ethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[(S)-2-(2-(3-Fluoropyrrolidin-1-yl)ethoxy)ethyl 2-(((6-bromopyridin-3-yl)carbamoyl)spiro[bicyclo[2.2.1]heptane-7,1'-cyclopropane]-3-carboxylate];

(1S,2R,3R,4R)-[2-(4-Fluoro-piperidin-4-yl)ethyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[(Piperidin-4-yl)methyl 2-((4-bromophenyl)carbamoyl)spiro[bicyclo[2.2.1]heptane-7,1'-cyclopropane]-3-carboxylate];

(1S,2R,3R,4R)-[(4-Fluoro-piperidin-4-yl)methyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[(Piperidin-4-yl)methyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[(S)-4-(3-Fluoropyrrolidin-1-yl)butyl 2-((6-bromopyridin-3-yl)carbamoyl)spiro[bicyclo[2.2.1]heptane-7,1'-cyclopropane]-3-carboxylate];

(1S,2R,3R,4R)-[4-(Pyrrolidin-1-yl)butyl 2-((6-bromopyridin-3-yl)carbamoyl)spiro[bicyclo[2.2.1]heptane-7,1'-cyclopropane]-3-carboxylate];

(1S,2R,3R,4R)-[(4-Fluoro-piperidin-4-yl)methyl 2-((6-bromopyridin-3-yl)carbamoyl)spiro[bicyclo[2.2.1]heptane-7,1'-cyclopropane]-3-carboxylate];

(1S,2R,3R,4R)-[(3,3-Difluoro-piperidin-4-yl) 2-((6-bromopyridin-3-yl)carbamoyl)spiro[bicyclo[2.2.1]heptane-7,1'-cyclopropane]-3-carboxylate];

(1S,2R,3R,4R)-[(trans-3-Fluoro-piperidin-4-yl) 2-((6-bromopyridin-3-yl)carbamoyl)spiro[bicyclo[2.2.1]heptane-7,1'-cyclopropane]-3-carboxylate];

(1S,2R,3R,4R)-[2-(4-Fluoro-piperidin-4-yl)ethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[(4-Fluoro-piperidin-4-yl)methyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[Piperidin-4-yl 2-((4-bromo-2-fluorobenzyl)carbamoyl)spiro[bicyclo[2.2.1]heptane-7,1'-cyclopropane]-3-carboxylate];

(1S,2R,3R,4R)-[(3,3-Difluoro-piperidin-4-yl) 2-(((3-methylisoxazol-5-yl)methyl)carbamoyl)spiro[bicyclo[2.2.1]heptane-7,1'-cyclopropane]-3-carboxylate];

(1S,2R,3R,4R)-[cis-(3-Fluoro-piperidin-4-yl) 2-(((3-methylisoxazol-5-yl)methyl)carbamoyl)spiro[bicyclo[2.2.1]heptane-7,1'-cyclopropane]-3-carboxylate];

(1S,2R,3R,4R)-[2-(Piperazin-1-yl)ethyl 2-(((5-methylisoxazol-3-yl)methyl)carbamoyl)spiro[bicyclo[2.2.1]heptane-7,1'-cyclopropane]-3-carboxylate];

(1S,2R,3R,4R)-[(cis-3-Fluoro-piperidin-4-yl)methyl 2-((6-bromopyridin-3-yl)carbamoyl)spiro[bicyclo[2.2.1]heptane-7,1'-cyclopropane]-3-carboxylate];

(1S,2R,3R,4R)-[(3-Amino-3-oxopropyl) 2-(((3-methylisoxazol-5-yl)methyl)carbamoyl)spiro[bicyclo[2.2.1]heptane-7,1'-cyclopropane]-3-carboxylate];

(1S,2R,3R,4R)-[(3,3-Difluoro-piperidin-4-yl)ethyl 2-(((3-methylisoxazol-5-yl)methyl)carbamoyl)spiro[bicyclo[2.2.1]heptane-7,1'-cyclopropane]-3-carboxylate];

(1S,2R,3R,4R)-[(4-Pyrrolidino-4-oxobutyl) 2-((6-bromopyridin-3-yl)carbamoyl)spiro[bicyclo[2.2.1]heptane-7,1'-cyclopropane]-3-carboxylate];

(1S,2R,3R,4R)-[(3-Amino-3-oxopropyl) 2-((6-bromopyridin-3-yl)carbamoyl)spiro[bicyclo[2.2.1]heptane-7,1'-cyclopropane]-3-carboxylate];

(1S,2R,3R,4R)-[(S)-2-(2-(3-Fluoropyrrolidin-1-yl)ethoxy)ethyl 2-((4-bromo-2-fluorobenzyl)carbamoyl)spiro[bicyclo[2.2.1]heptane-7,1'-cyclopropane]-3-carboxylate];

(1S,2R,3R,4R)-[(trans-3-Fluoro-piperidin-4-yl)methyl 2-((6-bromopyridin-3-yl)carbamoyl)spiro[bicyclo[2.2.1]heptane-7,1'-cyclopropane]-3-carboxylate];

(1S,2R,3R,4R)-[2-(Piperazin-1-yl)ethyl 2-((4-bromo-2-fluorobenzyl)carbamoyl)spiro[bicyclo[2.2.1]heptane-7,1'-cyclopropane]-3-carboxylate];

(1S,2R,3R,4R)-[2-(Piperidin-4-yl)ethyl 2-((4-bromo-2-fluorobenzyl)carbamoyl)spiro[bicyclo[2.2.1]heptane-7,1'-cyclopropane]-3-carboxylate];

(1S,2R,3R,4R)-[2-(3,3-Difluoro-piperidin-4-yl)ethyl 2-((6-bromopyridin-3-yl)carbamoyl)spiro[bicyclo[2.2.1]heptane-7,1'-cyclopropane]-3-carboxylate];

(1S,2R,3R,4R)-[cis-3-Fluoro-piperidin-4-yl 2-((6-bromopyridin-3-yl)carbamoyl)spiro[bicyclo[2.2.1]heptane-7,1'-cyclopropane]-3-carboxylate];

(1S,2R,3R,4R)-[2-(2-(3,3-Difluoropyrrolidin-1-yl)ethoxy)ethyl 2-((6-bromopyridin-3-yl)carbamoyl)spiro[bicyclo[2.2.1]heptane-7,1'-cyclopropane]-3-carboxylate];

(1S,2R,3R,4R)-[1-Benzyl-piperidin-4-yl 2-((6-bromopyridin-3-yl)carbamoyl)spiro[bicyclo[2.2.1]heptane-7,1'-cyclopropane]-3-carboxylate];

(1S,2R,3R,4R)-[(4,4-Difluoro-5-(pyrrolidin-1-yl))pent-2-yl 2-((6-bromopyridin-3-yl)carbamoyl)spiro[bicyclo[2.2.1]heptane-7,1'-cyclopropane]-3-carboxylate]; or (1S,2R,3R,4R)-[(4,4-Difluoro-5-(pyrrolidin-1-yl))pent-1-yl 2-((6-bromopyridin-3-yl)carbamoyl)spiro[bicyclo[2.2.1]heptane-7,1'-cyclopropane]-3-carboxylate];

or a salt thereof.

12. A medicament comprising the compound according to claim 1 and a pharmaceutically acceptable salt.

13. A pharmaceutical composition comprising, as an active principle, a compound according to claim 1 or a pharmaceutically acceptable salt thereof, and at least one therapeutically inert excipient.

14. A method of treating a disease comprising administering to a subject in need thereof a compound according to claim 1, wherein the disease is inflammatory diseases, obstructive airway diseases, allergic conditions, HIV-mediated retroviral infections, cardiovascular disorders, neuroinflammation, neurological disorders, pain, prion-mediated diseases, or amyloid-mediated disorders.

* * * * *